(12) United States Patent
Wu et al.

(10) Patent No.: US 8,058,516 B2
(45) Date of Patent: Nov. 15, 2011

(54) RICE METALLOTHIONEIN PROMOTERS

(75) Inventors: Wei Wu, Chesterfield, MO (US); Peter Hajdukiewicz, Chesterfield, MO (US); Qi Wang, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 679 days.

(21) Appl. No.: 11/834,317

(22) Filed: Aug. 6, 2007

(65) Prior Publication Data

US 2008/0227639 A1    Sep. 18, 2008

Related U.S. Application Data

(60) Continuation-in-part of application No. 11/595,983, filed on Nov. 13, 2006, now Pat. No. 7,790,958, which is a division of application No. 09/815,264, filed on Mar. 23, 2001, now Pat. No. 7,365,185, which is a continuation-in-part of application No. 09/702,134, filed on Oct. 31, 2000, now abandoned, which is a continuation-in-part of application No. 09/620,392, filed on Jul. 19, 2000, now abandoned.

(51) Int. Cl.
*A01H 5/00* (2006.01)
*A01H 5/10* (2006.01)
*C12N 15/82* (2006.01)
*C12N 15/11* (2006.01)

(52) U.S. Cl. ....... 800/298; 536/24.1; 800/300; 800/287; 800/320; 504/116.1

(58) Field of Classification Search ................. None
See application file for complete search history.

(56) References Cited

U.S. PATENT DOCUMENTS

| | | | |
|---|---|---|---|
| 4,784,949 A | 11/1988 | Gelfand et al. | 435/68 |
| 4,956,282 A | 9/1990 | Goodman et al. | 435/69.51 |
| 5,011,912 A | 4/1991 | Hopp et al. | 530/387 |
| 6,093,545 A | 7/2000 | Goodearl et al. | 435/6 |
| 6,194,636 B1 * | 2/2001 | McElroy et al. | 800/278 |
| 7,365,185 B2 | 4/2008 | Boukharov et al. | 536/24.1 |
| 2004/0034888 A1 | 2/2004 | Liu et al. | 536/23.1 |
| 2006/0253933 A1 | 11/2006 | Brown et al. | 435/6 |
| 2006/0265782 A1 | 11/2006 | Hinkle et al. | 800/278 |
| 2007/0011783 A1 | 1/2007 | Liu et al. | 800/278 |
| 2007/0016974 A1 | 1/2007 | Byrum et al. | 800/278 |
| 2007/0039076 A1 | 2/2007 | Boukharov et al. | 435/6 |
| 2007/0067865 A1 | 3/2007 | Kovalic et al. | 435/6 |
| 2007/0083945 A1 | 4/2007 | Byrum et al. | 536/23.1 |
| 2007/0143878 A1 | 6/2007 | Bhat et al. | 435/6 |
| 2007/0150978 A1 | 6/2007 | Byrum | 536/23.1 |
| 2008/0008996 A1 | 1/2008 | Byrum | 435/6 |
| 2008/0072354 A1 | 3/2008 | Byrum et al. | 435/6 |
| 2008/0120751 A1 | 5/2008 | Andersen et al. | 435/6 |
| 2008/0127376 A1 | 5/2008 | Fincher et al. | 536/23.6 |

FOREIGN PATENT DOCUMENTS

WO    WO 00/18922    4/2000

OTHER PUBLICATIONS

Hsieh et al (1998, DNA Sequence 9:9-18).*
Hsieh et al (1999 GenBank Accession No. U46159).*
Wing et al (1998, GenBank Accession No. AQ257482).*
Rounsley et al (Curr Opin. in Plant Biol. 1:136-141).*
Rounsley et al (1998, Curr Opin. In Plant Biol. 1:136-141).*
U.S. Appl. No. 11/353,150, filed Feb. 14, 2006, Andersen et al.
U.S. Appl. No. 11/331,019, filed Jan. 13, 2006, Fincher et al.
U.S. Appl. No. 11/330,364, filed Jan. 12, 2006, Abad et al.
U.S. Appl. No. 11/330,082, filed Jan. 12, 2006, Buehler et al.
U.S. Appl. No. 11/329,388, filed Jan. 11, 2006, Andersen et al.
U.S. Appl. No. 11/329,175, filed Jan. 11, 2006, CaJacob et al.
Aach et al., "ent-kaurene biosynthesis in a cell-free system from wheat (*Triticum aestivum* L.) seedlings and the localization of ent-kaurene synthetase in plastids of three species," *Planta*, 197(2):333-342, 1995.
Adams et al., Complementary DNA sequencing: expressed sequence tags and human genome project, *Science*, 252(5013):1651-1656, 1991.
Ait-Ali et al., "The LS locus of pea encodes the gibberellin biosynthesis enzyme ent-kaurene synthase A," *Plant J.*, 11(3):443-454, 1997.
Anaviev et al., "Oat-maize chromosome addition lines: a new system for mapping the maize genome," *Proc. Natl. Acad. Sci. USA*, 94:3524-3529, 1997.
Anton et al., "Sequencing and overexpression of the *Escherichia coli* aroE gene encoding shikimate dehydrogenase," *Biochem. J.*, 249:319-326, 1988.
Attwood, "The babel of bioinoformatics," *Science*, 290(5491):471-473, 2000.
Benfey et al., "The CaMV 35S enhancer contains at least two domains which can confer different developmental and tissue-specific expression patterns," *EMBO J.*, 8(8):2195-2202, 1989.
Benfey et al., "The cauliflower mosaic virus 35S promoter: combinatorial regulation of transcription in plants," *Science*, 250:959-966, 1990.
Bensen et al., "Cloning and characterization of the maize An1 gene," *Plant Cell*, 7:75-84, 2004. Bentley, "The shikimate pathway—a metabolic tree with many branches," *Critical Rev. Biochem. Mol. Biol.*, 25(5):307-384, 1990.
Birkenbihl et al., "Cosmid-derived map of *E. coli* strain BHE2600 in comparison to the map of strain W3110." *Nucleic Acids Res.*, 17(13):5057-5069, 1989.
Bishop et al., "The tomato dwarf gene isolated by heterologous transposon tagging encodes the first member of a new cytochrome P450 family," *Plant Cell*, 8:959-969, 1996.
Bonner et al., "Cloning of cDNA encoding the bifunctional dehydroquinase-shikimate dehydrogenase of aromatic-amino-acid biosynthesis in nicotiana tabacum," *Biochem. J.*, 362:11-14, 1994.
Bork, "Powers and pitfalls in sequence analysis: the 70% hurdle," *Genome Res.*, 10:398-400, 2000.
Bougri et al., "Members of a low-copy number gene family encoding glutamyl-tRNA reductase are differentially expressed in barley," *Plant J.*, 9(6):867-878, 1996.

(Continued)

*Primary Examiner* — Anne Kubelik

(74) *Attorney, Agent, or Firm* — SNR Denton US LLP; Erin Robert, Esq.

(57) ABSTRACT

The present invention provides non-coding regulatory element polynucleotide molecules isolated from the Metallothionein gene of *Oryza sativa* and useful for expressing transgenes in plants. The invention further discloses compositions, polynucleotide constructs, transformed host cells, transgenic plants and seeds containing the *Oryza sativa* regulatory polynucleotide sequences, and methods for preparing and using the same.

15 Claims, 2 Drawing Sheets

OTHER PUBLICATIONS

Broun et al., "Catalytic plasticity of fatty acid modification enzymes underlying chemical diversity of plant lipids," *Science*, 282:1315-1317, 1998.

Bukanov et al., "Ordered cosmid library and high-resolution physical-genetic Aap of helicobacter pylori strain NCTC11638," *Mol. Microbiol.*, 11(3):509-523, 1994.

Charles et al., "Isolation, characterization and nucleotide sequences of the aroC genes encoding chorismate synthase from *Salmonella typhi* and *Escherichia coli*," *J. Gen. Microbiol.*, 136:353-358, 1990.

Chen et al., "Microcolinearity in sh2-homologous regions of the maize, rice, and sorghum genomes," *Proc. Natl. Acad. Sci. USA*, 94:3431-3435, 1997.

Cho et al., "Regulation of root hair initiation and expansin gene expression in *Arabidopsis*," *The Plant Cell*, 14:3237-3253, 2002.

Coulson et al., "Toward a physical map of the genome of the nematode *Caenorhabditis elegans*," *Proc. Natl. Acad. Sci. USA*, 83:7821-8725, 1986.

Day et al., "Cloning of the cDNA for glutamyl-tRNA synthetase from *Arabidopsis thaliana*," *Biochim. Biophys. Acta*, 1399(2-3):219-224, 1998.

Donald et al., "Mutation of either G box of I box sequences profoundly affects expression from the *Arabidopsis* rbcS-1A promoter," *EMBO J*, 9(6):1717-1726, 1990.

Duncan et al., "The overexpression and complete amino acid sequence of *Escherichia coli* 3-dehydroquinase," *Biochem. J.*, 238:475-483, 1986.

Eberhard et al., "Cloning and expression in yeast of a higher plant chorismate mutase," *FEBS Letters*, 334(2):233-236, 1993.

Ebert et al., "Identification of an essential upstream element in the nopaline synthase promoter by stable and transient assays," *Proc. Natl. Acad. Sci. USA*, 84(16):5745-5749, 1987.

Efstratiadis et al., "Enzymatic in vitro synthesis of globin genes," *Cell*, 7:279-288, 1976.

Eiglmeier et al., "Use of an ordered cosmid library to deduce the genomic organization of *mycobacterium leprae*," *Mol. Microbiol.*, 7(2):197-206, 1993.

Entrez Accession No. 1213067, dated Mar. 1, 1996.
Entrez Accession No. 1220402, dated Mar. 5, 1996.
Entrez Accession No. 1421741, dated Oct. 17, 1996.
Entrez Accession No. 1524045, dated Aug. 20, 1997.
Entrez Accession No. 153878, dated Jun. 15, 1990.
Entrez Accession No. 170374, dated Sep. 15, 1989.
Entrez Accession No. 2160544, dated Jun. 5, 1997.
Entrez Accession No. 2224890, dated Jul. 31, 1997.
Entrez Accession No. 2224892, dated Jul. 31, 1997.
Entrez Accession No. 2257714, dated Jul. 15, 1997.
Entrez Accession No. 2316104, dated Aug. 8, 1997.
Entrez Accession No. 2708690, dated May 7, 1998.
Entrez Accession No. 3068709, dated Apr. 2 1998.
Entrez Accession No. 3080490, dated Jan. 12, 1999.
Entrez Accession No. 3093410, dated Oct. 1, 1998.
Entrez Accession No. 313150, dated Jun. 13, 1995.
Entrez Accession No. 3135277, dated May 16, 1998.
Entrez Accession No. 3288821, dated Jul. 20, 1998.
Entrez Accession No. 3420233, dated Apr. 20, 1998.
Entrez Accession No. 3435196, dated Sep. 21, 1998.
Entrez Accession No. 3694811, dated Sep. 24, 1998.
Entrez Accession No. 3925407, dated Nov. 24, 1998.
Entrez Accession No. 4001680, dated Dec. 11, 1998.
Entrez Accession No. 40973, dated Jul. 12, 1995.
Entrez Accession No. 40978, dated Sep. 12, 1993.
Entrez Accession No. 429153, dated Dec. 2, 1993.
Entrez Accession No. 474964, dated Jul. 27, 1995.
Entrez Accession No. 48906, dated Jun. 30, 1993.
Entrez Accession No. 520943, dated Feb. 26, 1997.
Entrez Accession No. 551666, dated Jan. 25, 1995.
Entrez Accession No. 551855, dated Apr. 12, 1995.
Entrez Accession No. 987267, dated Jul. 31, 1995.
Entrez Accession No. AAC17095; GI:315616, dated Apr. 5, 1999.
Entrez Accession No. AB011416, dated Feb. 5, 1999.
Entrez Accession No. AB015492, dated Dec. 11, 1998.
Entrez Accession No. AC003058, dated May 16, 1998.
Entrez Accession No. AF010169, dated Aug. 9, 1997.
Entrez Accession No. AF017431, dated Jan. 2, 1999.
Entrez Accession No. AF038152, dated May 7, 1998.
Entrez Accession No. AF049236, dated Apr. 22, 1998.
Entrez Accession No. AF058763, dated Aug. 16, 1998.
Entrez Accession No. AF060481, dated Oct. 4, 1998.
Entrez Accession No. AF063901, dated Jul. 21, 1998.
Entrez Accession No. AF067773, dated Sep. 22, 1998.
Entrez Accession No. AF083948, dated Nov. 25, 1998.
Entrez Accession No. AJ225107, dated Oct. 1, 1998.
Entrez Accession No. AL022602, dated Jan. 12, 1999.
Entrez Accession No. AP000836; GI:6539551, dated Aug. 12, 2000.
Entrez Accession No. AY013245, dated May 7, 2002.
Entrez Accession No. D63474 D16312, dated Jul. 27, 1995.
Entrez Accession No. D88382, dated Mar. 17, 1998.
Entrez Accession No. M21071 J03227, dated Sep. 15, 1989.
Entrez Accession No. M27715, dated Jun. 15, 1990.
Entrez Accession No. M63245, dated Mar. 11, 1996.
Entrez Accession No. M87280 M99707, dated Apr. 12, 1995.
Entrez Accession No. U32579, dated Sep. 16, 1995.
Entrez Accession No. U54770, dated Oct. 18, 1996.
Entrez Accession No. U61385, dated Aug. 1, 1997.
Entrez Accession No. U61386, dated Aug. 1, 1997.
Entrez Accession No. U63652, dated Jun. 6, 1997.
Entrez Accession No. U93215, dated Jul. 15, 1997.
Entrez Accession No. W49458, dated May 28, 1996.
Entrez Accession No. X04306, dated Jul. 12, 1995.
Entrez Accession No. X59509 S55160, dated Jun. 30, 1993.
Entrez Accession No. X73535, dated Jun. 13, 1995.
Entrez Accession No. X81413, dated Jan. 25, 1995.
Entrez Accession No. X82831, dated Mar. 1, 1996.
Entrez Accession No. X86101, dated Nov. 8, 1996.
Entrez Accession No. X96943, dated Aug. 20, 1997.
Entrez Accession No. Y00710, dated Sep. 12, 1993.
Entrez Accession No. Y12809, dated Dec. 2, 1997.
Entrez Accession No. Z26519, dated Dec. 2, 1993.
EST Database AA501409, dated Aug. 19, 1997.

Evans et al., "Immunodetection of recombinant proteins based on antibodies directed against a metal binding peptide engineered for purification by immobilized metal affinity chromatography," *J. Immunol. Meth.*, 156(2):231-238, 1992 (Abstract only).

Fiedler et al., "The formation of homogentisate in the biosynthesis of tocopherol and plastoquinone in spinach chloroplast," *Planta*, 155:511-515, 1982.

Garbe et al., "The mycobacterium tuberculosis shikimate pathway genes: evolutionary relationship between biosynthetic and catabolic 3-dehydroquinases," *Mol. Gen. Genet.*, 228:385-392, 1991.

Gasser et al., "Structure, expression and evolution of the 5-enolpyruvylshikimate-3-phonsphate synthase genes of petunia and tomato," *J. Biol. Chem.*, 263:4280-4289, 1988.

Gaubier et al., "A chlorophyll synthetase gene from *Arabidopsis thaliana*," *Mol. Gen. Genet.*, 249:58-64, 1995.

GenBank Accession No. AC005922, dated Nov. 14, 1998.
GenBank Accession No. AC018632, dated Dec. 15, 1999.
GenBank Accession No. AF015462, dated Jul. 16, 1998.
GenBank Accession No. AI834598, dated Feb. 2, 2000.
GenBank Accession No. AI861202, dated Jul. 19, 1999.
GenBank Accession No. AK105219, dated Feb. 16, 2008.
GenBank Accession No. AK243071, dated Feb. 16, 2008.
GenBank Accession No. AK243301, dated Feb. 16, 2008.
GenBank Accession No. AK287615, dated Feb. 16, 2008.
GenBank Accession No. AK288523, dated Feb. 16, 2008.
GenBank Accession No. AK288568, dated Feb. 16, 2008.
GenBank Accession No. AL731784, dated Jan. 16, 2006.
GenBank Accession No. AL772425, dated Jan. 16, 2006.
GenBank Accession No. AL845346, dated Jan. 16, 2006.
GenBank Accession No. AP008218, dated May 19, 2007.
GenBank Accession No. AQ402486, dated Mar. 13, 1999.
GenBank Accession No. AU033328, dated Apr. 28, 1999.
GenBank Accession No. AW871780, dated Dec. 11, 2001.
GenBank Accession No. AZ134591, dated Jun. 2, 2000.
GenBank Accession No. BE428765, dated Jul. 26, 2000.

GenBank Accession No. BF542512, dated Dec. 11, 2000.
GenBank Accession No. BQ603510, dated Jun. 24, 2002.
GenBank Accession No. BX513761, dated May 27, 2003.
GenBank Accession No. CT829024, dated Apr. 8, 2008.
GenBank Accession No. CT831683, dated Apr. 8, 2008.
GenBank Accession No. CT831684, dated Apr. 8, 2008.
GenBank Accession No. CT831685, dated Apr. 8, 2008.
GenBank Accession No. CT831686, dated Apr. 8, 2008.
GenBank Accession No. CT832527, dated Apr. 8, 2008.
GenBank Accession No. CT837596, dated Apr. 8, 2008.
GenBank Accession No. DR37H4T, dated Nov. 22, 2002.
GenBank Accession No. E03435, dated Sep. 29, 1997.
GenBank Accession No. H30177, dated Aug. 16, 1995.
GenBank Accession No. L37750, dated Aug. 3, 1995.
GenBank Accession No. NM_001073615, dated Feb. 14, 2008.
GenBank Accession No. U03774, dated Jun. 22, 1994.
GenBank Accession No. U50333, Feb. 28, 1997.
GenBank Accession No. W21756, dated May 6, 1996.
GenBank Accession No. X74737, dated Jan. 21, 1999.
GenBank Accession No. X80265, dated Feb. 26, 1997.
GenEMBL Accession No. AF096555, dated Jul. 22, 1999.
GenEMBL Accession No. AL096768, dated Dec. 12, 1999.
GenSeq Accession No. AAZ35275, dated Mar. 27, 2000.
Gerhold et al., "It's the genes! EST access to human genome content," *BioEssays,* 18(2):973-981, 1996.
Gibson et al., "The bacteriochlorophyll biosynthesis gene, bchM, of Rhodobacter sphaeroides encodes S-adenosyl-l-methionine: Mg protoporphyrin IX methyltransferase," *FEBS Letters,* 352:127-130, 1994.
Goers et al., "The differential allosteric regulation of two chorismate-mutase isoenzymes of *Nicotiana silvestris*," *Planta,* 162:117-124, 1984.
Goff, "Rica as a model for cereal genomics," *Curr. Opin. Plant Biol.,* 2:86-89, 1999.
Hedden et al., "Gibberellin biosynthesis: enzymes, genes and their regulation," *Annu. Rev. Plant Physiol. Plant Mol. Biol.,* 48:4631-460, 1997.
Herrmann, "The shikimate pathway as an entry to aromatic secondary metabolism," *Plant Physiol.,* 107:7-12, 1995.
Hong, "A rapid and accurate strategy for rice contig map construction by combination of fingerprinting and hybridization," *Plant Mol. Biol.,* 35:129-133, 1997.
Hundle et al., "Functional assignment of erwinia herbicola Eho10 carotenoid genes expressed in *Escherichia coli*," *Mol. Gen. Genet.,* 245:406-416, 1994.
Ibba, "Biochemistry and bioinformatics: when worlds collide," *Trends in Biochem. Sci.,* 27(2):64, 2000.
Iyer et al., "Quod erat demonstrandum? The mystery of experimental validation of apparently erroneous computational analysis of protein sequences," *Genome Biol.,* 2(12):1-11, 2001.
Johnston et al., "Cloning and characterization of potato cDNAs involved in tetrapyrrole biosynthesis: ferrochelatase (Accession No. AJ005802), Chloroplatic protoporphyrinogen IX oxidase (Accession No. AJ225107), and mitochondrial protoporphyrinogen IX oxidase (Accession No. AJ225108)," *Plant Physiol.,* 118:329-331, 1998.
Kang et al., "Cloning and molecular analyses of a gibberellin 20-oxidase gene expressed specifically in developing seeds of watermelon," *Plant Physiology,* 121:373-382, 1999.
Keon et al., "Isolation and heterologous expression of a gene encoding 4-hydroxyphenylpyruvate dioxygenase from the wheat leaf-spot pathogen," *FEMS Microbiol. Lett.,* 161:337-343, 1998.
Kidwell et al., "Transposable elements as sources of variation in animals and plants," *Proc. Natl. Acad. Sci. USA,* 94:7704-7711, 1997.
Kim et al., "A 20 nucleotide upstream element is essential for the nopaline synthase (nos) promoter activity," *Plant Molecular Biology,* 24:105-117, 1994.
Kim et al., "Construction and characterization of a human bacterial artificial chromosome library," *Genomics,* 34:213-218, 1996.
Knott et al., "Randomly picked cosmid clones overlap the pyrB and oriC gap in the physical map of the *E. coli* chromosome," *Nucleic Acids Res.,* 16:2601-2612, 1988.

Ko et al., "An 'equalized cDNA' library by the reassociation of short double-stranded cDNA," *Nucleic Acids Res.,* 18(19):5705-5711, 1990.
Kurata et al., "A 300 kilobase interval genetic map of rice including 883 expressed sequences," *Natur Gen.,* 8(4):362-372, 1994.
Kyrpides et al., "Whole-genome sequence annotation: 'going wrong with confidence'," *Mol. Microbiol.,* 32:886-887, 1999.
Lange et al., "Cloning and expression of a gibberellin 2β,3β-hydroxylase cDNA from pumpkin endosperm," *Plant Cell,* 9(8):1459-1467, 1997.
Lange et al., "Cloning gibberellin dioxygenase genes from pumpkin endosperm by heterologous expression of enzyme activities in *Escherichia coli*," *Proc. Natl. Acad. Sci. USA,* 94(12):6553-6558, 1997.
Lange et al., "Expression cloning of a gibberellin 20-oxidase, a multifunctional enzyme involved in gibberellin biosynthesis," *Proc. Natl. Acad. Sci. USA,* 91(18):8552-8556, 1994.
Liepman et al., "Sequence analysis of a cDNA encoding alanine:glyoxylate amino transferase from *Arabidopsis* (Accession No. AF063901)," *Plant Physiol.,* 117:1125-1127, 1998.
Lim et al., "Porphobilinogen deaminase is encoded by a single gene in *Arabidopsis thaliana* and is targeted to the chloroplasts," *Plant Mol. Biol.,* 26:863-872, 1994.
Mahairas et al., "Sequence-tagged connectors: a sequence approach to mapping and scanning the human genome," *Proc. Natl. Acad. Sci. USA,* 96:9739-9744, 1999.
Martin et al., "Mendel's dwarfing gene: cDNAs from the le alleles and function of the expressed proteins," *Proc. Natl. Acad. Sci. USA,* 94(16):8907-8911, 1997.
Martin et al., "MYB transcription factors in plants," *Trends Genet.,* 13(2):67-73, 1997.
McCombie et al., "*Caenorhabditis elegans* expressed sequence tags identify gene families and disease gene homologues," *Nature Gen.,* 1:124-131, 1992.
Meinkoth et al., "Hybridization of nucleic acids immobilized on solid supports," *Anal. Biochem.,* 138:267-284, 1984.
Mende et al., "The geranylgeranyl diphosphate synthase gene of *Gibberella fijikuroi*: isolation and expression," *Mol. Gen. Genet.,* 255(1):96-105, 1997.
Mohan et al., "Genome mapping, molecular markers and marker-assisted selection crop plants," *Mol. Breed.,* 3:87-103, 1997.
Nakane et al., "Nucleotide sequence of the shikimate kinase gene (arol) of *Bacillus subtilis*," *J. Ferment. Bioeng.,* 77:312-314, 1994.
Nakayashiki et al., "Nucleotide sequence of a cDNA clone encoding glutamyl-tRNA reductase from rice (Accession No. AB011416)," *Plant Physiol.,* 117:332, 1998.
NCBI Accession No. AAA34069, corresponding to gi:535771, dated Sep. 11, 1994.
NCBI Accession No. D23883, dated Nov. 29, 1993.
NCBI Accession No. S42508, dated May 8, 1993.
Norris et al., "Complementation of the *Arabidopsis* pds 1 mutation with the gene encoding p-hydroxyphenylpyruvate dioxygenase," *Plant Physiol.,* 117:1317-1323, 1998.
Odell et al., "Identification of DNA sequences required for activity of the cauliflower mosaic virus 35S promoter," *Nature,* 313:810-812, 1985.
Oka et al., "Replication origin of the *Escherichia coli* K-12 chromosome: the size and structure of the minimum DNS segment carrying the information for autonomous replication," *Mod. Gen. Genet.,* 178(1):9-20, 1980.
Okubo et al., "Large scale cDNA sequencing for analysis of quantitative and qualitative aspects of gene expression," *Nature Gen.,* 2:173-179, 1992.
Perez-Florez et al., "Expression analysis of a GA 20-oxidase in embryos from two sorghum lines with contrasting dormancy: possible participation of this gene in the hormonal control of germination," *J. of Experimental Botany,* 54(390):2071-2079, 2003.
Phillips et al., "Isolation and expression of three gibberellin 20-oxidase cDNA clones from *Arabidopsis*," *Plant Physiol.,* 108(3):1049-1057, 1995.
Piechulla et al., "Identification of tomato Lhc promoter regions necessary for circadian expression," *Plant Molecular Biology,* 38:655-662, 1998.

Porra, "Recent progress in porphyrin and chlorophyll biosynthesis," *Photochem. Photobiol.*, 65(3):492-516, 1997.

Russell et al., "Structural features can be unconserved in proteins with similar folds. An analysis of side-chain to side-chain contacts secondary structure and accessibility," *J. Mol. Biol.*, 244:332-350, 1994.

Sakamoto et al., "An overview of gibberellin metabolism enzyme genes and their related mutants in rice," *Plant Physiol.*, 134:1642-1653, 2004.

Schmitz et al., "The tomato blind gene encodes a MYB transcription factor that controls the formation of lateral meristems," *Proc. Nat. Acad Sci.*, 99(2):1064-1069, 2002.

Schumann et al., "Identification of three cDNA clones expressed in the leaf extension zone and with altered patterns of expression in the slender mutant of barley: a tonoplast intrinsic protein, a putative structural protein and protochlorophylide oxidoreductase," *Plant Mol. Biol.*, 31:529-537, 1996.

Seffernick et al., "Melamine deaminase and atrazine chlorohydrolase: 98 percent identical but functionally different," *J. Bacteriol*, 183(3):2405-2410, 2001.

SIGMA Chemical Catalogue (Sigma Chemical Co.; P.O. Box 14508, St. Louis, MO 63178) 1993, product Nos. 01256, 03628, 04375, pp. 736-737.

Smith et al., "Partial purification and characterization of the gibberellin A20 3β-hydroxylase from seeds of *Phaseolus vulgaris*," *Plant Physiol.*, 94:1390-1401, 1990.

Smith et al., "The first step of gibberellin biosynthesis in pumpkin is catalyzed by at least two copalyl diphosphate synthases encoded by differentially regulated genes," *Plant Physiol.*, 118:1411-1419, 1998.

Stammers et al., "Rapid purification and characterization of HIV-1 reverse transcriptase and RNaseH engineered to incorporate a C-terminal tripeptide α-tubulin epitope," *FEBS Lett.*, 283(2):298-302, 1991.

Tanaka et al., "The third member of the hemA gene family encoding glutamyl-tRNA reductase is primarily expressed in roots in *Jordeum vulgare*," *Photosynthesis Res.*, 53:161-171, 1997.

Tanksley et al., "Chromosome landing: a paradigm for map-based gene cloning in plants with large genomes," *Trends in Genet.*, 11(2):63-68, 1995.

Tikhonov et al., "Colinearity and its exceptions in orthologous adh regions of maize and sorghum," *Proc. Natl. Acad. Sci. USA*, 96:7409-7414, 1999.

Van de Loo et al., "An oleate 12-hydroxylase from *Ricirus communis* L. is a fatty acyl desaturase homolog," *Proc. Nat. Acad. Sci.*, 92:6743-6747, 1995.

Venter et al., "A new strategy for genome sequencing," *Nature*, 381:364-366, 1996.

Venter et al., "The sequence of the human genome," *Science*, 291:1304-1351, 2001.

Wang et al., "Construction of a rice bacterial artificial chromosome library and identification of clones linked to the X-21 disease resistance locus," *Plant .J.*, 7(3):525-533, 1995.

Wells et al., "The chemokine information source: identification and characterization of novel chemokines using the WorldWideWeb and expressed sequence tag databases," *J. Leukocyte Biol.*, 61(5):545-550, 1997.

Welsch et al., "Structural and functional characterization of the phytoene synthase promoter from *Arabidopsis thaliana*," *Planta*, 216:523-534, 2003.

Wendel et al., "New isozyme systems for maize (*Zea mays* L.): aconitate hydratase, adenylate kinase, NADH dehydrogenase, and shikimate dehydrogenase," *Biochem. Genet.*, 26(5-6):421- 446, 1998 (Abstract only).

Wenzel et al., "Physical mapping of the mycoplasma pneumoniae genome," *Nucleic Acids Res.*, 16(17):8323-8336, 1988.

Winkler et al., "The maize dwarf3 gene encodes ad cytochrome P450-mediated early step in gibberellin biosynthesis," *Plant Cell*, 7(8):1307-1317, 1995.

Woese et al., "Conservation of primary structure in 16S ribosomal RNA," *Nature*, 254:83-85, 1975.

Yomo et al., "Histochemical studies on protease formation in the cotyledons of germinating bean seeds," *Planta*, 112(1):35-43, 1973.

Zhang et al., "Construction and characterization of two rice bacterial artificial chromosome libraries from the parents of a permanent recombinant inbred mapping population," *Mol. Breeding*, 2:11-24, 1996.

Zhang et al., "Physical mapping of the rice genome with BACs," *Plant Mol. Biol.*, 35:115-127, 1997.

Zwick et al., "Physical mapping of the liguleless linkage group in sorghum bicolor using rice RFLP-selected sorghum BACs," *Genetics*, 248:1983-1992, 1998.

Fukuzawa et al., "The rice metallothionein gene promoter does not direct foreign gene expression in seed endosperm," *Plant Cell Rep.*, 23:231-235, 2004.

Lu et aL, "The Gus reporter-aided analysis of the promoter activities of a rice metallothionein gene reveals different regulatory regions responsible for tissue-specific and inducible expression in transgenic *Arabidopsis*," *Transgenic Res.*, 16:177-191, 2007.

Wong et al, "Down-regulation of metallothionein, a reactive oxygen scavenger, by the small GTPase OsRacl in rice," *Plant Physiology*, 135 :1447-1456, 2004.

Written Description Training material, Example 7, pp. 25-28, Mar. 25, 2008.

* cited by examiner

SEQUENCE LISTING

<160> NUMBER OF SEQ ID NOS: 18

<210> SEQ ID NO 1
<211> LENGTH: 1501
<212> TYPE: DNA
<213> ORGANISM: Oryza sativa

<400> SEQUENCE: 1

| | | | | | |
|---|---|---|---|---|---|
| tttctaaatt | ctgttcattt | gacctgaaat | tttcacgcta | ccatcaggaa | gcctaccgga | 60 |
| gggactgaaa | ttccgaaata | tcagaaattt | caaatgaata | gcattgaaaa | ttactaaatt | 120 |
| tgattttgtt | tgctaaatta | aaaaaaatcc | gtccggaaga | acctcctaca | ggcacccacg | 180 |
| ggtaataacg | aaatttcaga | aaattagatc | tgaaattgta | aaccctgata | cgatgctgtg | 240 |
| agatatcgat | cccaacaact | tcaaattcag | tgaggtatat | gtatttgtgg | tttgattaaa | 300 |
| ggcacgtatt | tcaaattcag | ttgatacatg | aacatgttca | gagcaggttt | gatttggtca | 360 |
| taaaatcatc | aaactcaaat | gcagtctagg | tcatgcaata | aatttaaatt | gaattcgtac | 420 |
| agcaagttaa | tcaaatttga | tgtgtacaag | atatgtttaa | gtacgtgtct | ggtgtagcta | 480 |
| gctagcgccg | tggatttgaa | ggaacgatga | tttggtcagt | agcttgaggg | atctgaattc | 540 |
| ttggcgtatg | ataaacttga | gttcaaaaaa | tacaagacac | atcagttta | tatttcaatt | 600 |
| cgtgtaaacc | attgaattca | attcatgcaa | gggaactgaa | tttgcatatt | tcaattcata | 660 |
| ctcttagctc | atttaaattg | acatttgcac | gatgatgagt | gtgccttttg | ggggtggaac | 720 |
| tggtataagt | ttgactttg | gggaacttaa | tcaaatccag | cgtggttcaa | gcaagaaatt | 780 |
| tgaattcaac | tcatacaaga | aacgtattca | atttcaagct | gtgcaataat | gcatctatct | 840 |
| taagcaaagg | gtctgcatca | tagtactgat | gcatgattga | aacagctaag | aacttgatca | 900 |
| aattcaacgg | ttttcgtga | tgaaagttta | atccagttc | atacaagaaa | cttattcaga | 960 |
| ttgtttgatt | taaatatgag | caacaaggcg | tcgaccttaa | gcaaaggttg | acatcatggt | 1020 |
| gtgaaagcaa | atttgaacct | ggccaaaact | tggatcacat | ttgtccagaa | acttggttca | 1080 |
| gattaacagt | aattaaaata | atgcaacctt | tgcacgtaag | caactactcc | ctccgttcca | 1140 |
| taaaaaacca | atctagtacc | agatgtgaca | catcctagta | ttatgaatct | ggacatacat | 1200 |
| atgtccagat | tcatcgtact | agattatgtc | acatctagta | ttagattcgt | tttttatggg | 1260 |
| acggagggcg | tatataaaaa | tcgtcaatat | ttttatattt | tagggcactt | atcaatacta | 1320 |
| tcttcaacta | agaatgacgc | aattgcaccc | caaacaaata | tgcttttta | aaactccggg | 1380 |
| aaatgcatat | agaaaactga | cgtcaatgaa | tgataatgat | ttttcaaggc | catttcaacc | 1440 |
| agctacatct | ttctggcatg | ataatgcttg | aaataattgt | gcagcttatt | ctcaagcgta | 1500 |
| c | | | | | | 1501 |

<210> SEQ ID NO 2
<211> LENGTH: 1810
<212> TYPE: DNA
<213> ORGANISM: Oryza sativa

<400> SEQUENCE: 2

| | | | | | |
|---|---|---|---|---|---|
| gaacaaataa | ataaaatagg | ccatccagtg | tgatgggttc | aatcactgta | tgtttggctg | 60 |
| tgtgaattac | tggtcatcat | cttgccagtg | tgccctgtgt | aatgttgttc | agtgaaatat | 120 |
| aagatggctt | gttatgaat | tttcctctct | cattatctct | tgttttacc | attctatggt | 180 |
| agaaattaca | gattcccatt | gcttggtcag | atggctgctt | tacctgatct | tagcctgtta | 240 |

-continued

| | |
|---|---|
| ttatattagt gtggtctatg tgtatttcta aattctgttc atttgacctg aaattttcac | 300 |
| gctaccatca ggaagcctac cggagggact gaaattccga aatatcagaa atttcaaatg | 360 |
| aatagcattg aaaattacta aatttgattt tgtttgctaa attaaaaaaa atccgtccgg | 420 |
| aagaacctcc tacaggcacc cacgggtaat aacgaaattt cagaaaatta gatccgaaat | 480 |
| tgtaaaccct gatacgatgc tgtgagatat cgatcccaac aacttcaaat tcagtgaggt | 540 |
| atatgcattt gtggtttgat taaaggcacg tatttcaaat tcagttgata catgaacatg | 600 |
| ttcagagcag gtttgatttg gtcataaaat catcaaactc aaatgcagtc taggtcatgc | 660 |
| aataaattta aattgaattc gtacagcaag ttaatcaaat ttgatgtgta caagatatgt | 720 |
| ttaagtacgt gtctggtgta gctagctagc gccgtggatt tgaaggaacg atgatttggt | 780 |
| cagtagcttg agggatctga attcttggcg tatgataaac ttgagttcaa aaaatacaag | 840 |
| acacatcagt tttatatttc aattcgtgta aaccattgaa ttcaattcat gcaagggaac | 900 |
| tgaatttgca tatttcaatt catactctta gctcatttaa attgacattt gcacgatgat | 960 |
| gagtgtgcct tttgggggtg gaactggtat aagtttgact tttggggaac ttaatcaaat | 1020 |
| ccagcgtggt tcaagcaaga aatttgaatt caactcgtac aagaaacgta ttcaatttca | 1080 |
| agctgtgcaa taatgcatct atcttaagca aagggtctgc atcatagtac tgatgcatga | 1140 |
| ttgaaacagc taagaacttg atcaaattca atggttttc gtgatgaaag tttaaatcca | 1200 |
| gttcatacaa gaaacttatt cagattgttt gatttaaata tgagcaacaa ggcgtcgacc | 1260 |
| ttaagcaaag gttgacatca tggtgtgaaa gcaaatttga acctggccaa aacttggatc | 1320 |
| acatttgtcc agaaacttgg ttcagattaa cagtaattaa aataatgcaa ccttttcacg | 1380 |
| taagcaacta ctccctccgt cccataaaaa accaacctag taccagatgt gacacatcct | 1440 |
| agtattatga atctggacat acatatgtcc agattcatcg tactagatta tgtcacatct | 1500 |
| agtattagat tcgttttta tgggacggag ggcgtatata aaaatcgtca atattttat | 1560 |
| attttgggc acttatcaat actatcttca actaagaatg acgcaattgc accccaaaca | 1620 |
| aatatgcttt tttaaaactc cgggaaatgc atatagaaaa ctgacgtcaa tgaatgataa | 1680 |
| tgattttca aggccatttc aaccagctgc atctttctgg caagataatg cttgaaataa | 1740 |
| ttgtgcagct tattctcaag cgtactacta ctataaatag gggggcatat ctgaactgag | 1800 |
| ttcatatcaa | 1810 |

<210> SEQ ID NO 3
<211> LENGTH: 2000
<212> TYPE: DNA
<213> ORGANISM: Oryza sativa

<400> SEQUENCE: 3

| | |
|---|---|
| tgggtgtcgt tttccttctt gaaggcatca ttactttgct ctctccgttt cttcgggtga | 60 |
| aaaccttgtt ccgattttca gacggacgtt gtttgcgttt caatgctatc ttcctccttg | 120 |
| gagactttgt cttgaagaca ctgccttacg ttgtctgtgg tctgttcata agaagtcgga | 180 |
| gctgttcttt tgagctaggc aacgatgacc tgtgttttaa cctccagttg tatcgttgca | 240 |
| agttttagt ttgttcttca tgtggattta gcctagtttt ccacaacaaa ccgtgcttat | 300 |
| gtgagggttt tggatccggt ttcccctaaa aaactgggcc aagtctcaaa ataggcactc | 360 |
| cctatccttt ttgaggttgt cttaaaaaaa aattactaaa tttgattttg tgtgctaaat | 420 |
| taaaaaaaat ccgtccggaa gaacctccta cagacaccca ctggtaataa cgaaatttcg | 480 |
| gaaatttaga tccgaaattg taaaccctga gagcacacgc aatggtaaag taaggtgcta | 540 |

| | | | | |
|---|---|---|---|---|
| tctataaaac | atgtacatct | cagcaataga | ctaaattaat | agtaaaccac ttcaatggta | 600 |
| tgtctacatg | ggtatctata | gctctctaat | ccattgtctc | gttttttttct atagactatc | 660 |
| tccagattag | tagatagctt | tgctctctct | cttcatttaa | tctcttccaa gtaagaaaat | 720 |
| atgctgacat | gaatctcttg | tagagagcct | atggataacc | attgcgggtg ccctaatacg | 780 |
| atgccgtgcg | atatcgatcc | caacaatact | tcaaattcag | tgaggtatat gtattcgtga | 840 |
| agaagatgat | ccgatcgact | acttcagtga | tgtgtattta | ttgtgtttgat taaaggcaac | 900 |
| gtatttcaaa | tttagttaat | acatgaacat | gttcagagca | ggtttgattt ggtcatagaa | 960 |
| tcatcaaact | caaatgcagt | ctagctcatg | cattaaattt | aaattgaatt cgtacagcaa | 1020 |
| gttaatagaa | ttcgatgtgt | acaagataag | tttaagtacg | tgtctggtgt agctcgcgcc | 1080 |
| atggattga | aggagggatg | atttggtcag | tagcttgagg | gatttgaatt cttggcgtat | 1140 |
| gataaactta | agttcaaaaa | atataagaca | catcagtttt | atatttcaat tcgtgtaaac | 1200 |
| cactgaattc | aattcttgca | agaaatctga | atttgcatat | ttcaattcat actcttagct | 1260 |
| cattcaaatt | gacatttgca | cgatgatgag | tgtgcctttt | ggggtggaac tggtataagt | 1320 |
| ttgacttttg | gggaatttaa | tctaatccag | cgtggttcaa | gcaagaaatt tgaattcaac | 1380 |
| tcgtacaaga | aacgtattca | atttcaagct | gtgcaataat | gcatctatct taagcaaaga | 1440 |
| gtctgcatca | tagtacagat | gcaagattga | aacagctaag | aactttatca aattctgttt | 1500 |
| ttcgtgatga | aagtttaaat | ccagttcata | caaattcaga | ttgtttgctt taaatatgag | 1560 |
| caacaattcg | tctatcttaa | gcaaaggttg | acatcatggt | gtgaaagcaa atttgaacct | 1620 |
| ggccaaaact | tggattacat | ttgcccagaa | acttggttca | gattaacagt aattaaaata | 1680 |
| atgcaaccgt | ggtgcgtaag | caactacata | aaaatcgtca | atatttttat attttttcggc | 1740 |
| acttatcaat | actatattca | actaggaatg | acacaattgc | accccaaaca aatatgcttt | 1800 |
| tttaaaactc | caagaaatgc | atatagaaaa | ctgacgtcaa | tgaatgataa tgattttttca | 1860 |
| aggccatttc | aaccagctac | atctttctgg | caagataatg | ctttgacata attccgcagc | 1920 |
| tttttctcaa | gggtactact | actataaata | ggagggcata | tctgaactga gttcatatca | 1980 |
| agctttcaat | ctctcatttc | | | | 2000 |

<210> SEQ ID NO 4
<211> LENGTH: 1791
<212> TYPE: DNA
<213> ORGANISM: Oryza sativa

<400> SEQUENCE: 4

| | | | | |
|---|---|---|---|---|
| gccatccagt | gtgatgggtt | caatcactgt | atgtttggct | gtgtgaatta ctggtcatca | 60 |
| tcttgccagt | gtgccctgtg | taatgttgtt | cagtgaaata | taagatggct tgtttatgaa | 120 |
| ttttcctctc | tcattatctc | ttgttttttac | cattctatgg | tagaaattac agattcccat | 180 |
| tgcttggtca | gatggctgct | ttacctgatc | ttagcctgtt | attatattag tgtggtctat | 240 |
| gtgtatttct | aaattctgtt | catttgacct | gaaattttca | cgctaccatc aggaagccta | 300 |
| ccggagggac | tgaaattccg | aaatatcaga | atttcaaat | gaatagcatt gaaaattact | 360 |
| aaatttgatt | ttgtttgcta | aattaaaaaa | aatccgtccg | gaagaacctc ctacaggcac | 420 |
| ccacgggtaa | taacgaaatt | tcagaaaatt | agatccgaaa | ttgtaaaccc tgatacgatg | 480 |
| ctgtgagata | tcgatcccaa | caacttcaaa | ttcagtgagg | tatatgcatt tgtggtttga | 540 |
| ttaaaggcac | gtatttcaaa | ttcagttgat | acatgaacat | gttcagagca ggtttgattt | 600 |
| ggtcataaaa | tcatcaaact | caaatgcagt | ctaggtcatg | caataaattt aaattgaatt | 660 |

-continued

```
cgtacagcaa gttaatcaaa tttgatgtgt acaagatatg tttaagtacg tgtctggtgt      720
agctagctag cgccgtggat ttgaaggaac gatgatttgg tcagtagctt gagggatctg      780
aattcttggc gtatgataaa cttgagttca aaaatacaa  gacacatcag ttttatattt      840
caattcgtgt aaaccattga attcaattca tgcaagggaa ctgaatttgc atatttcaat      900
tcatactctt agctcattta aattgacatt tgcacgatga tgagtgtgcc ttttggggt      960 ggaactggta taagtttgac ttttggggaa cttaatcaaa tccagcgtgg ttcaagcaag     1020
aaatttgaat tcaactcgta caagaaacgt attcaatttc aagctgtgca ataatgcatc     1080
tatcttaagc aaagggtctg catcatagta ctgatgcatg attgaaacag ctaagaactt     1140
gatcaaattc aatggttttt cgtgatgaaa gtttaaatcc agttcataca agaaacttat     1200
tcagattgtt tgatttaaat atgagcaaca aggcgtcgac cttaagcaaa ggttgacatc     1260
atggtgtgaa agcaaatttg aacctggcca aaacttggat cacatttgtc cagaaacttg     1320
gttcagatta acagtaatta aaataatgca accttttcac gtaagcaact actccctccg     1380
tcccataaaa aaccaaccta gtaccagatg tgacacatcc tagtattatg aatctggaca     1440
tacatatgtc cagattcatc gtactagatt atgtcacatc tagtattaga ttcgtttttt     1500
atgggacgga gggcgtatat aaaaatcgtc aatatttta  tattttttgggcacttatcaa    1560 tactatcttc aactaagaat gacgcaattg caccccaaac aaatatgctt ttttaaaact     1620
ccgggaaatg catatagaaa actgacgtca atgaatgata atgattttc  aaggccattt     1680 caaccagctg catcttttctg gcaagataat gcttgaaata attgtgcagc ttattctcaa     1740
gcgtactact actataaata gggggcata  tctgaactga gttcatatca a               1791
```

```
<210> SEQ ID NO 5
<211> LENGTH: 1993
<212> TYPE: DNA
<213> ORGANISM: Oryza sativa

<400> SEQUENCE: 5
```

```
cgttttcctt cttgaaggca tcattacttt gctctctccg tttcttcggg tgaaaacctt       60
gttccgattt tcagacggac gttgtttgcg tttcaatgct atcttcctcc ttggagactt      120
tgtcttgaag acactgcctt acgttgtctg tggtctgttc ataagaagtc ggagctgttc      180
ttttgagcta ggcaacgatg acctgtgttt taacctccag ttgtatcgtt gcaagttttt      240
agtttgttct tcatgtggat ttagcctagt tttccacaac aaaccgtgct tatgtgaggg      300
ttttggatcc ggtttccccct aaaaaactgg gccaagtctc aaaataggca ctccctatcc     360
tttttgaggt tgtcttaaaa aaaaattact aaatttgatt ttgtgtgcta aattaaaaaa     420
aatccgtccg gaagaacctc ctacagacac ccactggtaa taacgaaatt tcggaaattt     480
agatccgaaa ttgtaaaccc tgagagcaca cgcaatggta aagtaaggtg ctatctataa     540
aacatgtaca tctcagcaat agactaaatt aatagtaaac cacttcaatg gtatgtctac     600
atgggtatct atagctctct aatccattgt ctcgttttt  tctatagact atctccagat     660
tagtagatag ctttgctctc tctcttcatt taatctcttc caagtaagaa atatgctga      720 catgaatctc ttgtagagag cctatggata accattgcgg gtgccctaat acgatgccgt     780
gcgatatcga tccaacaat  acttcaaatt cagtgaggta tatgtattcg tgaagaagat     840
gatccgatcg actacttcag tgatgtgtat ttagttgttt gattaaaggc aacgtatttc     900
aaatttagtt aatacatgaa catgttcaga gcaggtttga tttggtcata gaatcatcaa     960
actcaaatgc agtctagctc atgcattaaa tttaaattga attcgtacag caagttaata    1020
```

```
gaattcgatg tgtacaagat aagtttaagt acgtgtctgg tgtagctcgc gccatggatt      1080
tgaaggaggg atgatttggt cagtagcttg agggatttga attcttggcg tatgataaac      1140
ttaagttcaa aaatataag acacatcagt tttatatttc aattcgtgta aaccactgaa       1200
ttcaattctt gcaagaaatc tgaatttgca tatttcaatt catactctta gctcattcaa      1260
attgacattt gcacgatgat gagtgtgcct tttggggtgg aactggtata agtttgactt      1320
ttggggaatt taatctaatc cagcgtggtt caagcaagaa atttgaattc aactcgtaca      1380
agaaacgtat tcaatttcaa gctgtgcaat aatgcatcta tcttaagcaa agagtctgca      1440
tcatagtaca gatgcaagat tgaaacagct aagaacttta tcaaattctg ttttcgtga       1500 tgaaagttta atccagttc atacaaattc agattgtttg ctttaaatat gagcaacaat       1560
tcgtctatct taagcaaagg ttgacatcat ggtgtgaaag caaatttgaa cctggccaaa      1620
acttggatta catttgccca gaaacttggt tcagattaac agtaattaaa ataatgcaac      1680
cgtggtgcgt aagcaactac ataaaaatcg tcaatatttt tatattttc ggcacttatc       1740 aatactatat tcaactagga atgacacaat tgcaccccaa acaaatatgc ttttttaaaa      1800
ctccaagaaa tgcatataga aaactgacgt caatgaatga taatgatttt tcaaggccat      1860
ttcaaccagc tacatctttc tggcaagata atgctttgac ataattccgc agcttttct       1920 caagggtact actactataa ataggagggc atatctgaac tgagttcata tcaagctttc      1980
aatctctcat ttc                                                         1993

<210> SEQ ID NO 6
<211> LENGTH: 1791
<212> TYPE: DNA
<213> ORGANISM: Oryza sativa

<400> SEQUENCE: 6
gccatccagt gtgatgggtt caatcactgt atgtttggct gtgtgaatta ctggtcatca       60
tcttgccagt gtgccctgtg taatgttgtt cagtgaaata taagatggct tgtttatgaa      120
ttttcctctc tcattatctc ttgttttttac cattctatgg tagaaattac agattcccat      180
tgcttggtca gatggctgct ttacctgatc ttagcctgtt attatattag tgtggtctat      240
gtgtatttct aaattctgtt catttgacct gaaattttca cgctaccatc aggaagccta      300
ccggagggac tgaaattccg aaatatcaga aatttcaaat gaatagcatt gaaaattact      360
aaatttgatt ttgtttgcta aattaaaaaa aatccgtccg gaagaacctc ctacaggcac      420
ccacgggtaa taacgaaatt tcagaaaatt agatctgaaa ttgtaaaccc tgatacgatg      480
ctgtgagata tcgatcccaa caacttcaaa ttcagtgagg tatatgtatt tgtggtttga      540
ttaaaggcac gtatttcaaa ttcagttgat acatgaacat gttcagagca ggtttgatttt     600 ggtcataaaa tcatcaaact caaatgcagt ctaggtcatg caataaattt aaattgaatt      660
cgtacagcaa gttaatcaaa tttgatgtgt acaagatatg tttaagtacg tgtctggtgt      720
agctagctag cgccgtggat ttgaaggaac gatgatttgg tcagtagctt gagggatctg      780
aattcttggc gtatgataaa cttgagttca aaaaatacaa gacacatcag ttttatattt      840
caattcgtgt aaaccattga attcaattca tgcaagggaa ctgaatttgc atatttcaat      900
tcatactctt agctcattta aattgacatt tgcacgatga tgagtgtgcc ttttgggggt      960
ggaactggta aagtttgac ttttggggaa cttaatcaaa tccagcgtgg ttcaagcaag      1020
aaatttgaat tcaactcata caagaaacgt attcaatttc aagctgtgca ataatgcatc      1080
tatcttaagc aaagggtctg catcatagta ctgatgcatg attgaaacag ctaagaactt      1140
```

-continued

```
gatcaaattc aacggttttt cgtgatgaaa gtttaaatcc agttcataca agaaacttat      1200
tcagattgtt tgatttaaat atgagcaaca aggcgtcgac cttaagcaaa ggttgacatc      1260
atggtgtgaa agcaaatttg aacctggcca aacttggat cacatttgtc cagaaacttg       1320
gttcagatta acagtaatta aaataatgca acctttgcac gtaagcaact actccctccg      1380
ttccataaaa aaccaatcta gtaccagatg tgacacatcc tagtattatg aatctggaca      1440
tacatatgtc cagattcatc gtactagatt atgtcacatc tagtattaga ttcgtttttt      1500
atgggacgga gggcgtatat aaaaatcgtc aatattttta tattttaggg cacttatcaa      1560
tactatcttc aactaagaat gacgcaattg caccccaaac aaatatgctt ttttaaaact      1620
ccgggaaatg catatagaaa actgacgtca atgaatgata atgattttc aaggccattt       1680 caaccagcta catcttctg gcatgataat gcttgaaata attgtgcagc ttattctcaa       1740
gcgtactact actataaata gggggcata tctgaactga gttcatatca a                1791
```

<210> SEQ ID NO 7
<211> LENGTH: 1991
<212> TYPE: DNA
<213> ORGANISM: Oryza sativa

<400> SEQUENCE: 7

```
cgttttcctt cttgaaggca tcattacttt gctctccccg tttcttcggg tgaaaacctt        60
gttccgattt tcagacggat gttgtttgcg tttcaatgct atcttcctcc ttggagactt       120
tgtcttgaag acactgcctt acgttgtctg tggtctgttc ataagaagtc ggagctgttc       180
ttttgagcta ggcaacgatg acctgtgttt taacctccag ttgtatcgtt gcaagttttt       240
agtttgttct tcatgtgaat ttagcctagt ttttccacaac aaaccgtgat tatgtgaggg       300
ttttggatcc ggtttcccct caaaaactgg gccaagtctc aaaataggca ctccctatcc      360
tttttgaggt tgtcttaaaa aaaaattact aaatttgatt ttgtgtgcta aattaaaaaa      420
aatccgtccg gaagaacctc ctacagacac ccactggtaa taacgaaatt tcggaaattt      480
agatccgaaa ttgtaaaccc tgagagcacc cgcaatggta agtaaggtg ctatctataa       540 aacatgtaca tctcagcaat agactaaatt aatagtaaac cacttcaatg gtatgtctac      600
atgggtatct atagctctct aatccattgc ctcgtttttt tctatagact atctccagat      660
tagtagatag ctttgctctc tctcttcatt taatctcttc caagtagaaa aatatgctga      720
catggatctc ttgtagagag cctatagata accattgcgg gtgccctaat acgatgccgt      780
gcgatatcga tcccaacaat acttcaaatt cagtgaggta tatgtattcg tgaagagatg      840
atccgatcga ctacttcagt gatgtgtatt tagttgtttg attaaaggca acgtatttca      900
aatttagtta atacatgaac atgttcagag caggtttgat ttggtcatag aatcatcaaa      960
ctcaaatgca gtctagctca tgcattaaat ttaaattgaa ttcgtacagc aagttaatag     1020
aattcgatgt gtacaagata agtttaagta cgtgtctggt gtagctcgcg ccatggattt     1080
gaaggaggga tgatttggtc agtagcttga gggatttgaa ttcttggcgt atgataaact     1140
taagttcaaa aaatataaga cacatcagtt ttatatttca attcgtgtaa accactgaat     1200
tcaattcttg caagaaatct gaatttgcat atttcaattc atactcttag ctcattcaaa     1260
ttgacatttg cacgatgatg agtgtgcctt ttggggtgga actggtataa gtttgactttt    1320 tggggaattt aatctaatcc agcgtggttc aagcaagaaa tttgaattca actcgtacaa     1380
gaaacgtatt caattttcaag ctgtgcaata atgcatctat cttaagcaaa gagtctgcat    1440
catagtacag atgcaagatt gaaacagcta agaacttat caaattctgt ttttcgtgat      1500
```

-continued

| | |
|---|---|
| gaaagtttaa atccagttca tacaaattca gattgtttgc tttaaatatg agcaacaatt | 1560 |
| cgtctatctt aagcaaaggt tgacatcatg gtgtgaaagc aaatttgaac ctggccaaaa | 1620 |
| cttggattac attttgcccag aaacttggtt cagattaaca gtaattaaaa taatgcaacc | 1680 |
| gtggtgcgta agcaactaca taaaaatcgt caatatttt atatttttcg gcacttatca | 1740 |
| atactatatt caactaggaa tgacacaatt gcaccccaaa caaatatgct ttttttaaaac | 1800 |
| tccaagaaat gcatatagaa aactgacgtc aatgaatgat aatgattttt caaggccatt | 1860 |
| tcaaccagct acatctttct ggcaagataa tgcttgacat aattccgcag cttcttctca | 1920 |
| agggtactac tactataaat aggagggcat atctgaactg agttcatatc aagctttcaa | 1980 |
| tctctcattt c | 1991 |

<210> SEQ ID NO 8
<211> LENGTH: 271
<212> TYPE: DNA
<213> ORGANISM: Oryza sativa

<400> SEQUENCE: 8

| | |
|---|---|
| cgtatataaa aatcgtcaat attttatat tttagggcac ttatcaatac tatcttcaac | 60 |
| taagaatgac gcaattgcac cccaaacaaa tatgcttttt taaaactccg ggaaatgcat | 120 |
| atagaaaact gacgtcaatg aatgataatg attttttcaag gccatttcaa ccagctacat | 180 |
| ctttctggca tgataatgct tgaaataatt gtgcagctta ttctcaagcg tactactact | 240 |
| ataaataggg gggcatatct gaactgagtt c | 271 |

<210> SEQ ID NO 9
<211> LENGTH: 1667
<212> TYPE: DNA
<213> ORGANISM: Oryza sativa

<400> SEQUENCE: 9

| | |
|---|---|
| gaattttcct ctctcattat ctcttgtttt taccattcta tggtagaaat tacagattcc | 60 |
| cattgcttgg tcagatggct gctttacctg atcttagcct gttattatat tagtgtggtc | 120 |
| tatgtgtatt tctaaattct gttcatttga cctgaaattt tcacgctacc atcaggaagc | 180 |
| ctaccggagg gactgaaatt ccgaaatatc agaaatttca atgaatagc attgaaaatt | 240 |
| actaaatttg atttttgtttg ctaaattaaa aaaaatccgt ccggaagaac ctcctacagg | 300 |
| cacccacggg taataacgaa atttcagaaa attagatctg aaattgtaaa ccctgatacg | 360 |
| atgctgtgag atatcgatcc caacaacttc aaattcagtg aggtatatgt atttgtggtt | 420 |
| tgattaaagg cacgtatttc aaattcagtt gatacatgaa catgttcaga gcaggtttga | 480 |
| tttggtcata aaatcatcaa actcaaatgc agtctaggtc atgcaataaa tttaaattga | 540 |
| attcgtacag caagttaatc aaatttgatg tgtacaagat atgtttaagt acgtgtctgg | 600 |
| tgtagctagc tagcgccgtg gatttgaagg aacgatgatt tggtcagtag cttgagggat | 660 |
| ctgaattctt ggcgtatgat aaacttgagt tcaaaaaata caagacacat cagttttata | 720 |
| tttcaattcg tgtaaaccat tgaattcaat tcatgcaagg gaactgaatt tgcatatttc | 780 |
| aattcatact cttagctcat ttaaattgac atttgcacga tgatgagtgt gcctttttggg | 840 |
| ggtggaactg gtataagttt gacttttggg gaacttaatc aaatccagcg tggttcaagc | 900 |
| aagaaatttg aattcaactc atacaagaaa cgtattcaat ttcaagctgt gcaataatgc | 960 |
| atctatctta agcaaagggt ctgcatcata gtactgatgc atgattgaaa cagctaagaa | 1020 |
| cttgatcaaa ttcaacggtt tttcgtgatg aaagtttaaa tccagttcat acaagaaact | 1080 |

| | |
|---|---|
| tattcagatt gtttgattta aatatgagca acaaggcgtc gaccttaagc aaaggttgac | 1140 |
| atcatggtgt gaaagcaaat ttgaacctgg ccaaaacttg gatcacattt gtccagaaac | 1200 |
| ttggttcaga ttaacagtaa ttaaaataat gcaacctttg cacgtaagca actactccct | 1260 |
| ccgttccata aaaaaccaat ctagtaccag atgtgacaca tcctagtatt atgaatctgg | 1320 |
| acatacatat gtccagattc atcgtactag attatgtcac atctagtatt agattcgttt | 1380 |
| tttatgggac ggagggcgta tataaaaatc gtcaatattt ttatatttta gggcacttat | 1440 |
| caatactatc ttcaactaag aatgacgcaa ttgcaccccca aacaaatatg ctttttttaaa | 1500 |
| actccgggaa atgcatatag aaaactgacg tcaatgaatg ataatgattt ttcaaggcca | 1560 |
| tttcaaccag ctacatcttt ctggcatgat aatgcttgaa ataattgtgc agcttattct | 1620 |
| caagcgtact actactataa atagggggggc atatctgaac tgagttc | 1667 |

<210> SEQ ID NO 10
<211> LENGTH: 1667
<212> TYPE: DNA
<213> ORGANISM: Oryza sativa

<400> SEQUENCE: 10

| | |
|---|---|
| gaattttcct ctctcattat ctcttgtttt taccattcta tggtagaaat tacagattcc | 60 |
| cattgcttgg tcagatggct gctttacctg atcttagcct gttattatat tagtgtggtc | 120 |
| tatgtgtatt tctaaattct gttcatttga cctgaaattt tcacgctacc atcaggaagc | 180 |
| ctaccggagg gactgaaatt ccgaaatatc agaaatttca aatgaatagc attgaaaatt | 240 |
| actaaatttg attttgtttg ctaaattaaa aaaaatccgt ccggaagaac ctcctacagg | 300 |
| cacccacggg taataacgaa atttcagaaa attagatctg aaattgtaaa ccctgatacg | 360 |
| atgctgtgag atatcgatcc caacaacttc aaattcagtg aggtatatgt atttgtggtt | 420 |
| tgattaaagg cacgtatttc aaattcagtt gatacatgaa catgttcaga gcaggtttga | 480 |
| tttggtcata aaatcatcaa actcaaatgc agtctaggtc atgcaataaa tttaaattga | 540 |
| attcgtacag caagttaatc aaatttgatg tgtacaagat atgtttaagt acgtgtctgg | 600 |
| tgtagctagc tagcgccgtg gatttgaagg aacgatgatt tggtcagtag cttgagggat | 660 |
| ctgaattctt ggcgtatgat aaacttgagc tcaaaaaata caagacacat cagttttata | 720 |
| tttcaattcg tgtaaaccat tgaattcaat tcatgcaagg gaactgaatt tgcatatttc | 780 |
| aattcatact cttagctcat ttaaattgac atttgcacga tgatgagtgt gccttttggg | 840 |
| ggtggaactg gtataagttt gacttttggg gaacttaatc aaatccagcg tggttcaagc | 900 |
| aagaaatttg aattcaactc atacaagaaa cgtattcaat ttcaagctgt gcaataatgc | 960 |
| atctatctta agcaaagggt ctgcatcata gtactgatgc atgattgaaa cagctaagaa | 1020 |
| cttgatcaaa ttcaacggtt tttcgtgatg aaagtttaaa tccagttcat acaagaaact | 1080 |
| tattcagatt gtttgattta aatatgagca acaaggcgtc gaccttaagc aaaggttgac | 1140 |
| atcatggtgt gaaagcaaat ttgaacctgg ccaaaacttg gatcacattt gtccagaaac | 1200 |
| ttggttcaga ttaacagtaa ttaaaataat gcaacctttg cacgtaagca actactccct | 1260 |
| ccgttccata aaaaaccaat ctagtaccag atgtgacaca tcctagtatt atgaatctgg | 1320 |
| acatacatat gtccagattc atcgtactag attatgtcac atctagtatt agattcgttt | 1380 |
| tttatgggac ggagggcgta tataaaaatc gtcaatattt ttatatttta gggcacttat | 1440 |
| caatactatc ttcaactaag aatgacgcaa ttgcaccccca aacaaatatg ctttttttaaa | 1500 |
| actccgggaa atgcatatag aaaactgacg tcaatgaatg ataatgattt ttcaaggcca | 1560 |

```
tttcaaccag ctacatcttt ctggcatgat aatgcttgaa ataattgtgc agcttattct   1620
caagcgtact actactataa atagggggc atatctgaac tgagttc                 1667

<210> SEQ ID NO 11
<211> LENGTH: 347
<212> TYPE: DNA
<213> ORGANISM: Oryza sativa

<400> SEQUENCE: 11
ccgtatataa aaatcgtcaa tattttata ttttagggca cttatcaata ctatcttcaa     60
ctaagaatga cgcaattgca ccccaaacaa atatgctttt ttaaaactcc gggaaatgca   120
tatagaaaac tgacgtcaat gaatgataat gattttcaa ggccatttca accagctaca   180
tctttctggc atgataatgc ttgaaataat tgtgcagctt attctcaagc gtactactac   240
tataaatagg ggggcatatc tgaactgagt tcatatcaag ctttcaatct ctcatttcat   300
ccaactatac aagttcaaga gtttacaaga gacccagacg atcaagg                 347

<210> SEQ ID NO 12
<211> LENGTH: 1751
<212> TYPE: DNA
<213> ORGANISM: Oryza sativa

<400> SEQUENCE: 12
ggatccgaat tttcctctct cattatctct tgtttttacc attctatggt agaaattaca    60
gattcccatt gcttggtcag atggctgctt tacctgatct tagcctgtta ttatattagt   120
gtggtctatg tgtatttcta aattctgttc atttgacctg aaattttcac gctaccatca   180
ggaagcctac cggagggact gaaattccga aatatcagaa atttcaaatg aatagcattg   240
aaaattacta aatttgattt tgtttgctaa attaaaaaaa atccgtccgg aagaacctcc   300
tacaggcacc cacgggtaat aacgaaattt cagaaaatta gatctgaaat tgtaaaccct   360
gatacgatgc tgtgagatat cgatcccaac aacttcaaat tcagtgaggt atatgtattt   420
gtggtttgat taaaggcacg tatttcaaat tcagttgata catgaacatg ttcagagcag   480
gtttgatttg gtcataaaat catcaaactc aaatgcagtc taggtcatgc aataaattta   540
aattgaattc gtacagcaag ttaatcaaat ttgatgtgta caagatatgt ttaagtacgt   600
gtctggtgta gctagctagc gccgtggatt tgaaggaacg atgatttggt cagtagcttg   660
agggatctga attcttggcg tatgataaac ttgagttcaa aaaatacaag acacatcagt   720
tttatatttc aattcgtgta aaccattgaa ttcaattcat gcaagggaac tgaatttgca   780
tatttcaatt catactctta gctcatttaa attgacattt gcacgatgat gagtgtgcct   840 tttggggggtg gaactggtat aagtttgact tttggggaac ttaatcaaat ccagcgtggt   900
tcaagcaaga aatttgaatt caactcatac aagaaacgta ttcaatttca agctgtgcaa   960
taatgcatct atcttaagca aagggtctgc atcatagtac tgatgcatga ttgaaacagc  1020
taagaacttg atcaaattca acggttttc gtgatgaaag tttaaatcca gttcatacaa  1080
gaaacttatt cagattgttt gatttaaata tgagcaacaa ggcgtcgacc ttaagcaaag  1140
gttgacatca tggtgtgaaa gcaaatttga acctggccaa aacttggatc acatttgtcc  1200
agaaacttgg ttcagattaa cagtaattaa aataatgcaa cctttgcacg taagcaacta  1260
ctccctccgt tccataaaaa accaatctag taccagatgt gacacatcct agtattatga  1320
atctggacat acatatgtcc agattcatcg tactagatta tgtcacatct agtattagat  1380
tcgtttttta tgggacggag ggcgtatata aaaatcgtca atatttttat attttagggc  1440
```

| acttatcaat actatcttca actaagaatg acgcaattgc accccaaaca aatatgcttt | 1500 |
| tttaaaactc cgggaaatgc atatagaaaa ctgacgtcaa tgaatgataa tgatttttca | 1560 |
| aggccatttc aaccagctac atctttctgg catgataatg cttgaaataa ttgtgcagct | 1620 |
| tattctcaag cgtactacta ctataaatag ggggcatat ctgaactgag ttcatatcaa | 1680 |
| gctttcaatc tctcatttca tccaactata caagttcaag agtttacaag agacccagac | 1740 |
| gatcaaggcc t | 1751 |

<210> SEQ ID NO 13
<211> LENGTH: 1743
<212> TYPE: DNA
<213> ORGANISM: Oryza sativa

<400> SEQUENCE: 13

| cgaattttcc tctctcatta tctcttgttt ttaccattct atggtagaaa ttacagattc | 60 |
| ccattgcttg gtcagatggc tgctttacct gatcttagcc tgttattata ttagtgtggt | 120 |
| ctatgtgtat ttctaaattc tgttcatttg acctgaaatt ttcacgctac catcaggaag | 180 |
| cctaccggag ggactgaaat tccgaaatat cagaaatttc aaatgaatag cattgaaaat | 240 |
| tactaaattt gattttgttt gctaaattaa aaaaaatccg tccggaagaa cctcctacag | 300 |
| gcacccacgg gtaataacga aatttcagaa aattagatct gaaattgtaa accctgatac | 360 |
| gatgctgtga gatatcgatc ccaacaactt caaattcagt gaggtatatg tatttgtggt | 420 |
| ttgattaaag gcacgtattt caaattcagt tgatacatga acatgttcag agcaggtttg | 480 |
| atttggtcat aaaatcatca aactcaaatg cagtctaggt catgcaataa atttaaattg | 540 |
| aattcgtaca gcaagttaat caaatttgat gtgtacaaga tatgtttaag tacgtgtctg | 600 |
| gtgtagctag ctagcgccgt ggatttgaag gaacgatgat ttggtcagta gcttgaggga | 660 |
| tctgaattct tggcgtatga taaacttgag ttcaaaaaat acaagacaca tcagtttttat | 720 |
| atttcaattc gtgtaaacca ttgaattcaa ttcatgcaag ggaactgaat ttgcatattt | 780 |
| caattcatac tcttagctca tttaaattga catttgcacg atgatgagtg tgccttttgg | 840 |
| gggtggaact ggtataagtt tgacttttgg ggaacttaat caaatccagc gtggttcaag | 900 |
| caagaaattt gaattcaact catacaagaa acgtattcaa tttcaagctg tgcaataatg | 960 |
| catctatctt aagcaaaggg tctgcatcat agtactgatg catgattgaa acagctaaga | 1020 |
| acttgatcaa attcaacggt ttttcgtgat gaaagtttaa atccagttca tacaagaaac | 1080 |
| ttattcagat tgtttgattt aaatatgagc aacaaggcgt cgaccttaag caaaggttga | 1140 |
| catcatggtg tgaaagcaaa tttgaacctg gccaaaactt ggatcacatt tgtccagaaa | 1200 |
| cttggttcag attaacagta attaaaataa tgcaacctttt gcacgtaagc aactactccc | 1260 |
| tccgttccat aaaaaaccaa tctagtacca gatgtgacac atcctagtat tatgaatctg | 1320 |
| gacatacata tgtccagatt catcgtacta gattatgtca catctagtat tagattcgtt | 1380 |
| ttttatggga cggagggcgt atataaaaat cgtcaatatt tttatatttt agggcactta | 1440 |
| tcaatactat cttcaactaa gaatgacgca attgcacccc aaacaaatat gcttttttaa | 1500 |
| aactccggga aatgcatata gaaaactgac gtcaatgaat gataatgatt tttcaaggcc | 1560 |
| atttcaacca gctacatctt tctggcatga taatgcttga ataattgtg cagcttattc | 1620 |
| tcaagcgtac tactactata aatagggggg catatctgaa ctgagttcat atcaagcttt | 1680 |
| caatctctca tttcatccaa ctatacaagt tcaagagttt acaagagacc cagacgatca | 1740 |
| agg | 1743 |

<210> SEQ ID NO 14
<211> LENGTH: 355
<212> TYPE: DNA
<213> ORGANISM: Oryza sativa

<400> SEQUENCE: 14

| | | | | | | |
|---|---|---|---|---|---|---|
| ggatcccgta | tataaaaatc | gtcaatattt | ttatatttta | gggcacttat | caatactatc | 60 |
| ttcaactaag | aatgacgcaa | ttgcacccca | aacaaatatg | cttttttaaa | actccgggaa | 120 |
| atgcatatag | aaaactgacg | tcaatgaatg | ataatgattt | ttcaaggcca | tttcaaccag | 180 |
| ctacatcttt | ctggcatgat | aatgcttgaa | ataattgtgc | agcttattct | caagcgtact | 240 |
| actactataa | atagggggggc | atatctgaac | tgagttcata | tcaagctttc | aatctctcat | 300 |
| ttcatccaac | tatacaagtt | caagagttta | caagagaccc | agacgatcaa | ggcct | 355 |

<210> SEQ ID NO 15
<211> LENGTH: 1736
<212> TYPE: DNA
<213> ORGANISM: Oryza sativa

<400> SEQUENCE: 15

| | | | | | | |
|---|---|---|---|---|---|---|
| gaattttcct | ctctcattat | ctcttgtttt | taccattcta | tggtagaaat | tacagattcc | 60 |
| cattgcttgg | tcagatggct | gctttacctg | atcttagcct | gttattatat | tagtgtggtc | 120 |
| tatgtgtatt | tctaaattct | gttcatttga | cctgaaattt | tcacgctacc | atcaggaagc | 180 |
| ctaccggagg | gactgaaatt | ccgaaatatc | agaaatttca | aatgaatagc | attgaaaatt | 240 |
| actaaatttg | attttgtttg | ctaaattaaa | aaaaatccgt | ccggaagaac | ctcctacagg | 300 |
| cacccacggg | taataacgaa | atttcagaaa | attagatctg | aaattgtaaa | ccctgatacg | 360 |
| atgctgtgag | atatcgatcc | caacaacttc | aaattcagtg | aggtatatgt | atttgtggtt | 420 |
| tgattaaagg | cacgtatttc | aaattcagtt | gatacatgaa | catgttcaga | gcaggtttga | 480 |
| tttggtcata | aaatcatcaa | actcaaatgc | agtctaggtc | atgcaataaa | tttaaattga | 540 |
| attcgtacag | caagttaatc | aaatttgatg | tgtacaagat | atgtttaagt | acgtgtctgg | 600 |
| tgtagctagc | tagcgccgtg | gatttgaagg | aacgatgatt | tggtcagtag | cttgagggat | 660 |
| ctgaattctt | ggcgtatgat | aaacttgagt | tcaaaaaata | caagacacat | cagttttata | 720 |
| tttcaattcg | tgtaaaccat | tgaattcaat | tcatgcaagg | gaactgaatt | tgcatatttc | 780 |
| aattcatact | cttagctcat | ttaaattgac | atttgcacga | tgatgagtgt | gccttttggg | 840 |
| ggtggaactg | gtataagttt | gacttttggg | gaacttaatc | aaatccagcg | tggttcaagc | 900 |
| aagaaatttg | aattcaactc | atacaagaaa | cgtattcaat | ttcaagctgt | gcaataatgc | 960 |
| atctatctta | agcaaagggt | ctgcatcata | gtactgatgc | atgattgaaa | cagctaagaa | 1020 |
| cttgatcaaa | ttcaacggtt | tttcgtgatg | aaagtttaaa | tccagttcat | acaagaaact | 1080 |
| tattcagatt | gtttgattta | aatatgagca | acaaggcgtc | gaccttaagc | aaaggttgac | 1140 |
| atcatggtgt | gaaagcaaat | ttgaacctgg | ccaaaacttg | gatcacattt | gtccagaaac | 1200 |
| ttggttcaga | ttaacagtaa | ttaaaataat | gcaacctttg | cacgtaagca | actactccct | 1260 |
| ccgttccata | aaaaaccaat | ctagtaccag | atgtgacaca | tcctagtatt | atgaatctgg | 1320 |
| acatacatat | gtccagattc | atcgtactag | attatgtcac | atctagtatt | agattcgttt | 1380 |
| tttatgggac | ggagggcgta | tataaaaatc | gtcaatattt | ttatatttta | gggcacttat | 1440 |
| caatactatc | ttcaactaag | aatgacgcaa | ttgcacccca | aacaaatatg | cttttttaaa | 1500 |
| actccgggaa | atgcatatag | aaaactgacg | tcaatgaatg | ataatgattt | ttcaaggcca | 1560 |

-continued

| | |
|---|---|
| tttcaaccag ctacatcttt ctggcatgat aatgcttgaa ataattgtgc agcttattct | 1620 |
| caagcgtact actactataa ataggggggc atatctgaac tgagttcata tcaagctttc | 1680 |
| aatctctcat tcatccaac tatacaagtt caagagttta caagagaccc agacga | 1736 |

<210> SEQ ID NO 16
<211> LENGTH: 1736
<212> TYPE: DNA
<213> ORGANISM: Oryza sativa

<400> SEQUENCE: 16

| | |
|---|---|
| gaatttcct ctctcattat ctcttgtttt taccattcta tggtagaaat tacagattcc | 60 |
| cattgcttgg tcagatggct gctttacctg atcttagcct gttattatat tagtgtggtc | 120 |
| tatgtgtatt tctaaattct gttcatttga cctgaaattt tcacgctacc atcaggaagc | 180 |
| ctaccggagg gactgaaatt ccgaaatatc agaaatttca atgaatagc attgaaaatt | 240 |
| actaaatttg attttgtttg ctaaattaaa aaaaatccgt ccggaagaac ctcctacagg | 300 |
| cacccacggg taataacgaa atttcagaaa attagatctg aaattgtaaa ccctgatacg | 360 |
| atgctgtgag atatcgatcc caacaacttc aaattcagtg aggtatatgt atttgtggtt | 420 |
| tgattaaagg cacgtatttc aaattcagtt gatacatgaa catgttcaga gcaggtttga | 480 |
| tttggtcata aaatcatcaa actcaaatgc agtctaggtc atgcaataaa tttaaattga | 540 |
| attcgtacag caagttaatc aaatttgatg tgtacaagat atgtttaagt acgtgtctgg | 600 |
| tgtagctagc tagcgccgtg gatttgaagg aacgatgatt tggtcagtag cttgagggat | 660 |
| ctgaattctt ggcgtatgat aaacttgagt tcaaaaaata caagacacat cagttttata | 720 |
| tttcaattcg tgtaaaccat tgaattcaat tcatgcaagg gaactgaatt tgcatatttc | 780 |
| aattcatact cttagctcat ttaaattgac atttgcacga tgatgagtgt gccttttggg | 840 |
| ggtggaactg gtataagttt gacttttggg gaacttaatc aaatccagcg tggttcaagc | 900 |
| aagaaatttg aattcaactc atacaagaaa cgtattcaat ttcaagctgt gcaataatgc | 960 |
| atctatctta agcaaagggt ctgcatcata gtactgatgc atgattgaaa cagctaagaa | 1020 |
| cttgatcaaa ttcaacggtt tttcgtgatg aaagtttaaa tccagttcat acaagaaact | 1080 |
| tattcagatt gtttgattta aatatgagca acaaggcgtc gaccttaagc aaaggttgac | 1140 |
| atcatggtgt gaaagcaaat ttgaacctgg ccaaaacttg gatcacattt gtccagaaac | 1200 |
| ttggttcaga ttaacagtaa ttaaaataat gcaacctttg cacgtaagca actactccct | 1260 |
| ccgttccata aaaaaccaat ctagtaccag atgtgacaca tcctagtatt atgaatctgg | 1320 |
| acatacatat gtccagattc atcgtactag attatgtcac atctagtatt agattcgttt | 1380 |
| tttatgggac ggagggcgta tataaaaatc gtcaatattt ttatatttta gggcacttat | 1440 |
| caatactatc ttcaactaag aatgacgcaa ttgcaccccca aacaaatatg cttttttaaa | 1500 |
| actccgggaa atgcatatag aaaactgacg tcaatgaatg ataatgattt ttcaaggcca | 1560 |
| tttcaaccag ctacatcttt ctggcatgat aatgcttgaa ataattgtgc agcttattct | 1620 |
| caagcgtact actactataa ataggggggc atatctgaac tgagttcata tcaagctttc | 1680 |
| aatcgctcat tcatccaac tatacaagtt caagagttta caagagaccc agacga | 1736 |

<210> SEQ ID NO 17
<211> LENGTH: 350
<212> TYPE: DNA
<213> ORGANISM: Oryza sativa

<400> SEQUENCE: 17

```
ccgtatataa aaatcgtcaa tatttttata ttttagggca cttatcaata ctatcttcaa      60
ctaagaatga cgcaattgca ccccaaacaa atatgctttt ttaaaactcc gggaaatgca     120
tatagaaaac tgacgtcaat gaatgataat gatttttcaa ggccatttca accagctaca     180
tctttctggc atgataatgc ttgaaataat tgtgcagctt attctcaagc gtactactac     240
tataaatagg ggggcatatc tgaactgagt tcatatcaag ctttcaatct ctcatttcat     300
ccaactatac aagttcctga agagtttaca agagacccag acgatcaagg                350

<210> SEQ ID NO 18
<211> LENGTH: 350
<212> TYPE: DNA
<213> ORGANISM: Oryza sativa

<400> SEQUENCE: 18
ccgtatataa aaatcgtcaa tatttttata ttttagggca cttatcaata ctatcttcaa      60
ctaagaatga cgcaattgca ccccaaacaa atatgctttt ttaaaactcc gggaaatgca     120
tatagaaaac tgacgtcaat gaatgataat gatttttcaa ggccatttca accagctaca     180
tctttctggc atgataatgc ttgaaataat tgtgcagctt attctcaagc gtactactac     240
tataaatagg ggggcatatc tgaactgagt tcatatcaag ctttcaatct ctcatttcat     300
ccaactacac aagttcctga agagtttaca agagacccag acgatcaagg                350
```

RICE METALLOTHIONEIN PROMOTERS

This application is a Continuation-In-Part of U.S. patent application Ser. No. 11/595,983, filed 13 Nov. 2006 now U.S. Pat. No. 7,790,958, which is a Division of 09/815,264 filed on 23 Mar. 2001 now U.S. Pat. No. 7,365,185, which is a Continuation-in-part of 09/702,134 filed on 31 Oct., 2000 now abandoned, which itself is a Continuation-in-part of 09/620,392 filed on 19 Jul. 2000 now abandoned, all of which are herein incorporated by reference in their entireties.

INCORPORATION OF SEQUENCE LISTING

A sequence listing containing the file named pa_01301.txt, which is 32,247 bytes (as measured in MICROSOFT WINDOWS®) and created on Aug. 2, 2007, is herein incorporated by reference in its entirety.

FIELD OF THE INVENTION

The present invention relates to the field of plant molecular biology and plant genetic engineering, and polynucleotide molecules useful for gene expression in plants. Specifically, the present invention discloses nucleic acid sequences from *Oryza sativa* (rice) comprising regulatory elements, such as promoters, leaders and introns, identified from the metallothionein (MTH) gene. The invention further discloses constructs, cells and plants comprising said regulatory elements, and methods of producing and using the same.

BACKGROUND

One of the goals of plant genetic engineering is to produce plants with agronomically desirable characteristics or traits. The proper expression of a desirable transgene in a transgenic plant is one way to achieve this goal. Elements having gene regulatory activity, i.e. regulatory elements such as promoters, leaders, introns and transcription termination regions, are non-coding polynucleotide molecules which play an integral part in the overall expression of genes in living cells. Isolated regulatory elements that function in plants are therefore useful for modifying plant phenotypes through the methods of genetic engineering.

Many regulatory elements are available and are useful for providing good overall gene expression. For example, constitutive promoters such as P-FMV, the promoter from the 35S transcript of the Figwort mosaic virus (U.S. Pat. No. 6,051,753); P-CaMV 35S, the promoter from the 35S RNA transcript of the Cauliflower mosaic virus (U.S. Pat. No. 5,530,196); P-Corn Actin 1, the promoter from the actin 1 gene of *Oryza sativa* (U.S. Pat. No. 5,641,876); and P-NO:S, the promoter from the nopaline synthase gene of *Agrobacterium tumefaciens* are known to provide some level of gene expression in most or all of the tissues of a plant during most or all of the plant's lifespan. While previous work has provided a number of regulatory elements useful to affect gene expression in transgenic plants, there is still a great need for novel regulatory elements with beneficial expression characteristics. Many previously identified regulatory elements fail to provide the patterns or levels of expression required to fully realize the benefits of expression of selected genes in transgenic crop plants. One example of this is the need for regulatory elements capable of driving gene expression in different types of tissues.

The genetic enhancement of plants and seeds provides significant benefits to society. For example, plants and seeds may be enhanced to have desirable agricultural, biosynthetic, commercial, chemical, insecticidal, industrial, nutritional, or pharmaceutical properties. Despite the availability of many molecular tools, however, the genetic modification of plants and seeds is often constrained by an insufficient or poorly localized expression of the engineered transgene.

Many intracellular processes may impact overall transgene expression, including transcription, translation, protein assembly and folding, methylation, phosphorylation, transport, and proteolysis. Intervention in one or more of these processes can increase the amount of transgene expression in genetically engineered plants and seeds. For example, raising the steady-state level of mRNA in the cytosol often yields an increased accumulation of transgene expression. Many factors may contribute to increasing the steady-state level of an mRNA in the cytosol, including the rate of transcription, promoter strength and other regulatory features of the promoter, efficiency of mRNA processing, and the overall stability of the mRNA.

Among these factors, the promoter plays a central role. Along the promoter, the transcription machinery is assembled and transcription is initiated. This early step is often rate-limiting relative to subsequent stages of protein production. Transcription initiation at the promoter may be regulated in several ways. For example, a promoter may be induced by the presence of a particular compound or external stimuli, express a gene only in a specific tissue, express a gene during a specific stage of development, or constitutively express a gene. Thus, transcription of a transgene may be regulated by operably linking the coding sequence to promoters with different regulatory characteristics. Accordingly, regulatory elements such as promoters, play a pivotal role in enhancing the agronomic, pharmaceutical or nutritional value of crops.

At least two types of information are useful in predicting promoter regions within a genomic DNA sequence. First, promoters may be identified on the basis of their sequence "content", such as transcription factor binding sites and various known promoter motifs. (Stormo, Genome Research 10: 394-397 (2000)). Such signals may be identified by computer programs that identify sites associated with promoters, such as TATA boxes and transcription factor (TF) binding sites. Second, promoters may be identified on the basis of their "location", i.e. their proximity to a known or suspected coding sequence. (Stormo, Genome Research 10: 394-397 (2000)). Promoters are typically contained within a region of DNA extending approximately 150-1500 basepairs in the 5' direction from the start codon of a coding sequence. Thus, promoter regions may be identified by locating the start codon of a coding sequence, and moving beyond the start codon in the 5' direction to locate the promoter region.

It is of immense social, ecological and economic interests to develop plants that have enhanced nutrition, improved resistance to pests, and tolerance to harsh conditions such as drought. Thus, the identification of new genes, regulatory elements (e.g., promoters), etc. that function in various types of plants is useful in developing enhanced varieties of crops. Clearly, there exists a need in the art for new regulatory elements, such as promoters, that are capable of expressing heterologous nucleic acid sequences in important crop species. We found that isolated regulatory elements from the *Oryza sativa* metallothionein gene, particularly the promoter, leader, and enhancer regulatory elements, provide these enhanced expression patterns for an operably linked transgene in a transgenic plant. Promoters that exhibit both constitutive expression and tissue-specific patterns are of great interest in the development of plants that exhibit agronomically desirable traits.

SUMMARY

The present invention describes the composition and utility for non-coding regulatory element promoter molecules identified from the *Oryza sativa* (rice) metallothionein, also known as MTH.

The present invention includes and provides a substantially purified nucleic acid molecule, or a DNA construct useful for modulating gene expression in plant cells, or a transgenic plant cell, or a transgenic plant, or a fertile transgenic plant, or a seed of a fertile transgenic plant, comprising a nucleic acid sequence wherein the nucleic acid sequence: i) hybridizes under stringent conditions with a sequence elected from the group consisting of SEQ ID NO: 1 through SEQ ID NO: 18 or any complements thereof, or any fragments thereof, or any cis elements thereof, or ii) exhibits an 85% or greater identity to a sequence elected from the group consisting of SEQ ID NO: 1 through SEQ ID NO: 18, or any complements thereof, or any fragments thereof, or any cis elements thereof.

The present invention includes and provides a method of transforming a host cell comprising: a) providing a nucleic acid molecule that comprises in the 5' to 3' direction: a nucleic acid sequence that: i) hybridizing under stringent conditions with a sequence selected from the group consisting of SEQ ID NO: 1 through SEQ ID NO: 18, or any complements thereof, or any fragments thereof, or any cis elements thereof, or ii) exhibiting an 85% or greater identity to a sequences elected from the group consisting SEQ ID NO: 1 through SEQ ID NO: 18, or any complements thereof, or any fragments thereof, or any cis elements thereof, operably linked to a transcribable polynucleotide molecule sequence; and b) transforming said plant with the nucleic acid molecule.

In one embodiment, the invention provides regulatory elements isolated from *Oryza sativa* and useful for modulating gene expression in transgenic plants In another embodiment, the invention provides DNA constructs containing polynucleotide molecules useful for modulating gene expression in plants. In another embodiment, the invention provides transgenic plants and seeds comprising the DNA constructs, comprising a promoter or other regulatory elements operably linked to a heterologous DNA molecule, useful for modulating gene expression in plants. The transgenic plant preferably expresses an agronomically desirable phenotype.

DETAILED DESCRIPTION OF THE INVENTION

Figure 1:
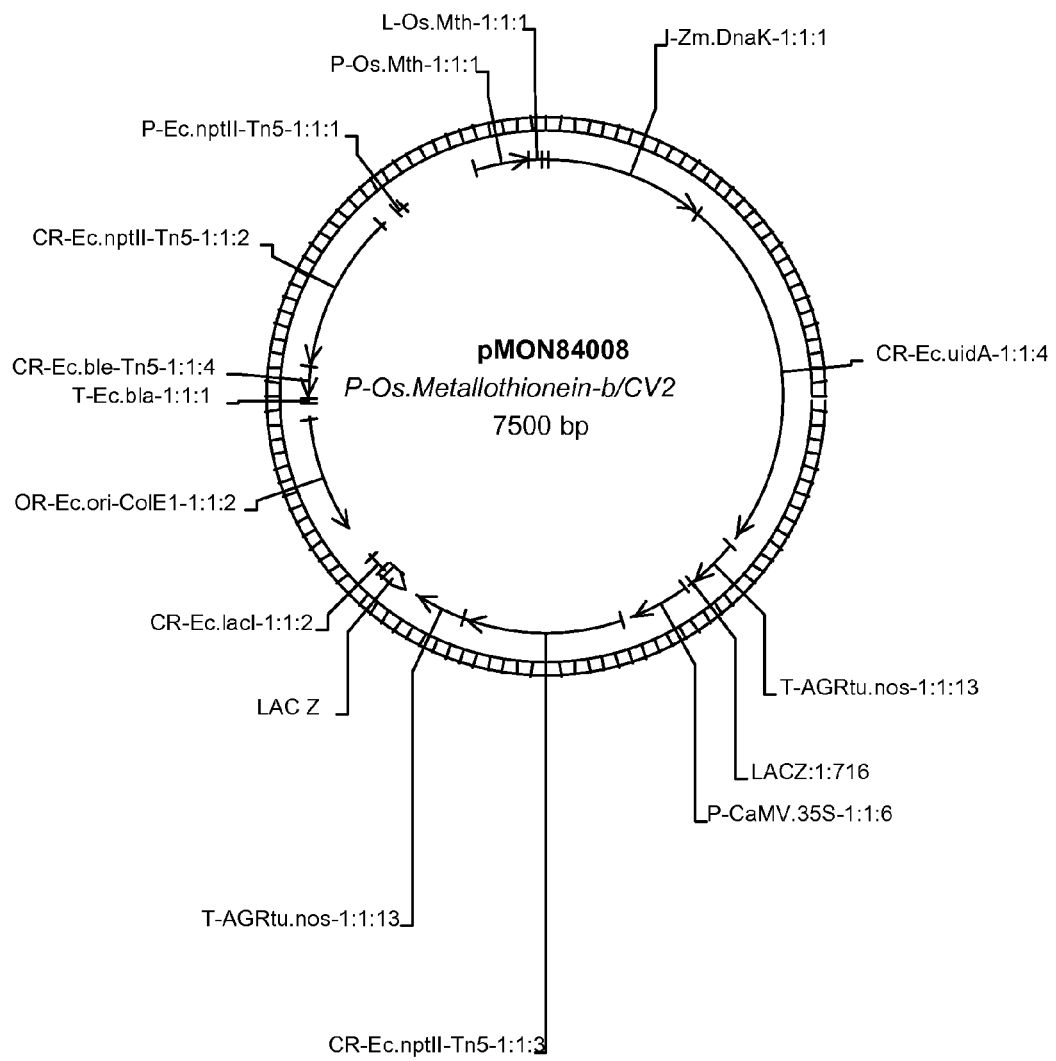
FIG. 1: pMON84008, comprising the rice metallothionein promoter P-Os.Metallothionein -b-1:1:2 (SEQ ID NO: 11)
Figure 2:
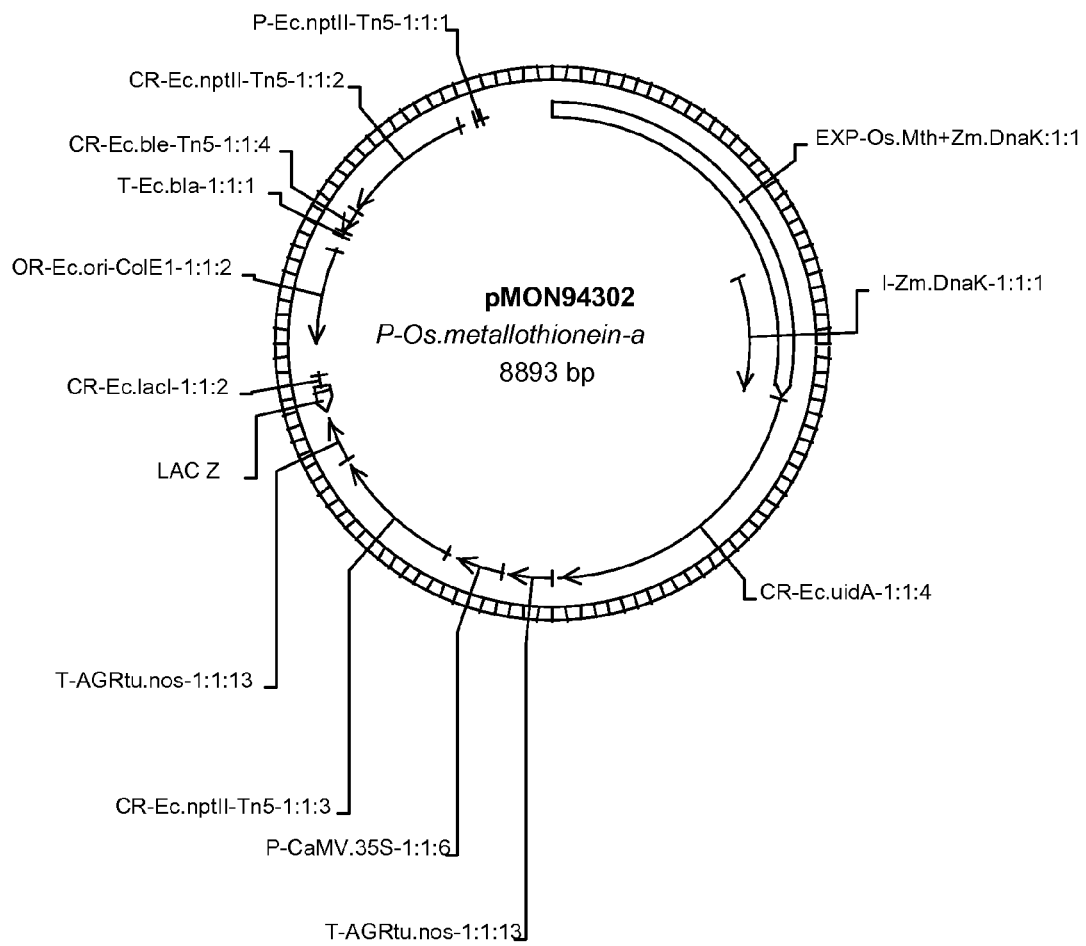
FIG. 2: pMON94302, comprising the rice metallothionein promoter P-Os.Metallothionein -a-1:1:7 (SEQ ID NO: 16).

The invention disclosed herein provides polynucleotide molecules having gene regulatory activity identified from the metallothionein (MTH) gene of *Oryza sativa*. The design, construction, and use of these polynucleotide molecules are one object of this invention. The polynucleotide sequences of these polynucleotide molecules are provided as SEQ ID NO: 1 through SEQ ID NO: 18. These polynucleotide molecules are capable of affecting the expression of an operably linked transcribable polynucleotide molecule in plant tissues and therefore can selectively regulate gene expression in transgenic plants. The present invention also provides methods of modifying, producing, and using the same. The invention also includes compositions, transformed host cells, transgenic plants, and seeds containing the promoters, and methods for preparing and using the same.

Polynucleotide Molecules

Many types of regulatory sequences control gene expression. Not all genes are turned on at all times during the life cycle of a plant. Different genes are required for the completion of different steps in the developmental and sexual maturation of the plant. Two general types of control can be described: temporal regulation, in which a gene is only expressed at a specific time in development (for example, during flowering), and spatial regulation, in which a gene is only expressed in a specific location in the plant (for example, seed storage proteins). Many genes, however, may fall into both classes. For example, seed storage proteins are only expressed in the seed, but they also are only expressed during a short period of time during the development of the seed. Furthermore, because the binding of RNA Polymerase II to the promoter is the key step in gene expression, it follows that sequences may exist in the promoter that control temporal and spatial gene expression.

The following definitions and methods are provided to better define the present invention and to guide those of ordinary skill in the art in the practice of the present invention. Unless otherwise noted, terms are to be understood according to conventional usage by those of ordinary skill in the relevant art.

The phrases "coding sequence", "structural sequence", and "transcribable polynucleotide sequence" refer to a physical structure comprising an orderly arrangement of nucleic acids. The nucleic acids are arranged in a series of nucleic acid triplets that each form a codon. Each codon encodes for a specific amino acid. Thus the coding sequence, structural sequence, and transcribable polynucleotide sequence encode a series of amino acids forming a protein, polypeptide, or peptide sequence. The coding sequence, structural sequence, and transcribable polynucleotide sequence may be contained, without limitation, within a larger nucleic acid molecule, vector, etc. In addition, the orderly arrangement of nucleic acids in these sequences may be depicted, without limitation, in the form of a sequence listing, figure, table, electronic medium, etc.

As used herein, the term "polynucleotide molecule" refers to the single- or double-stranded DNA or RNA molecule of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for nucleotide bases as set forth at 37 CFR § 1.822 is used herein.

As used herein, the term "regulatory element" refers to a polynucleotide molecule having gene regulatory activity, i.e. one that has the ability to affect the transcription or translation of an operably linked transcribable polynucleotide molecule. Regulatory elements such as promoters, leaders, introns, and transcription termination regions are polynucleotide molecules having gene regulatory activity which play an integral part in the overall expression of genes in living cells. Isolated regulatory elements that function in plants are therefore useful for modifying plant phenotypes through the methods of genetic engineering. By "regulatory element" it is intended a series of nucleotides that determines if, when, and at what level a particular gene is expressed. The regulatory DNA sequences specifically interact with regulatory proteins or other proteins.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may be part of a single contiguous polynucleotide molecule and may be adjacent. For example, a promoter is operably linked to a gene of interest if the promoter modulates transcription of the gene of interest in a cell.

As used herein, the term "gene regulatory activity" refers to a polynucleotide molecule capable of affecting transcription or translation of an operably linked polynucleotide molecule. An isolated polynucleotide molecule having gene regulatory activity may provide temporal or spatial expression or modulate levels and rates of expression of the operably linked polynucleotide molecule. An isolated polynucleotide molecule having gene regulatory activity may comprise a promoter, intron, leader, or 3' transcriptional termination region.

As used herein, the term "gene expression" or "expression" refers to the transcription of a DNA molecule into a transcribed RNA molecule. Gene expression may be described as related to temporal, spatial, developmental, or morphological qualities as well as quantitative or qualitative indications. The transcribed RNA molecule may be translated to produce a protein molecule or may provide an antisense or other regulatory RNA molecule.

As used herein, an "expression pattern" is any pattern of differential gene expression. In a preferred embodiment, an expression pattern is selected from the group consisting of tissue, temporal, spatial, developmental, stress, environmental, physiological, pathological, cell cycle, and chemically responsive expression patterns.

As used herein, an "enhanced expression pattern" is any expression pattern for which an operably linked nucleic acid sequence is expressed at a level greater than 0.01%; preferably in a range of about 0.5% to about 20% (w/w) of the total cellular RNA or protein.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule, including but not limited to protein coding sequences (e.g. transgenes) and sequences (e.g. a molecule useful for gene suppression).

The present invention includes a polynucleotide molecule having a nucleic acid sequence that hybridizes to SEQ ID NO: 1 through SEQ ID NO: 18, or any complements thereof, or any cis elements thereof, or any fragments thereof. The present invention also provides a nucleic acid molecule comprising a nucleic acid sequence selected from the group consisting of SEQ ID NO: 1 through SEQ ID NO: 18, any complements thereof, or any cis elements thereof, or any fragments thereof. The polynucleotide molecules of the present invention (SEQ ID NO: 1 through SEQ ID NO: 18) were all isolated or identified from the *Oryza sativa* metallothionein (MTH) gene, and are represented in the polynucleotide constructs listed in Table 1.

TABLE 1

Sequence Annotations for Polynucleotide Molecules
Isolated from the MTH gene of *Oryza sativa*

| SEQ ID | Description |
|---|---|
| 1 | 51237G_55999 |
| 2 | P-Os.Mth1-1:1:1 |
| 3 | P-Os.Mth2-1:1:1 |
| 4 | P-Os.Mth1-1:1:2 |
| 5 | P-Os.Mth2-1:1:2 |
| 6 | P-Os.Mth1-1:1:3 |
| 7 | P-Os.Mth2-1:1:5 |
| 8 | P-Os.Mth-1:1:1 |
| 9 | P-Os.Mth-1:1:2 |
| 10 | P-Os.Mth-1:1:3 |
| 11 | P-Os.Metallothionein-b-1:1:2 |
| 12 | P-Os.Metallothionein-a-1:1:1 |
| 13 | P-Os.Metallothionein-a-1:1:2 |
| 14 | P-Os.Metallothionein-b-1:1:1 |
| 15 | P-Os.Metallothionein-a-1:1:3 |
| 16 | P-Os.Metallothionein-a-1:1:7 |
| 17 | P-Os.Metallothionein-b-1:1:3 |
| 18 | P-Os.Metallothionein-b-1:1:4 |

Determination of Sequence Similarity Using Hybridization Techniques

Nucleic acid hybridization is a technique well known to those of skill in the art of DNA manipulation. The hybridization properties of a given pair of nucleic acids are an indication of their similarity or identity.

The term "hybridization" refers generally to the ability of nucleic acid molecules to join via complementary base strand pairing. Such hybridization may occur when nucleic acid molecules are contacted under appropriate conditions. "Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity", i.e., each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional low stringency and high stringency conditions are described herein and by Sambrook et al., Molecular Cloning, A Laboratory Manual, 2nd Ed., Cold Spring Harbor Press, Cold Spring Harbor, N.Y. (1989) and by Haymes et al., Nucleic Acid Hybridization, A Practical Approach, IRL Press, Washington, D.C. (1985). Departures from complete complementarity are permissible, as long as such departures do not completely preclude the capacity of the molecules to form a double-stranded structure.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL fish sperm DNA, and 0.1% (w/v) SDS, with an incubation at 55° C. for several hours. Hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1 X SSC at 65° C.

A nucleic acid molecule preferably comprises a nucleic acid sequence that hybridizes, under low or high stringency conditions, with SEQ ID NO: 1 through SEQ ID NO: 18, any complements thereof, or any fragments thereof, or any cis elements thereof A nucleic acid molecule most preferably comprises a nucleic acid sequence that hybridizes under high stringency conditions with SEQ ID NO: 1 through SEQ ID NO: 18, any complements thereof, or any fragments thereof, or any cis elements thereof.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® WISCONSIN PACKAGE® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the SEQUENCE ANALYSIS SOFTWARE PACKAGE™ (Version 10; Genetics Computer Group, Inc., Madison, Wis.). "Gap" utilizes the algorithm of Needleman and Wunsch (Needleman and Wunsch, *Journal of Molecular Biology* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Advances in Applied Mathematics,* 2:482-489, 1981, Smith et al., *Nucleic Acids Research* 11:2205-2220, 1983). The percent identity is most preferably determined using the "Best Fit" program.

Useful methods for determining sequence identity are also disclosed in Guide to Huge Computers, Martin J. Bishop, ed., Academic Press, San Diego, 1994, and Carillo, H., and Lipton, D., *Applied Math* (1988) 48:1073. More particularly, preferred computer programs for determining sequence identity include the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al, NCBI, NLM, NIH; Altschul et al., *J. Mol. Biol.* 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that are capable of regulating transcription of operably linked transcribable polynucleotide molecules and have a substantial percent sequence identity to the polynucleotide sequences of the polynucleotide molecules provided herein are encompassed within the scope of this invention.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

In an alternative embodiment, the nucleic acid molecule comprises a nucleic acid sequence that exhibits 70% or greater identity, and more preferably at least 80 or greater, 85 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid molecule selected from the group consisting of SEQ ID NO: 1 through SEQ ID NO: 18, any complements thereof, any fragments thereof, or any cis elements thereof. The nucleic acid molecule preferably comprises a nucleic acid sequence that exhibits a 75% or greater sequence identity with a polynucleotide selected from the group consisting of SEQ ID NO: 1 through SEQ ID NO: 18, any complements thereof, any fragments thereof, or any cis elements thereof. The nucleic acid molecule more preferably comprises a nucleic acid sequence that exhibits an 80% or greater sequence identity with a polynucleotide selected from the group consisting of SEQ ID NO: 1 through SEQ ID NO: 18, any complements thereof, any fragments thereof, or any cis elements thereof. The nucleic acid molecule most preferably comprises a nucleic acid sequence that exhibits an 85% or greater sequence identity with a polynucleotide selected from the group consisting of SEQ ID NO: 1 through SEQ ID NO: 18, any complements thereof, any fragments thereof, or any cis elements thereof.

For purposes of this invention "percent identity" may also be determined using BLASTX version 2.0 for translated nucleotide sequences and BLASTN version 2.0 for polynucleotide sequences. In a preferred embodiment of the present invention, the presently disclosed corn genomic promoter sequences comprise nucleic acid molecules or fragments having a BLAST score of more than 200, preferably a BLAST score of more than 300, and even more preferably a BLAST score of more than 400 with their respective homologues.

Polynucleotide Molecules, Motifs, Fragments, Chimeric Molecules

Nucleic acid molecules of the present invention include nucleic acid sequences that are between about 0.01 Kb and about 50 Kb, more preferably between about 0.1 Kb and about 25 Kb, even more preferably between about 1 Kb and about 10 Kb, and most preferably between about 3 Kb and about 10 Kb, about 3 Kb and about 7 Kb, about 4 Kb and about 6 Kb, about 2 Kb and about 4 Kb, about 2 Kb and about 5 Kb, about 1 Kb and about 5 Kb, about 1 Kb and about 3 Kb, or about 1 Kb and about 2 Kb.

As used herein, the term "fragment" or "fragment thereof" refers to a finite polynucleotide sequence length that comprises at least 25, at least 50, at least 75, at least 85, or at least 95 contiguous nucleotide bases wherein its complete sequence in entirety is identical to a contiguous component of the referenced polynucleotide molecule.

As used herein, the term "chimeric" refers to the product of the fusion of portions of two or more different polynucleotide molecules. As used herein, the term "chimeric" refers to a gene expression element produced through the manipulation of known elements or other polynucleotide molecules. Novel chimeric regulatory elements can be designed or engineered by a number of methods. In one embodiment of the present invention, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

In another embodiment of the present invention, chimeric molecules may combine enhancer domains that can confer or modulate gene expression from one or more promoters, by fusing a heterologous enhancer domain from a first promoter to a second promoter with its own partial or complete regulatory elements. Examples of suitable enhancer domains to be used in the practice of the present invention include, but are not limited to the enhancer domains from promoters such as P-FMV, the promoter from the 35S transcript of the Figwort mosaic virus (described in U.S. Pat. No. 6,051,753, which is incorporated herein by reference) and P-CaMV 35S, the promoter from the 35S RNA transcript of the Cauliflower mosaic virus (described in U.S. Pat. Nos. 5,530,196, 5,424,200, and 5,164,316, all of which are incorporated herein by reference). Construction of chimeric promoters using enhancer domains is described in, for example, U.S. Pat. No. 6,660,911, which is incorporated herein by reference. Thus, the design, construction, and use of chimeric expression elements according to the methods disclosed herein for modulating the expression of operably linked transcribable polynucleotide molecules are encompassed by the present invention.

The invention disclosed herein provides polynucleotide molecules comprising regulatory element fragments that may be used in constructing novel chimeric regulatory elements. Novel combinations comprising fragments of these polynucleotide molecules and at least one other regulatory element or fragment can be constructed and tested in plants and are considered to be within the scope of this invention. Thus, the design, construction, and use of chimeric regulatory elements is one object of this invention.

Regulatory Elements

Gene expression is finely regulated at both the transcriptional and post-transcriptional levels. A spectrum of control regions regulate transcription by RNA polymerase II. Enhancers that can stimulate transcription from a promoter tens of thousands of base pairs away (e.g., the SV40 enhancer) are an example of long-range effectors, whereas more proximal elements include promoters and introns. Transcription initiates at the cap site encoding the first nucleotide of the first exon of an mRNA. For many genes, especially those encoding abundantly expressed proteins, a TATA box located 25-30 base pairs upstream form the cap site directs RNA polymerase II to the start site. Promoter-proximal elements roughly within the first 200 base pairs upstream of the cap site stimulate transcription.

Features of the untranslated regions of mRNAs that control translation, degradation and localization include stem-loop structures, upstream initiation codons and open reading frames, internal ribosome entry sites and various cis-acting elements that are bound by RNA-binding proteins.

The present invention provides the composition and utility of molecules comprising regulatory element sequences identified from *Zea mays*. These regulatory element sequences may comprise promoters, cis-elements, enhancers, terminators, or introns. regulatory elements may be isolated or identified from UnTranslated Regions (UTRs) from a particular polynucleotide sequence. Any of the regulatory elements described herein may be present in a recombinant construct of the present invention.

One skilled in the art would know various promoters, introns, enhancers, transit peptides, targeting signal sequences, 5' and 3' untranslated regions (UTRs), as well as other molecules involved in the regulation of gene expression that are useful in the design of effective plant expression vectors, such as those disclosed, for example, in U.S. Patent Application Publication 2003/01403641 (herein incorporated by reference).

UTRs

UTRs are known to play crucial roles in the post-transcriptional regulation of gene expression, including modulation of the transport of mRNAs out of the nucleus and of translation efficiency, subcellular localization and stability. Regulation by UTRs is mediated in several ways. Nucleotide patterns or motifs located in 5' UTRs and 3' UTRs can interact with specific RNA-binding proteins. Unlike DNA-mediated regulatory signals, however, whose activity is essentially mediated by their primary structure, the biological activity of regulatory motifs at the RNA level relies on a combination of primary and secondary structure. Interactions between sequence elements located in the UTRs and specific complementary RNAs have also been shown to play key regulatory roles.

Finally, there are examples of repetitive elements that are important for regulation at the RNA level, affecting translation efficiency. For example, non-translated 5' leader polynucleotide molecules derived from heat shock protein genes have been demonstrated to enhance gene expression in plants (see for example, U.S. Pat. Nos. 5,659,122 and 5,362,865, all of which are incorporated herein by reference).

Cis-Acting Elements

Many regulatory elements act in cis ("cis elements") and are believed to affect DNA topology, producing local conformations that selectively allow or restrict access of RNA polymerase to the DNA template or that facilitate selective opening of the double helix at the site of transcriptional initiation. C is elements occur within the 5' UTR associated with a particular coding sequence, and are often found within promoters and promoter modulating sequences (inducible elements). C is elements can be identified using known cis elements as a target sequence or target motif in the BLAST programs of the present invention. Examples of cis-acting elements in the 5'UTR associated with a polynucleotide coding sequence include, but are not limited to, promoters and enhancers.

Promoters

Among the gene expression regulatory elements, the promoter plays a central role. Along the promoter, the transcription machinery is assembled and transcription is initiated. This early step is often rate-limiting relative to subsequent stages of protein production. Transcription initiation at the promoter may be regulated in several ways. For example, a promoter may be induced by the presence of a particular compound or external stimuli, express a gene only in a specific tissue, express a gene during a specific stage of development, or constitutively express a gene. Thus, transcription of a transgene may be regulated by operably linking the coding sequence to promoters with different regulatory characteristics. Accordingly, regulatory elements such as promoters, play a pivotal role in enhancing the agronomic, pharmaceutical or nutritional value of crops.

As used herein, the term "promoter" refers to a polynucleotide molecule that is involved in recognition and binding of RNA polymerase II and other proteins such as transcription factors (trans-acting protein factors that regulate transcription) to initiate transcription of an operably linked gene. A promoter may be isolated from the 5' untranslated region (5' UTR) of a genomic copy of a gene. Alternately, promoters may be synthetically produced or manipulated DNA elements. Promoters may be defined by their temporal, spatial, or developmental expression pattern. A promoter can be used as a regulatory element for modulating expression of an operably linked transcribable polynucleotide molecule. Promoters may themselves contain sub-elements such as cis-elements or enhancer domains that effect the transcription of operably linked genes. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern.

Any of the nucleic acid molecules described herein may comprise nucleic acid sequences comprising promoters. Promoters of the present invention can include between about 300 bp upstream and about 10 kb upstream of the trinucleotide ATG sequence at the start site of a protein coding region. Promoters of the present invention can preferably include between about 300 bp upstream and about 5 kb upstream of the trinucleotide ATG sequence at the start site of a protein coding region. Promoters of the present invention can more preferably include between about 300 bp upstream and about 2 kb upstream of the trinucleotide ATG sequence at the start site of a protein coding region. Promoters of the present invention can include between about 300 bp upstream and about 1 kb upstream of the trinucleotide ATG sequence at the start site of a protein coding region. While in many circumstances a 300 bp promoter may be sufficient for expression, additional sequences may act to further regulate expression, for example, in response to biochemical, developmental or environmental signals.

The promoter of the present invention preferably transcribes a heterologous transcribable polynucleotide sequence at a high level in a plant. More preferably, the promoter hybridizes to a nucleic acid sequence selected from the group consisting of SEQ ID NO: 1 through SEQ ID NO: 18, or any complements thereof, or any fragments thereof. Suitable hybridization conditions include those described above. A nucleic acid sequence of the promoter preferably hybridizes, under low or high stringency conditions, with a molecule selected from the group consisting of SEQ ID NO: 1 through SEQ ID NO: 18, complements thereof, or any fragment thereof.

In an alternative embodiment, the promoter comprises a nucleic acid sequence that exhibits 85% or greater identity, and more preferably at least 86 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid sequence selected from the group consisting of SEQ ID NO: 1 through SEQ ID NO: 18, or complements thereof. The promoter most preferably comprises a nucleic acid sequence selected from the group consisting of SEQ ID NOs: through SEQ ID NO: 18, complements thereof, or any fragments thereof.

A promoter comprises promoter fragments that have promoter activity. Promoter fragments may comprise other regulatory elements such as enhancer domains, and may further be useful for constructing chimeric molecules. The identification of the minimum length fragment that retains promoter activity is well within the skill of the art. For example, fragments of the promoters of the present invention comprise at least about 50, at least about 100, at least about 150, at least about 200, at least about 250, at least about 400, at least about 500, or at least about 750 contiguous nucleotides, up to and including the full length of each disclosed SEQ ID.

At least two types of information are useful in predicting promoter regions within a genomic DNA sequence. First, promoters may be identified on the basis of their sequence "content", such as transcription factor binding sites and various known promoter motifs. (Stormo, Genome Research 10: 394-397 (2000)). Such signals may be identified by computer programs that identify sites associated with promoters, such as TATA boxes and transcription factor (TF) binding sites. Second, promoters may be identified on the basis of their "location", i.e. their proximity to a known or suspected coding sequence. (Stormo, Genome Research 10: 394-397 (2000)). Promoters are typically found within a region of DNA extending approximately 150-1500 base pairs in the 5' direction from the start codon of a coding sequence. Thus, promoter regions may be identified by locating the start codon of a coding sequence, and moving beyond the start codon in the 5' direction to locate the promoter region.

Promoter sequence may be analyzed for the presence of common promoter sequence characteristics, such as a TATA-box and other known transcription factor binding site motifs. These motifs are not always found in every known promoter, nor are they necessary for promoter function, but when present, do indicate that a segment of DNA is a promoter sequence.

For identification of the TATA-box, the putative promoter sequences immediately upstream of the coding start site of the predicted genes within a given sequence size range, as described above, are used. The transcription start site and TATA-box (if present) may be predicted with program TSSP. TSSP is designed for predicting PolII promoter regions in plants, and is based on the discriminate analysis combing characteristics of functional elements of regulatory sequence with the regulatory motifs from Softberry Inc.'s plant RegSite database (Solovyev V.V. (2001) *Statistical approaches in Eukaryotic gene prediction*. In: Handbook of Statistical genetics (eds. Balding D. et al.), John Wiley & Sons, Ltd., p. 83-127). In the cases that multiple TATA-boxes are predicted, only the rightmost (closest to the 5' end) TATA-box is kept. The transcription start sites (TSS) are refined and extended upstream, based on the matches to the database sequences. Promoter sequences with unique TATA-box, as well the TATA-box locations, may be identified within the promoter sequences.

For identification of other known transcription factor binding motifs (such as a GC-box, CAAT-box, etc.), the promoter sequences immediately upstream of the coding start site of the predicted genes within a given sequence size range, as described above, are used. The known transcription factor binding motifs (except TATA-box) on the promoter sequences are predicted with a proprietary program PromoterScan. The identification of such motifs provide important information about the candidate promoter. For example, some motifs are associated with informative annotations such as (but not limited to) "light inducible binding site" or "stress inducible binding motif" and can be used to select with confidence a promoter that is able to confer light inducibility or stress inducibility to an operably-linked transgene, respectively.

Putative promoter sequences are also searched with matcorns for the GC box (factor name: V_GC_01) and CCAAT box (factor name: F_HAP234_01). The matcorns for the GC box and the CCAAT box are from Transfac. The algorithm that is used to annotate promoters searches for matches to both sequence motifs and matrix motifs. First, individual matches are found. For sequence motifs, a maximum number of mismatches are allowed. If the code M,R,W,S,Y, or K are listed in the sequence motif (each of which is a degenerate code for 2 nucleotides) ½ mismatch is allowed. If the code B, D, H, or V is listed in the sequence motif (each of which is a degenerate code for 3 nucleotides) ⅓ mismatch is allowed. Appropriate p values may be determined by simulation by generation of a 5 Mb length of random DNA with the same dinucleotide frequency as the test set, and from this test set the probability of a given matrix score was determined (number of hits/5e7). Once the individual hits are found, the putative promoter sequence is searched for clusters of hits in a 250 bp window. The score for a cluster is found by summing the negative natural log of the p value for each individual hit. Using simulations with 100 Mb lengths, the probability of a window having a cluster score greater than or equal to the given value is determined. Clusters with a p value more significant than p<1 e-6 are reported. Effects of repetitive elements are screened. For matrix motifs, a p value cutoff is used on a matrix score. The matrix score is determined by adding the path of a given DNA sequence through a matrix. Appropriate p values are determined by simulation: 5 Mb lengths of random DNA with the same dinucleotide frequency as a test set are generated to test individual matrix hits, and 100 Mb lengths are used to test clusters. The probability of a given matrix score and the probability scores for clusters are determined, as are the sequence motifs. The usual cutoff for matcorns is 2.5e-4. No clustering was done for the GC box or CAAT box.

Examples of promoters include: those described in U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter, P-Zm.L3), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gama-coixin promoter, P-Cl.Gcx), and U.S. patent application Ser. No. 09/757,089 (maize chloroplast aldolase promoter), all of which are incorporated herein by reference in their entirety.

Promoters of the present invention include homologues of cis elements known to effect gene regulation that show homology with the promoter sequences of the present invention. These cis elements include, but are not limited to, oxygen responsive cis elements (Cowen et al., J. Biol. Chem. 268(36):26904-26910 (1993)), light regulatory elements (Bruce and Quaill, Plant Cell 2 (11):1081-1089 (1990); Bruce et al., EMBO J. 10:3015-3024 (1991); Rocholl et al., Plant Sci. 97:189-198 (1994); Block et al., Proc. Natl. Acad. Sci. USA 87:5387-5391 (1990); Giuliano et al., Proc. Natl. Acad. Sci. USA 85:7089-7093 (1988); Staiger et al., Proc. Natl. Acad. Sci. USA 86:6930-6934 (1989); Izawa et al., Plant Cell 6:1277-1287 (1994); Menkens et al., Trends in Biochemistry 20:506-510 (1995); Foster et al., FASEB J. 8:192-200 (1994); Plesse et al., Mol Gen Gene 254:258-266 (1997); Green et al., EMBO J. 6:2543-2549 (1987); Kuhlemeier et al., Ann. Rev Plant Physiol. 38:221-257 (1987); Villain et al., J. Biol. Chem. 271:32593-32598 (1996); Lam et al., Plant Cell 2:857-866 (1990); Gilmartin et al., Plant Cell 2:369-378 (1990); Datta et al., Plant Cell 1:1069-1077 (1989); Gilmartin et al., Plant Cell 2:369-378 (1990); Castresana et al., EMBO J. 7:1929-1936 (1988); Ueda et al., Plant Cell 1:217-227 (1989); Terzaghi et al., Annu. Rev. Plant Physiol. Plant Mol. Biol. 46:445-474 (1995); Green et al., EMBO J. 6:2543-2549 (1987); Villain et al., J. Biol. Chem. 271:32593-32598 (1996); Tjaden et al., Plant Cell 6:107-118 (1994); Tjaden et al., Plant Physiol. 108:1109-1117 (1995); Ngai et al., Plant J. 12:1021-1234 (1997); Bruce et al., EMBO J. 10:3015-3024 (1991); Ngai et al., Plant J. 12:1021-1034 (1997)), elements responsive to gibberellin, (Muller et al., J. Plant Physiol. 145:606-613 (1995); Croissant et al., Plant Science 116:27-35 (1996); Lohmer et al., EMBO J. 10:617-624 (1991); Rogers et al., Plant Cell 4:1443-1451 (1992); Lanahan et al., Plant Cell 4:203-211 (1992); Skriver et al., Proc. Natl. Acad. Sci. USA 88:7266-7270 (1991); Gilmartin et al., Plant Cell 2:369-378 (1990); Huang et al., Plant Mol. Biol. 14:655-668 (1990), Gubler et al., Plant Cell 7:1879-1891 (1995)), elements responsive to abscisic acid, (Busk et al., Plant Cell 9:2261-2270 (1997); Guiltinan et al., Science 250:267-270 (1990); Shen et al., Plant Cell 7:295-307(1995); Shen et al., Plant Cell 8:1107-1119 (1996); Seo et al., Plant Mol. Biol. 27:1119-1131 (1995); Marcotte et al., Plant Cell 1:969-976 (1989); Shen et al., Plant Cell 7:295-307 (1995); Iwasaki et al., Mol Gen Genet. 247:391-398 (1995); Hattori et al., Genes Dev. 6:609-618 (1992); Thomas et al., Plant Cell 5:1401-1410 (1993)), elements similar to abscisic acid responsive elements, (Ellerstrom et al., Plant Mol. Biol. 32:1019-1027 (1996)), auxin responsive elements (Liu et al., Plant Cell 6:645-657 (1994); Liu et al., Plant Physiol. 115:397-407 (1997); Kosugi et al., Plant J. 7:877-886 (1995); Kosugi et al., Plant Cell 9:1607-1619 (1997); Ballas et al., J. Mol. Biol. 233:580-596 (1993)), a cis element responsive to methyl jasmonate treatment (Beaudoin and Rothstein, Plant Mol. Biol. 33:835-846 (1997)), a cis element responsive to abscisic acid and stress response (Straub et al., Plant Mol. Biol. 26:617-630 (1994)), ethylene responsive cis elements (Itzhaki et al., Proc. Natl. Acad. Sci. USA 91:8925-8929 (1994); Montgomery et al., Proc. Natl. Acad. Sci. USA 90:5939-5943 (1993); Sessa et al., Plant Mol. Biol. 28:145-153 (1995); Shinshi et al., Plant Mol. Biol. 27:923-932 (1995)), salicylic acid cis responsive elements, (Strange et al., Plant J. 11:1315-1324 (1997); Qin et al., Plant Cell 6:863-874 (1994)), a cis element that responds to water stress and abscisic acid (Lam et al., J. Biol. Chem. 266:17131-17135 (1991); Thomas et al., Plant Cell 5:1401-1410 (1993); Pla et al., Plant Mol Biol 21:259-266 (1993)), a cis element essential for M phase-specific expression (Ito et al., Plant Cell 10:331-341 (1998)), sucrose responsive elements (Huang et al., Plant Mol. Biol. 14:655-668 (1990); Hwang et al., Plant Mol Biol 36:331-341 (1998); Grierson et al., Plant J. 5:815-826 (1994)), heat shock response elements (Pelham et al., Trends Genet. 1:31-35 (1985)), elements responsive to auxin and/or salicylic acid and also reported for light regulation (Lam et al., Proc. Natl. Acad. Sci. USA 86:7890-7897 (1989); Benfey et al., Science 250:959-966 (1990)), elements responsive to ethylene and salicylic acid (Ohme-Takagi et al., Plant Mol. Biol. 15:941-946 (1990)), elements responsive to wounding and abiotic stress (Loake et al., Proc. Natl. Acad. Sci. USA 89:9230-9234 (1992); Mhiri et al., Plant Mol. Biol. 33:257-266 (1997)), antoxidant response elements (Rushmore et al., J. Biol. Chem. 266:11632-11639; Dalton et al., Nucleic Acids Res. 22:5016-5023 (1994)), Sph elements (Suzuki et al., Plant Cell 9:799-807 1997)), elicitor responsive elements, (Fukuda et al., Plant Mol. Biol. 34:81-87 (1997); Rushton et al., EMBO J. 15:5690-5700 (1996)), metal responsive elements (Stuart et al., Nature 317:828-831 (1985); Westin et al., EMBO J. 7:3763-3770 (1988); Thiele et al., Nucleic Acids Res. 20:1183-1191 (1992); Faisst et al., Nucleic Acids Res. 20:3-26 (1992)), low temperature responsive elements, (Baker et al., Plant Mol. Biol. 24:701-713 (1994); Jiang et al., Plant Mol. Biol. 30:679-684 (1996); Nordin et al., Plant Mol. Biol. 21:641-653 (1993); Zhou et al., J. Biol. Chem. 267: 23515-23519 (1992)), drought responsive elements, (Yamaguchi et al., Plant Cell 6:251-264 (1994); Wang et al., Plant Mol. Biol. 28:605-617 (1995); Bray E A, Trends in Plant Science 2:48-54 (1997)) enhancer elements for glutenin, (Colot et al., EMBO J. 6:3559-3564 (1987); Thomas et al., Plant Cell 2:1171-1180 (1990); Kreis et al., Philos. Trans. R. Soc. Lond., B314:355-365 (1986)), light-independent regulatory elements, (Lagrange et al., Plant Cell 9:1469-1479 (1997); Villain et al., J. Biol. Chem. 271:32593-32598 (1996)), OCS enhancer elements, (Bouchez et al., EMBO J. 8:4197-4204 (1989); Foley et al., Plant J. 3:669-679 (1993)), ACGT elements, (Foster et al., FASEB J. 8:192-200 (1994); Izawa et al., Plant Cell 6:1277-1287 (1994); Izawa et al., J. Mol. Biol. 230:1131-1144 (1993)), negative cis elements in plastid related genes, (Zhou et al., J. Biol. Chem. 267:23515-23519 (1992); Lagrange et al., Mol. Cell. Biol. 13:2614-2622 (1993); Lagrange et al., Plant Cell 9:1469-1479 (1997); Zhou et al., J. Biol. Chem. 267:23515-23519 (1992)), prolamin box elements, (Forde et al., Nucleic Acids Res. 13:7327-7339 (1985); Colot et al., EMBO J. 6:3559-3564 (1987); Thomas et al., Plant Cell 2:1171-1180 (1990); Thompson et al., Plant Mol. Biol. 15:755-764 (1990); Vicente et al., Proc. Natl. Acad. Sci. USA 94:7685-7690 (1997)), elements in enhancers from the IgM heavy chain gene (Gillies et al., Cell 33:717-728 (1983); Whittier et al., Nucleic Acids Res. 15:2515-2535 (1987)).

The activity or strength of a promoter may be measured in terms of the amount of mRNA or protein accumulation it specifically produces, relative to the total amount of mRNA or protein. The promoter preferably expresses an operably linked nucleic acid sequence at a level greater than 0.01%; preferably in a range of about 0.5% to about 20% (w/w) of the total cellular RNA or protein.

Alternatively, the activity or strength of a promoter may be expressed relative to a well-characterized promoter (for which transcriptional activity was previously assessed). For example, a less-characterized promoter may be operably linked to a reporter sequence (e.g., GUS) and introduced into a specific cell type. A well-characterized promoter (e.g. the 35S promoter) is similarly prepared and introduced into the same cellular context. Transcriptional activity of the unknown promoter is determined by comparing the amount of reporter expression, relative to the well characterized promoter. In one embodiment, the activity of the present promoter is as strong as the 35S promoter when compared in the same cellular context. The cellular context is preferably maize, sorghum, corn, barley, wheat, canola, soybean, or maize; and more preferably is maize, sorghum, corn, barley, or wheat; and most preferably is soybean or maize.

Enhancers

Enhancers, which strongly activate transcription, frequently in a specific differentiated cell type, are usually 100-200 base pairs long. Although enhancers often lie within a few kilobases of the cap site, in some cases they lie much further upstream or downstream from the cap site or within an intron. Some genes are controlled by more than one enhancer region, as in the case of the *Drosophila* even-skipped gene.

As used herein, the term "enhancer domain" refers to a cis-acting transcriptional regulatory element (cis-element), which confers an aspect of the overall modulation of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from regulatory elements that include such elements, and they can be synthesized with additional flanking nucleotides that contain useful restriction enzyme sites to facilitate subsequence manipulation.

Translational enhancers may also be incorporated as part of a recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Examples of other regulatory element 5' nucleic acid leader sequences include dSSU 5', PetHSP70 5', and GmHSP17.9 5'. A translational enhancer sequence derived from the untranslated leader sequence from the mRNA of the coat protein gene of alfalfa mosaic virus coat protein gene, placed between the promoter and the gene, to increase translational efficiency, is described in U.S. Pat. No. 6,037,527, herein incorporated by reference. Thus, the design, construction, and use of enhancer domains according to the methods disclosed herein for modulating the expression of operably linked transcribable polynucleotide molecules are encompassed by the present invention.

Any of the polynucleotide molecules of the present invention may comprise an enhancer.

Leaders

As used herein, the term "leader" refers to a polynucleotide molecule isolated from the untranslated 5' region (5' UTR) of a genomic copy of a gene and defined generally as a segment between the transcription start site (TSS) and the coding sequence start site. Alternately, leaders may be synthetically produced or manipulated DNA elements. A "plant leader" is a native or non-native leader that is functional in plant cells. A plant leader can be used as a 5' regulatory element for modulating expression of an operably linked transcribable polynucleotide molecule.

For example, non-translated 5' leader polynucleotide molecules derived from heat shock protein genes have been demonstrated to enhance gene expression in plants (see for example, U.S. Pat. Nos. 5,659,122 and 5,362,865, all of which are incorporated herein by reference).

Any of the nucleic acid molecules described herein may comprise nucleic acid sequences comprising leaders. A leader of the present invention preferably assists in the regulation of transcription of a heterologous transcribable polynucleotide sequence at a high level in a plant.

Introns

As used herein, the term "intron" refers to a polynucleotide molecule that may be isolated or identified from the intervening sequence of a genomic copy of a gene and may be defined generally as a region spliced out during mRNA processing prior to translation. Alternately, introns may be synthetically produced or manipulated DNA elements. Introns may themselves contain sub-elements such as cis-elements or enhancer domains that effect the transcription of operably linked genes. A "plant intron" is a native or non-native intron that is functional in plant cells. A plant intron may be used as a regulatory element for modulating expression of an operably linked gene or genes. A polynucleotide molecule sequence in a recombinant construct may comprise introns. The introns may be heterologous with respect to the transcribable polynucleotide molecule sequence.

The transcribable polynucleotide molecule sequence in the recombinant vector may comprise introns. The introns may be heterologous with respect to the transcribable polynucleotide molecule sequence. Examples of regulatory element introns include the corn actin intron and the corn HSP70 intron (U.S. Pat. No. 5,859,347, herein incorporated by reference in its entirety).

Any of the molecule of the present invention may comprise introns. The intron of the present invention preferably affects transcription a heterologous transcribable polynucleotide sequence at a high level in a plant.

Terminators

The 3' untranslated regions (3' UTRs) of mRNAs are generated by specific cleavage and polyadenylation. A 3' polyadenylation region means a DNA molecule linked to and located downstream of a structural polynucleotide molecule and includes polynucleotides that provide a polyadenylation signal and other regulatory signals capable of affecting transcription, mRNA processing or gene expression. PolyA tails are thought to function in mRNA stability and in initiation of translation.

As used herein, the term "terminator" refers to a polynucleotide sequence that may be isolated or identified from the 3' untranslated region (3'UTR) of a transcribable gene, which functions to signal to RNA polymerase the termination of transcription. The polynucleotide sequences of the present invention may comprise terminator sequences.

Polyadenylation is the non-templated addition of a 50 to 200 nt chain of polyadenylic acid (polyA). Cleavage must precede polyadenylation. The polyadenylation signal functions in plants to cause the addition of polyadenylate nucleotides to the 3' end of the mRNA precursor. The polyadenylation sequence can be derived from the natural gene, from a variety of plant genes, or from Agrobacterium T-DNA genes. Transcription termination often occurs at sites considerably downstream of the sites that, after polyadenylation, are the 3' ends of most eukaryotic mRNAs.

Examples of 3' UTR regions are the nopaline synthase 3' region (nos 3'; Fraley, et al., Proc. Natl. Acad. Sci. USA 80: 4803-4807, 1983), wheat hsp17 (T-Ta.Hsp17), and T-Ps.R-bcS2:E9 (pea rubisco small subunit), those disclosed in WO0011200A2 (herein incorporated by reference) and other 3' UTRs known in the art can be tested and used in combination with a DHDPS or AK coding region, herein referred to as T-3'UTR. Another example of terminator regions is given in U.S. Pat. No. 6,635,806, herein incorporated by reference.

Any of the polynucleotide molecules of the present invention may comprise a terminator.

Regulatory Element Isolation and Modification

Any number of methods well known to those skilled in the art can be used to isolate a polynucleotide molecule, or fragment thereof, disclosed in the present invention. For example, PCR (polymerase chain reaction) technology can be used to amplify flanking regions from a genomic library of a plant using publicly available sequence information. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated from genomic DNA by designing oligonucleotide primers based on available sequence information and using PCR techniques.

As used herein, the term "isolated polynucleotide molecule" refers to a polynucleotide molecule at least partially separated from other molecules normally associated with it in its native state. In one embodiment, the term "isolated" is also used herein in reference to a polynucleotide molecule that is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. The term "isolated" as used herein is intended to encompass molecules not present in their native state.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Short nucleic acid sequences having the ability to specifically hybridize to complementary nucleic acid sequences may be produced and utilized in the present invention. These short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed. Use of these probes may greatly facilitate the identification of transgenic plants which contain the presently disclosed nucleic acid molecules. The probes may also be used to screen cDNA or genomic libraries for additional nucleic acid sequences related or sharing homology to the presently disclosed promoters and transcribable polynucleotide sequences. The short nucleic acid sequences may be used as probes and specifically as PCR probes. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3, STSPipeline, or GeneUp (Pesole, et al., *BioTechniques* 25:112-123, 1998), for example, can be used to identify potential PCR primers.

Alternatively, the short nucleic acid sequences may be used as oligonucleotide primers to amplify or mutate a complementary nucleic acid sequence using PCR technology. These primers may also facilitate the amplification of related complementary nucleic acid sequences (e.g. related nucleic acid sequences from other species).

The primer or probe is generally complementary to a portion of a nucleic acid sequence that is to be identified, amplified, or mutated. The primer or probe should be of sufficient length to form a stable and sequence-specific duplex molecule with its complement. The primer or probe preferably is about 10 to about 200 nucleotides long, more preferably is about 10 to about 100 nucleotides long, even more preferably is about 10 to about 50 nucleotides long, and most preferably is about 14 to about 30 nucleotides long. The primer or probe may be prepared by direct chemical synthesis, by PCR (See, for example, U.S. Pat. Nos. 4,683,195, and 4,683,202, each of which is herein incorporated by reference), or by excising the nucleic acid specific fragment from a larger nucleic acid molecule.

Transcribable Polynucleotide Molecules

A regulatory element of the present invention may be operably linked to a transcribable polynucleotide sequence that is heterologous with respect to the regulatory element. The term "heterologous" refers to the relationship between two or more nucleic acid or protein sequences that are derived from different sources. For example, a promoter is heterologous with respect to a transcribable polynucleotide sequence if such a combination is not normally found in nature. In addition, a particular sequence may be "heterologous" with respect to a cell or organism into which it is inserted (i.e. does not naturally occur in that particular cell or organism).

The transcribable polynucleotide molecule may generally be any nucleic acid sequence for which an increased level of transcription is desired. Alternatively, the regulatory element and transcribable polynucleotide sequence may be designed to down-regulate a specific nucleic acid sequence. This is typically accomplished by linking the promoter to a transcribable polynucleotide sequence that is oriented in the antisense direction. One of ordinary skill in the art is familiar with such antisense technology. Briefly, as the antisense nucleic acid sequence is transcribed, it hybridizes to and sequesters a complimentary nucleic acid sequence inside the cell. This duplex RNA molecule cannot be translated into a protein by the cell's translational machinery. Any nucleic acid sequence may be negatively regulated in this manner.

A regulatory element of the present invention may also be operably linked to a modified transcribable polynucleotide molecule that is heterologous with respect to the promoter. The transcribable polynucleotide molecule may be modified to provide various desirable features. For example, a transcribable polynucleotide molecule may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

Due to the degeneracy of the genetic code, different nucleotide codons may be used to code for a particular amino acid. A host cell often displays a preferred pattern of codon usage. Transcribable polynucleotide molecules are preferably constructed to utilize the codon usage pattern of the particular host cell. This generally enhances the expression of the transcribable polynucleotide sequence in a transformed host cell. Any of the above described nucleic acid and amino acid sequences may be modified to reflect the preferred codon usage of a host cell or organism in which they are contained. Modification of a transcribable polynucleotide sequence for optimal codon usage in plants is described in U.S. Pat. No. 5,689,052, herein incorporated by reference.

Additional variations in the transcribable polynucleotide molecules may encode proteins having equivalent or superior characteristics when compared to the proteins from which they are engineered. Mutations may include, but are not limited to, deletions, insertions, truncations, substitutions, fusions, shuffling of motif sequences, and the like. Mutations to a transcribable polynucleotide molecule may be introduced in either a specific or random manner, both of which are well known to those of skill in the art of molecular biology.

Thus, one embodiment of the invention is a regulatory element such as provided in SEQ ID NO: 1 through SEQ ID NO: 18, operably linked to a transcribable polynucleotide molecule so as to modulate transcription of said transcribable polynucleotide molecule at a desired level or in a desired tissue or developmental pattern upon introduction of said construct into a plant cell. In one embodiment, the transcribable polynucleotide molecule comprises a protein-coding region of a gene, and the regulatory element affects the transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Genes of Agronomic Interest

The transcribable polynucleotide molecule preferably encodes a polypeptide that is suitable for incorporation into the diet of a human or an animal. Specifically, such transcribable polynucleotide molecules comprise genes of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. Suitable transcribable polynucleotide molecules include but are not limited to those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, or an insecticidal protein.

In one embodiment of the invention, a polynucleotide molecule as shown in SEQ ID NO: 1 through SEQ ID NO: 18, or complements thereof, or fragments thereof, or cis elements thereof comprising regulatory elements is incorporated into a construct such that a polynucleotide molecule of the present invention is operably linked to a transcribable polynucleotide molecule that is a gene of agronomic interest.

The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175), increased yield (U.S. Pat. RE38,446; U.S. Pat. Nos. 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013,864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. RE37,543; U.S. Pat. Nos. 6,228,623; 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700). The genetic elements, methods, and transgenes described in the patents listed above are incorporated herein by reference.

Alternatively, a transcribable polynucleotide molecule can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects a phenotype or morphology change of interest may be useful for the practice of the present invention.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670, which is incorporated herein by reference), green fluorescent protein (GFP described in U.S. Pat. Nos. 5,491,084 and 6,146,826, all of which are incorporated herein by reference), proteins that confer antibiotic resistance, or proteins that confer herbicide tolerance. Marker genes in genetically modified plants are generally of two types: genes conferring antibiotic resistance or genes conferring herbicide tolerance.

Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art.

Herbicides for which transgenic plant tolerance has been demonstrated and the method of the present invention can be applied, include but are not limited to: glyphosate, glufosinate, sulfonylureas, imidazolinones, bromoxynil, delapon, dicamba, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS described in U.S. Pat. Nos. 5,627,061, 5,633,435, 6,040,497 and in 5,094,945 for glyphosate tolerance, all of which are incorporated herein by reference); polynucleotides encoding a glyphosate oxidoreductase and a glyphosate-N-acetyl transferase (GOX described in U.S. Pat. No. 5,463,175 and GAT described in U.S. Patent publication 20030083480, dicamba monooxygenase U.S. Patent publication 20030135879, all of which are incorporated herein by reference); a polynucleotide molecule encoding bromoxynil nitrilase (Bxn described in U.S. Pat. No. 4,810,648 for Bromoxynil tolerance, which is incorporated herein by reference); a polynucleotide molecule encoding phytoene desaturase (crti) described in Misawa et al, (1993) *Plant J.* 4:833-840 and Misawa et al, (1994) *Plant J.* 6:481-489 for norflurazon tolerance; a polynucleotide molecule encoding acetohydroxyacid synthase (AHAS, aka ALS) described in Sathasiivan et al (1990) *Nucl. Acids Res.* 18:2188-2193 for tolerance to sulfonylurea herbicides; and the bar gene described in DeBlock, et al (1987) *EMBO J.* 6:2513-2519 for glufosinate and bialaphos tolerance. The regulatory elements of the present invention can express transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

Constructs and Vectors

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permit the integration of the T-DNA into the genome of a plant cell (see for example U.S. Pat. No. 6,603,061, herein incorporated by reference in its entirety). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* AB1, C58, or LBA4404, however, other strains known to those skilled in the art of plant transformation can function in the present invention.

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see for example, Molecular Cloning: A Laboratory Manual, 3rd edition Volumes 1, 2, and 3 (2000) J. F. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908, 4,940, 835, 4,769,061 and 4,757,011, all of which are herein incorporated by reference in their entirety. These type of vectors have also been reviewed (Rodriguez, et al. Vectors: A Survey of Molecular Cloning Vectors and Their Uses, Butterworths, Boston, 1988; Glick et al., Methods in Plant Molecular Biology and Biotechnology, CRC Press, Boca Raton, Fla., 1993). Typical vectors useful for expression of nucleic acids in higher plants are well known in the art and include vectors derived from the tumor-inducing (Ti) plasmid of *Agrobacterium tumefaciens* (Rogers, et al., Meth. In Enzymol, 153: 253-277, 1987). Other recombinant vectors useful for plant transformation, including the pCaMVCN transfer control vector, have also been described (Fromm et al., Proc. Natl. Acad. Sci. USA, 82(17): 5824-5828, 1985).

Regulatory Elements in the Construct

Various untranslated regulatory sequences may be included in the recombinant vector. Any such regulatory sequences may be provided in a recombinant vector with other regulatory sequences. Such combinations can be designed or modified to produce desirable regulatory features. Constructs of the present invention would typically comprise one or more gene expression regulatory elements operably linked to a transcribable polynucleotide molecule operably linked to a 3' transcription termination polynucleotide molecule.

Constructs of the present invention may also include additional 5' untranslated regions (5' UTR) of an mRNA polynucleotide molecule or gene which can play an important role in translation initiation. For example, non-translated 5' leader polynucleotide molecules derived from heat shock protein genes have been demonstrated to enhance gene expression in plants (see for example, U.S. Pat. Nos. 5,659,122 and 5,362, 865, all of which are incorporated herein by reference). These additional upstream regulatory polynucleotide molecules may be derived from a source that is native or heterologous with respect to the other elements present on the construct.

One or more additional promoters may also be provided in the recombinant vector. These promoters may be operably linked to any of the transcribable polynucleotide sequences described above. Alternatively, the promoters may be operably linked to other nucleic acid sequences, such as those encoding transit peptides, selectable marker proteins, or antisense sequences. These additional promoters may be selected on the basis of the cell type into which the vector will be inserted. Promoters which function in bacteria, yeast, and plants are all well taught in the art. The additional promoters may also be selected on the basis of their regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described (Poszkowski, et al., *EMBO J.,* 3: 2719, 1989; Odell, et al., *Nature,* 313:810, 1985; Chau et al., *Science,* 244:174-181. 1989).

Often-used constitutive promoters include the CaMV 35S promoter (Odell, et al., *Nature,* 313: 810, 1985), the enhanced CaMV 35S promoter, the Figwort Mosaic Virus (FMV) promoter (Richins, et al., *Nucleic Acids Res.* 20: 8451, 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams, et al., *Biotechnology* 10:540-543, 1992), induced by application of safeners (substituted benzenesulfonamide herbicides; Hershey and Stoner, *Plant Mol. Biol.* 17: 679-690, 1991), heat-shock promoters (Ou-Lee et al., *Proc. Natl. Acad. Sci. U.S.A.* 83: 6815, 1986; Ainley et al., *Plant Mol. Biol.* 14: 949, 1990), a nitrate-inducible promoter derived from the spinach nitrite reductase transcribable polynucleotide sequence (Back et al., *Plant Mol. Biol.* 17: 9, 1991), hormone-inducible promoters (Yamaguchi-Shinozaki et al., *Plant Mol. Biol.* 15: 905, 1990), and light-inducible promoters associated with the small subunit of RuBP carboxylase and LHCP families (Kuhlemeier et al., *Plant Cell* 1: 471, 1989; Feinbaum et al., *Mol. Gen. Genet.* 226: 449-456, 1991; Weisshaar, et al., *EMBO J.* 10: 1777-1786, 1991; Lam and Chua, *J. Biol. Chem.* 266: 17131-17135, 1990; Castresana et al., *EMBO J.* 7: 1929-1936, 1988; Schulze-Lefert, et al., *EMBO J.* 8: 651, 1989).

Examples of useful tissue-specific, developmentally-regulated promoters include the β-conglycinin 7Sα promoter (Doyle et al., *J. Biol. Chem.* 261: 9228-9238, 1986; Slighton and Beachy, *Planta* 172: 356, 1987), and seed-specific promoters (Knutzon, et al., *Proc. Natl. Acad. Sci. U.S.A.* 89: 2624-2628, 1992; Bustos, et al., *EMBO J.* 10: 1469-1479, 1991; Lam and Chua, *Science* 248: 471, 1991). Plant functional promoters useful for preferential expression in seed plastid include those from plant storage proteins and from proteins involved in fatty acid biosynthesis in oilseeds. Examples of such promoters include the 5' regulatory regions from such transcribable polynucleotide sequences as napin (Kridl et al., *Seed Sci. Res.* 1: 209, 1991), phaseolin, zein, soybean trypsin inhibitor, ACP, stearoyl-ACP desaturase, and oleosin. Seed-specific regulation is discussed in EP 0 255 378.

Another exemplary tissue-specific promoter is the lectin promoter, which is specific for seed tissue. The Lectin protein in soybean seeds is encoded by a single transcribable polynucleotide sequence (Le1) that is only expressed during seed maturation and accounts for about 2 to about 5% of total seed mRNA. The lectin transcribable polynucleotide sequence and seed-specific promoter have been fully characterized and used to direct seed specific expression in transgenic tobacco plants (Vodkin, et al., *Cell,* 34: 1023, 1983; Lindstrom, et al., *Developmental Genetics,* 11: 160, 1990).

Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel, et al., *Plant Mol. Biol,* 29: 995-1004, 1995); corn sucrose synthetase 1 (Yang, et al., *Proc. Natl. Acad. Sci. USA,* 87: 4144-48, 1990); corn alcohol dehydrogenase 1 (Vogel, et al., *J. Cell Biochem.,* (Suppl) 13D: 312, 1989); corn light harvesting complex (Simpson, *Science,* 233: 34, 1986); corn heat shock protein (Odell, et al., *Nature,* 313: 810, 1985); the chitinase promoter from *Arabidopsis* (Samac, et al., *Plant Cell,* 3:1063-1072, 1991); the LTP (Lipid Transfer Protein) promoters from broccoli (Pyee, et al., *Plant J.,* 7: 49-59, 1995); petunia chalcone isomerase (Van Tunen, et al., *EMBO J.* 7: 1257, 1988); bean glycine rich protein 1 (Keller, et al., *EMBO L.,* 8: 1309-1314, 1989); Potato patatin (Wenzler, et al., *Plant Mol. Biol.,* 12: 41-50, 1989); the ubiquitin promoter from maize (Christensen et al., *Plant Mol. Biol.,* 18: 675,689, 1992); and the actin promoter from corn (McElroy, et al., *Plant Cell,* 2:163-171, 1990).

The additional promoter is preferably seed selective, tissue specific, constitutive, or inducible. The promoter is most preferably the nopaline synthase (NOS), octopine synthase (OCS), mannopine synthase (MAS), cauliflower mosaic virus 19S and 35S (CaMV19S, CaMV35S), enhanced CaMV (eCaMV), ribulose 1,5-bisphosphate carboxylase (ssRUBISCO), figwort mosaic virus (FMV), CaMV derived AS4, tobacco RB7, wheat POX1, tobacco EIF-4, lectin protein (Le1), or corn RC2 promoter.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5'.

The recombinant vector may further comprise a nucleic acid sequence encoding a transit peptide. This peptide may be useful for directing a protein to the extracellular space, a chloroplast, or to some other compartment inside or outside of the cell (see, e.g., European Patent Application Publication Number 0218571, herein incorporated by reference).

The transcribable polynucleotide sequence in the recombinant vector may comprise introns. The introns may be heterologous with respect to the transcribable polynucleotide sequence. Preferred introns include the corn actin intron and the corn HSP70 intron.

In addition, constructs may include additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). A 3' non-translated region typically provides a transcriptional termination signal, and a polyadenylation signal which functions in plants to cause the addition of adenylate nucleotides to the 3' end of the mRNA. These may be obtained from the 3' regions to the nopaline synthase (nos) coding sequence, the soybean 7Sa storage protein coding sequence, the albumin coding sequence, and the pea ssRUBISCO E9 coding sequence. Particularly preferred 3' nucleic acid sequences include nos 3', E9 3', ADR12 3', 7Sα 3', 11S 3', and albumin 3'. Typically, nucleic acid sequences located a few hundred base pairs downstream of the polyadenylation site serve to terminate transcription. These regions are required for efficient polyadenylation of transcribed mRNA. These additional downstream regulatory polynucleotide molecules may be derived from a source that is native or heterologous with respect to the other elements present on the construct.

Transcribable Polynucleotides in the Construct

The promoter in the recombinant vector is preferably operably linked to a transcribable polynucleotide sequence. Exemplary transcribable polynucleotide sequences, and modified forms thereof, are described in detail above. The promoter of the present invention may be operably linked to a transcribable polynucleotide sequence that is heterologous with respect to the promoter. In one aspect, the transcribable polynucleotide sequence may generally be any nucleic acid sequence for which an increased level of transcription is desired. The transcribable polynucleotide sequence preferably encodes a polypeptide that is suitable for incorporation into the diet of a human or an animal. Suitable transcribable polynucleotide sequences include those encoding a yield protein, a stress tolerance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, or an insecticidal protein.

Alternatively, the promoter and transcribable polynucleotide sequence may be designed to down-regulate a specific nucleic acid sequence. This is typically accomplished by linking the promoter to a transcribable polynucleotide sequence that is oriented in the antisense direction. One of ordinary skill in the art is familiar with such antisense technology. Using such an approach, a cellular nucleic acid sequence is effectively down regulated as the subsequent steps of translation are disrupted. Nucleic acid sequences may be negatively regulated in this manner.

Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829; posttranscriptional gene suppression using a construct with a sense-oriented transcribable polynucleotide molecule to regulate gene expression in plants is disclosed in U.S. Pat. Nos. 5,283,184 and 5,231,020, all of which are hereby incorporated by reference.

Thus, one embodiment of the invention is a construct comprising a regulatory element such as provided in SEQ ID NO: 1 through SEQ ID NO: 18, operably linked to a transcribable polynucleotide molecule so as to modulate transcription of said transcribable polynucleotide molecule at a desired level or in a desired tissue or developmental pattern upon introduction of said construct into a plant cell. In one embodiment, the transcribable polynucleotide molecule comprises a protein-coding region of a gene, and the regulatory element affects the transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Exemplary transcribable polynucleotide molecules for incorporation into constructs of the present invention include, for example, polynucleotide molecules or genes from a species other than the target species or genes that originate with or are present in the same species, but are incorporated into recipient cells by genetic engineering methods rather than classical reproduction or breeding techniques. The type of polynucleotide molecule can include but is not limited to a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

The constructs of this invention comprising a regulatory element identified or isolated from *Zea mays* may further comprise one or more transcribable polynucleotide molecules. In one embodiment of the invention, a polynucleotide molecule as shown in SEQ ID NO: 1 through SEQ ID NO: 8, or any complements thereof, or any fragments thereof, comprising regulatory elements such as promoters, leaders and chimeric regulatory elements, is incorporated into a construct such that a polynucleotide molecule of the present invention is operably linked to a transcribable polynucleotide molecule that is a selectable marker or a gene of agronomic interest.

The gene regulatory elements of the present invention can be incorporated into a construct using selectable markers and tested in transient or stable plant analyses to provide an indication of the regulatory element's gene expression pattern in stable transgenic plants. Current methods of generating transgenic plants employ a selectable marker gene which is transferred along with any other genes of interest usually on the same DNA molecule. The presence of a suitable marker is necessary to facilitate the detection of genetically modified plant tissue during development.

Thus, in one embodiment of the invention, a polynucleotide molecule of the present invention as shown in SEQ ID NO: 1 through SEQ ID NO: 18, or fragments thereof, or complements thereof, or cis elements thereof is incorporated into a polynucleotide construct such that a polynucleotide molecule of the present invention is operably linked to a transcribable polynucleotide molecule that provides for a selectable, screenable, or scorable marker. The constructs containing the regulatory elements operably linked to a marker gene may be delivered to the tissues and the tissues analyzed by the appropriate mechanism, depending on the marker. The quantitative or qualitative analyses are used as a tool to evaluate the potential expression profile of a regulatory element when operatively linked to a gene of agronomic interest in stable plants. Any marker gene, described above, may be used in a transient assay.

Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate regulatory elements operably linked to any transcribable polynucleotide molecule, including but not limited to marker genes or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Transformation

The invention is also directed to a method of producing transformed cells and plants which comprise, in a 5' to 3' orientation, a gene expression regulatory element operably linked to a heterologous transcribable polynucleotide sequence. Other sequences may also be introduced into the cell, including 3' transcriptional terminators, 3' polyadenylation signals, other translated or untranslated sequences, transit or targeting sequences, selectable markers, enhancers, and operators.

The term "transformation" refers to the introduction of nucleic acid into a recipient host. The term "host" refers to bacteria cells, fungi, animals and animal cells, plants and plant cells, or any plant parts or tissues including protoplasts, calli, roots, tubers, seeds, stems, leaves, seedlings, embryos, and pollen. As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. The term "transgenic" refers to an animal, plant, or other organism containing one or more heterologous nucleic acid sequences.

There are many methods for introducing nucleic acids into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.*, 42: 205, 1991).

Technology for introduction of DNA into cells is well known to those of skill in the art. Methods and materials for transforming plant cells by introducing a plant polynucleotide construct into a plant genome in the practice of this invention can include any of the well-known and demonstrated methods including:

(1) chemical methods (Graham and Van der Eb, *Virology*, 54(2): 536-539, 1973; Zatloukal, et al., *Ann. N.Y. Acad. Sci.*, 660: 136-153, 1992);

(2) physical methods such as microinjection (Capecchi, *Cell*, 22(2): 479-488, 1980), electroporation (Wong and Neumann, *Biochim. Biophys. Res. Commun.*, 107(2): 584-587, 1982; Fromm et al., *Proc. Natl. Acad. Sci. USA*, 82(17): 5824-5828, 1985; U.S. Pat. No. 5,384,253, herein incorporated by reference) particle acceleration (Johnston and Tang, *Methods Cell Biol.*, 43(A): 353-365, 1994; Fynan et al., *Proc. Natl. Acad. Sci. USA*, 90(24): 11478-11482, 1993) and microprojectile bombardment (as illustrated in U.S. Pat. Nos. 5,015,580; 5,550,318; 5,538,880; 6,160,208; 6,399,861; and 6,403,865, all of which are herein incorporated by reference);

(3) viral vectors (Clapp, *Clin. Perinatol.*, 20(1): 155-168, 1993; Lu, et al., *J. Exp. Med.*, 178(6): 2089-2096, 1993; Eglitis and Anderson, *Biotechniques*, 6(7): 608-614, 1988);

(4) receptor-mediated mechanisms (Curiel et al., *Hum. Gen. Ther.*, 3(2):147-154, 1992; Wagner, et al., *Proc. Natl. Acad. Sci. USA*, 89(13): 6099-6103, 1992), and (5) bacterial mediated mechanisms such as *Agrobacterium*-mediated transformation (as illustrated in U.S. Pat. Nos. 5,824,877; 5,591,616; 5,981,840; and 6,384,301, all of which are herein incorporated by reference);

(6) Nucleic acids can be directly introduced into pollen by directly injecting a plant's reproductive organs (Zhou, et al., *Methods in Enzymology*, 101: 433, 1983; Hess, *Intern Rev. Cytol.*, 107: 367, 1987; Luo, et al., *Plant Mol. Biol. Reporter*, 6: 165, 1988; Pena, et al., *Nature*, 325: 274, 1987).

(7) Protoplast transformation, as illustrated in U.S. Pat. No. 5,508,184 (herein incorporated by reference).

(8) The nucleic acids may also be injected into immature embryos (Neuhaus, et al., *Theor. Appl. Genet.*, 75: 30, 1987).

Any of the above described methods may be utilized to transform a host cell with one or more gene regulatory elements of the present invention and one or more transcribable polynucleotide molecules. Host cells may be any cell or organism such as a plant cell, algae cell, algae, fungal cell, fungi, bacterial cell, or insect cell. Preferred hosts and transformants include cells from: plants, *Aspergillus*, yeasts, insects, bacteria and algae.

The prokaryotic transformed cell or organism is preferably a bacterial cell, even more preferably an *Agrobacterium*, *Bacillus*, *Escherichia*, *Pseudomonas* cell, and most preferably is an *Escherichia coli* cell. Alternatively, the transformed organism is preferably a yeast or fungal cell. The yeast cell is preferably a *Saccharomyces cerevisiae*, *Schizosaccharomyces pombe*, or *Pichia pastoris*. Methods to transform such cells or organisms are known in the art (EP 0238023; Yelton et al, *Proc. Natl. Acad. Sci. (U.S.A.)*, 81:1470-1474 (1984); Malardier et al, *Gene*, 78:147-156 (1989); Becker and Guarente, In: Abelson and Simon (eds.,), *Guide to Yeast Genetics and Molecular Biology, Methods Enzymol.*, Vol. 194, pp. 182-187, Academic Press, Inc., New York; Ito et al, *J. Bacteriology*, 153:163 (1983); Hinnen et al., *Proc. Natl. Acad. Sci. (U.S.A.)*, 75:1920 (1978); Bennett and LaSure (eds.), *More Gene Manipulations in Fungi*, Academic Press, CA (1991)). Methods to produce proteins of the present invention from such organisms are also known (Kudla et al., *EMBO*, 9:1355-1364 (1990); Jarai and Buxton, *Current Genetics*, 26:2238-2244 (1994); Verdier, *Yeast*, 6:271-297 (1990); MacKenzie et al., *Journal of Gen. Microbiol.*, 139: 2295-2307 (1993); Hartl et al., *TIBS*, 19:20-25 (1994); Bergeron et al., *TIBS*, 19:124-128 (1994); Demolder et al., *J. Biotechnology*, 32:179-189 (1994); Craig, *Science*, 260: 1902-1903 (1993); Gething and Sambrook, *Nature*, 355:33-45 (1992); Puig and Gilbert, *J. Biol. Chem.*, 269:7764-7771 (1994); Wang and Tsou, *FASEB Journal*, 7:1515-1517 (9193); Robinson et al., *Bio/Technology*, 1:381-384 (1994); Enderlin and Ogrydziak, *Yeast*, 10:67-79 (1994); Fuller et al., *Proc. Natl. Acad. Sci. (U.S.A)*, 86:1434-1438 (1989); Julius et al., *Cell*, 37:1075-1089 (1984); Julius et al., *Cell*, 32:839-852 (1983)).

Another preferred embodiment of the present invention is the transformation of a plant cell. A plant transformation construct comprising a regulatory element of the present invention may be introduced into plants by any plant transformation method.

Methods for transforming dicotyledons, primarily by use of *Agrobacterium tumefaciens* and obtaining transgenic plants have been published for cotton (U.S. Pat. Nos. 5,004, 863; 5,159,135; 5,518,908, all of which are herein incorporated by reference); soybean (U.S. Pat. Nos. 5,569,834; 5,416,011, all of which are herein incorporated by reference; McCabe, et al., *Biotechnolgy*, 6: 923, 1988; Christou et al., *Plant Physiol.* 87:671-674 (1988)); *Brassica* (U.S. Pat. No. 5,463,174, herein incorporated by reference); peanut (Cheng et al., *Plant Cell Rep.* 15:653-657 (1996), McKently et al., Plant Cell Rep. 14:699-703 (1995)); papaya; and pea (Grant et al., Plant Cell Rep. 15:254-258 (1995)).

Transformation of monocotyledons using electroporation, particle bombardment and *Agrobacterium* have also been reported. Transformation and plant regeneration have been achieved in asparagus (Bytebier et al., *Proc. Natl. Acad. Sci. (USA)* 84:5354 (1987)); barley (Wan and Lemaux, *Plant Physiol* 104:37 (1994)); maize (Rhodes et al., *Science* 240: 204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995)); oat (Somers et al., *Bio/Technology* 10:1589 (1992)); orchard grass (Horn et al., *Plant Cell Rep.* 7:469 (1988)); corn (Toriyama et al., *Theor Appl. Genet.* 205:34 (1986); Part et al., *Plant Mol. Biol.* 32:1135-1148 (1996); Abedinia et al., *Aust. J. Plant Physiol.* 24:133-141 (1997); Zhang and Wu, *Theor. Appl. Genet.* 76:835 (1988); Zhang et al., *Plant Cell Rep.* 7:379 (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *Bio/Technology* 10:691 (1992)) and wheat (Vasil et al., *Bio/Technology* 10:667 (1992); U.S. Pat. No. 5,631,152, herein incorporated by reference).

The regeneration, development, and cultivation of plants from transformed plant protoplast or explants is well taught in the art (Weissbach and Weissbach, *Methods for Plant Molecular Biology*, (Eds.), Academic Press, Inc., San Diego, Calif., 1988; Horsch et al., *Science*, 227: 1229-1231, 1985). In this method, transformants are generally cultured in the presence of a selective media which selects for the successfully transformed cells and induces the regeneration of plant shoots (Fraley et al., *Proc. Natl. Acad. Sci. U.S.A.*, 80: 4803, 1983). These shoots are typically obtained within two to four months.

The shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant strain employed.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transformed plants are analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of the plants of this invention can be harvested from fertile transgenic plants and be used to grow progeny generations of transformed plants of this invention including hybrid plant lines comprising the construct of this invention and expressing a gene of agronomic interest. The present invention also provides for parts of the plants of the present invention. Plant parts, without limitation, include seed, endosperm, ovule and pollen. In a particularly preferred embodiment of the present invention, the plant part is a seed.

The invention also includes and provides transformed plant cells which comprise a nucleic acid molecule of the present invention.

The transgenic plant may pass along the transformed nucleic acid sequence to its progeny. The transgenic plant is preferably homozygous for the transformed nucleic acid sequence and transmits that sequence to all of its offspring upon as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified.

Each periodical, patent, and other document or reference cited herein is herein incorporated by reference in its entirety.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Generating a Genomic Bacterial Artificial Chromosome (BAC) Library

BACs are stable, non-chimeric cloning systems having genomic fragment inserts (100-300 kb) and their DNA can be prepared for most types of experiments including DNA sequencing. BAC vector, pBeloBAC11, is derived from the endogenous *E. coli* F-factor plasmid, which contains genes for strict copy number control and unidirectional origin of DNA replication. Additionally, pBeloBAC11 has three unique restriction enzyme sites (Hind III, Bam HI and Sph I) located within the LacZ gene which can be used as cloning sites for megabase-size plant DNA. Indigo, another BAC vector contains Hind III and Eco R I cloning sites. This vector also contains a random mutation in the LacZ gene that allows for darker blue colonies.

As an alternative, the P1-derived artificial chromosome (PAC) can be used as a large DNA fragment cloning vector (Ioannou, et al., Nature Genet. 6:84-89 (1994); Suzuki, et al., Gene 199:133-137 (1997)). The PAC vector has most of the features of the BAC system, but also contains some of the elements of the bacteriophage P1 cloning system. BAC libraries are generated by ligating size-selected restriction digested DNA with pBeloBAC11 followed by electroporation into *E. coli*. BAC library construction and characterization is extremely efficient when compared to YAC (yeast artificial chromosome) library construction and analysis, particularly because of the chimerism associated with YACs and difficulties associated with extracting YAC DNA.

There are general methods for preparing megabase-size DNA from plants. For example, the protoplast method yields megabase-size DNA of high quality with minimal breakage. A process involves preparing young leaves which are manually feathered with a razor-blade before being incubated for four to five hours with cell-wall-degrading enzymes. A second method developed by Zhange et al., Plant J. 7:175-184 (1995), is a universal nuclei method that works well for several divergent plant taxa. Fresh or frozen tissue is homogenized with a blender or mortar and pestle. Nuclei are then isolated and embedded. DNA prepared by the nucleic method is often more concentrated and is reported to contain lower amounts of chloroplast DNA than the protoplast method.

Once protoplasts or nuclei are produced, they are embedded in an agarose matrix as plugs or microbeads. The agarose provides a support matrix to prevent shearing of the DNA while allowing enzymes and buffers to diffuse into the DNA. The DNA is purified and manipulated in the agarose and is stable for more than one year at 4° C.

Once high molecular weight DNA is prepared, it is fragmented to the desired size range. In general, DNA fragmentation utilizes two general approaches, 1) physical shearing and 2) partial digestion with a restriction enzyme that cuts relatively frequently within the genome. Since physical shearing is not dependent upon the frequency and distribution of particular restriction enzymes sites, this method should yield the most random distribution of DNA fragments. However, the ends of the sheared DNA fragments must be repaired and cloned directly or restriction enzyme sites added by the addition of synthetic linkers. Because of the subsequent steps required to clone DNA fragmented by shearing, most protocols fragment DNA by partial restriction enzyme digestion. The advantage of partial restriction enzyme digestion is that no further enzymatic modification of the ends of the restriction fragments are necessary. Four common techniques that can be used to achieve reproducible partial digestion of megabase-size DNA are 1) varying the concentration of the restriction enzyme, 2) varying the time of incubation with the restriction enzyme 3) varying the concentration of an enzyme cofactor (e.g., Mg2+) and 4) varying the ratio of endonuclease to methylase.

There are three cloning sites in pBeloBAC11, but only Hind III and Bam HI produce 5' overhangs for easy vector dephosphorylation. These two restriction enzymes are primarily used to construct BAC libraries. The optimal partial digestion conditions for megabase-size DNA are determined by wide and narrow window digestions. To optimize the optimum amount of Hind III, 1, 2, 3, 10, and 5-units of enzyme are each added to 50 ml aliquots of microbeads and incubated at 37° C. for 20 minutes.

After partial digestion of megabase-size DNA, the DNA is run on a pulsed-field gel, and DNA in a size range of 100-500 kb is excised from the gel. This DNA is ligated to the BAC vector or subjected to a second size selection on a pulsed field gel under different running conditions. Studies have previously reported that two rounds of size selection can eliminate small DNA fragments co-migrating with the selected range in the first pulse-field fractionation. Such a strategy results in an increase in insert sizes and a more uniform insert size distribution.

A practical approach to performing size selections is to first test for the number of clones/microliter of ligation and insert size from the first size selected material. If the numbers are good (500 to 2000 white colony/microliter of ligation) and the size range is also good (50 to 300 kb) then a second size selection is practical. When performing a second size selection one expects a 80 to 95% decrease in the number of recombinant clones per transformation.

Twenty to two hundred nanograms of the size-selected DNA is ligated to dephosphorylated BAC vector (molar ratio of 10 to 1 in BAC vector excess). Most BAC libraries use a molar ratio of 5 to 15:1 (size selected DNA:BAC vector). Transformation is carried out by electroporation and the transformation efficiency for BACs is about 40 to 1,500 transformants from one microliter of ligation product or 20 to 1000 transformants/ng DNA.

Several tests can be carried out to determine the quality of a BAC library. Three basic tests to evaluate the quality include: the genome coverage of a BAC library-average insert size, average number of clones hybridizing with single copy probes and chloroplast DNA content. The determination of the average insert size of the library is assessed in two ways. First, during library construction every ligation is tested to determine the average insert size by assaying 20-50 BAC clones per ligation. DNA is isolated from recombinant clones using a standard mini preparation protocol, digested with Not I to free the insert from the BAC vector and then sized using pulsed field gel electrophoresis (Maule, Molecular Biotechnology 9:107-126 (1998)).

To determine the genome coverage of the library, it is screened with single copy RFLP markers distributed randomly across the genome by hybridization. Microtiter plates containing BAC clones are spotted onto Hybond membranes. Bacteria from 48 or 72 plates are spotted twice onto one membrane resulting in 18,000 to 27,648 unique clones on each membrane in either a 4×4 or 5×5 orientation. Since each clone is present twice, false positives are easily eliminated and true positives are easily recognized and identified.

Finally, the chloroplast DNA content in the BAC library is estimated by hybridizing three chloroplast genes spaced evenly across the chloroplast genome to the library on high density hybridization filters.

There are strategies for isolating rare sequences within the genome. For example, higher plant genomes can range in size from 100 Mb/1C (*Arabidopsis*) to 15,966 Mb/C (*Triticum aestivum*), (Arumuganathan and Earle, Plant Mol Bio Rep. 9:208-219 (1991)). The number of clones required to achieve a given probability that any DNA sequence will be represented in a genomic library is $N=(\ln(1-P))/(\ln(1-L/G))$ where N is the number of clones required, P is the probability desired to get the target sequence, L is the length of the average clone insert in base pairs and G is the haploid genome length in base pairs (Clarke et al., Cell 9:91-100 (1976)). The rice BAC library of the present invention is constructed in the pBeloBAC11 or similar vector. Inserts are generated by partial Eco RI or other enzymatic digestion of DNA. The 25× library provides 4-5× coverage sequence from BAC clones across genome.

Example 2

Sequencing Genomic DNA Inserts from a Genomic BAC Library

Two basic methods can be used for DNA sequencing, the chain termination method of Sanger et al., Proc. Natl. Acad. Sci. USA 74:5463-5467 (1977), and the chemical degradation method of Maxam and Gilbert, Proc. Natl. Acad. Sci. USA 74:560-564 (1977). Automation and advances in technology such as the replacement of radioisotopes with fluorescence-based sequencing have reduced the effort required to sequence DNA (Craxton, Methods, 2:20-26 (1991); Ju et al., Proc. Natl. Acad. Sci. USA 92:4347-4351 (1995); Tabor and Richardson, Proc. Natl. Acad. Sci. USA 92:6339-6343 (1995)). Automated sequencers are available from, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

In addition, advances in capillary gel electrophoresis have also reduced the effort required to sequence DNA and such advances provide a rapid high resolution approach for sequencing DNA samples (Swerdlow and Gesteland, Nucleic Acids Res. 18:1415-1419 (1990); Smith, Nature 349:812-813 (1991); Luckey et al., Methods Enzymol. 218:154-172 (1993); Lu et al., J. Chromatog. A. 680:497-501 (1994); Carson et al., Anal. Chem. 65:3219-3226 (1993); Huang et al., Anal. Chem. 64:2149-2154 (1992); Kheterpal et al., Electrophoresis 17:1852-1859 (1996); Quesada and Zhang, Electrophoresis 17:1841-1851 (1996); Baba, Yakugaku Zasshi 117: 265-281 (1997)).

A number of sequencing techniques are known in the art, including fluorescence-based sequencing methodologies. These methods have the detection, automation and instrumentation capability necessary for the analysis of large volumes of sequence data. Currently, the 377 DNA Sequencer (Perkin-Elmer Corp., Applied Biosystems Div., Foster City, Calif.) allows the most rapid electrophoresis and data collection. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed (Birren et al., Genome Analysis: Analyzing DNA, 1, Cold Spring Harbor, N.Y. (1999)).

PHRED is used to call the bases from the sequence trace files (http://www.mbt.washington.edu). Phred uses Fourier methods to examine the four base traces in the region surrounding each point in the data set in order to predict a series of evenly spaced predicted locations. That is, it determines where the peaks would be centered if there were no compressions, dropouts, or other factors shifting the peaks from their "true" locations. Next, PHRED examines each trace to find the centers of the actual, or observed peaks and the areas of these peaks relative to their neighbors. The peaks are detected independently along each of the four traces so many peaks overlap. A dynamic programming algorithm is used to match the observed peaks detected in the second step with the predicted peak locations found in the first step.

After the base calling is completed, contaminating sequences (*E. coli*, BAC vector sequences >50 bases and sub-cloning vector are removed and constraints are made for the assembler. Contigs are assembled using CAP3 (Huang, et al., Genomics 46: 37-45 (1997)). A two-step re-assembly process is employed to reduce sequence redundancies caused by overlaps between BAC clones. In the first step, BAC clones are grouped into clusters based on overlaps between contig sequences from different BACs. These overlaps are identified by comparing each sequence in the dataset against every other sequences, by BLASTN. BACs containing overlaps greater than 5,000 base pairs in length and greater than 94% in sequence identity are put into the same cluster. Repetitive sequences are masked prior to this procedure to avoid false joining by repetitive elements present in the genome. In the second step, sequences from each BAC cluster are assembled by PHRAP.longread, which is able to handle very long sequences. A minimum match is set at 100 bp and a minimum score is set at 600 as a threshold to join input contigs into longer contigs.

Example 3

Identifying Genes within a Genomic BAC Library

This example illustrates the identification of combigenes within the rice genomic contig library as assembled in Example 2. The genes and partial genes that are embedded in such contigs are identified through a series of informatic analyses. The tools to define genes fall into two categories: homology-based and predictive-based methods. Homology-based searches (e.g., GAP2, BLASTX supplemented by NAP and TBLASTX) detect conserved sequences during comparisons of DNA sequences or hypothetically translated protein sequences to public and/or proprietary DNA and protein databases. Existence of an *Oryza sativa* gene is inferred if significant sequence similarity extends over the majority of the target gene. Since homology-based methods may overlook genes unique to *Oryza sativa*, for which homologous nucleic acid molecules have not yet been identified in databases, gene prediction programs are also used. Predictive methods employed in the definition of the *Oryza sativa* genes included the use of the GenScan gene predictive software program which is available from Stanford University (e.g., at the website: gnomic/stanford.edu/GENSCANW.html, and the Genemark.hmm for Eukaryotes program from Gene Probe, Inc (Atlanta, Ga.) www.geneprobe.net/index.htm). GenScan, in general terms, infers the presence and extent of a gene through a search for "gene-like" grammar. GeneMark.hmm searches a file containing DNA sequence data for genes. It employs a Hidden Markov Model algorithm with a species-specific inhomogeneous Markov model of gene-encoding regions of DNA.

The homology-based methods that are used to define the *Oryza sativa* gene set included GAP2, BLASTX supplemented by NAP and TBLASTX. For a description of BLASTX and TBLASTX see Coulson, Trends in Biotechnology 12:76-80 (1994) and Birren et al., Genome Analysis, 1:543-559 (1997). GAP2 and NAP are part of the Analysis and Annotation Tool (AAT) for Finding Genes in Genomic Sequences which was developed by Xiaoqiu Huang at Michigan Tech University and is available at the web site genome.cs.mtu.edu/. The AAT package includes two sets of programs, one set DPS/NAP (referred to as "NAP") for comparing the query sequence with a protein database, and the other set DDS/GAP2 (referred to as "GAP2") for comparing the query sequence with a cDNA database. Each set contains a fast database search program and a rigorous alignment program. The database search program identifies regions of the query sequence that are similar to a database sequence. Then the alignment program constructs an optimal alignment for each region and the database sequence. The alignment program also reports the coordinates of exons in the query sequence. See Huang, et al., Genomics 46: 37-45 (1997). The GAP2 program computes an optimal global alignment of a genomic sequence and a cDNA sequence without penalizing terminal gaps. A long gap in the cDNA sequence is given a constant penalty. The DNA-DNA alignment by GAP2 adjusts penalties to accommodate introns. The GAP2 program makes use of splice site consensuses in alignment computation. GAP2 delivers the alignment in linear space, so long sequences can be aligned. See Huang, Computer Applications in the Biosciences 1-235 (1994). The GAP2 program aligns the *Oryza sativa* contigs with a library of 42,260 *Oryza sativa* cDNAs. The NAP program computes a global alignment of a DNA sequence and a protein sequence without penalizing terminal gaps. NAP handles frameshifts and long introns in the DNA sequence. The program delivers the alignment in linear space, so long sequences can be aligned. It makes use of splice site consensuses in alignment computation. Both strands of the DNA sequence are compared with the protein sequence and one of the two alignments with the larger score is reported. See Huang, and Zhang, Computer Applications in the Biosciences 12(6), 497-506 (1996).

NAP takes a nucleotide sequence, translates it in three forward reading frames and three reverse complement reading frames, and then compares the six translations against a protein sequence database (e.g. the non-redundant protein (i.e., nr-aa database maintained by the National Center for Biotechnology Information as part of GenBank).

The first homology-based search for genes in the *Oryza sativa* contigs is effected using the GAP2 program and the *Oryza sativa* library of clustered *Oryza sativa* cDNA. The *Oryza sativa* clusters are mapped onto an assembly of *Oryza sativa* contigs using the GAP2 program. GAP2 standards for selecting a DNA-DNA match are >92% sequence identity with the following parameters:
  gap extension penalty=1
  match score=2
  gap open penalty=6
  gap length for constant penalty=20
  mismatch penalty=-2
  minimum exon length=21
  minimum total length of all exons in a gene (in nucleotide)=200

When a particular *Oryza sativa* cDNA aligns to more than one *Oryza sativa* contig, the alignment with the highest identity is selected and alignments with lower levels of identity are filtered out as surreptitious alignments. *Oryza sativa* cDNA sequences aligning to *Oryza sativa* contigs with exceptionally low complexity are filtered out when the basis for alignment included a high number of cDNAs with poly A tails aligning to genomic regions with extended repeats of A or T.

The second homology-based method used for gene discovery is BLASTX hits extended with the NAP software package. BLASTX is run with the *Oryza sativa* genomic contigs as queries against the GenBank non-redundant protein data library identified as "nr-aa". NAP is used to better align the amino acid sequences as compared to the genomic sequence. NAP extends the match in regions where BLASTX has identified high-scoring-pairs (HSPs), predicts introns, and then links the exons into a single ORF prediction. Experience suggests that NAP tends to mis-predict the first exon. The NAP parameters are:
  gap extension penalty=1
  gap open penalty=15
  gap length for constant penalty=25
  min exon length (in aa)=7
  minimum total length of all exons in a gene (in nucleotide)=200
  homology >40%

The NAP alignment score and GenBank reference number for best match are reported for each contig for which there is a NAP hit.

In the final homology-based method, TBLASTX, is used with cDNA information from four plant sequencing projects: 27,037 sequences from *Triticum aestivum*, 136,074 sequences from *Glycine max*, 71,822 sequences from *Zea mays* and 68,517 sequences from *Arabidopsis thaliana*. Conservative standards for inclusion of TBLASTX hits into the gene set are utilized. These standards are a minimal E value of 1IE-16, and a minimal match of 150 bp in *Oryza sativa* contig.

The GenScan program is "trained" with *Arabidopsis thaliana* characteristics. Though better than the "off-the-shelf" version, the GenScan trained to identify *Oryza sativa* genes proved more proficient at predicting exons than predicting full-length genes. Predicting full-length genes is compromised by point mutations in the unfinished contigs, as well as by the short length of the contigs relative to the typical length of a gene. Due to the errors found in the full-length gene predictions by GenScan, inclusion of GenScan-predicted genes is limited to those genes and exons whose probabilities are above a conservative probability threshold. The GenScan parameters are:
  weighted mean GenScan P value >0.4
  mean GenScan T value >0
  mean GenScan Coding score >50
  length >200 bp
  minimum total length of all exons in a gene=500

The weighted mean GenScan P value is a probability for correctly predicting ORFs or partial ORFs and is defined as the (1/SS li)(SS li Pi), where "l" is the length of a exon and "P" is the probability or correctness for the exon.

The GeneMark.hmm for Eukaryotes program uses the Hidden Markov model for species *Oryza Sativa*. Minimum total length of all exons in a gene is 500 bp. Except for the model selection, there is no specific run-time parameter for GeneMark.hmm.

The gene predictions from these programs are stored in a database and then combigenes are derived from these predictions. A combigene is a cluster of putative genes which satisfy the following criteria:
  All genes making up a single combigene are located on the same strand of a contig;
  Maximum intron size of a valid gene is 4000 bp;
  Maximum distance between any two genes in the same combigene is 200 bp, as measured by the bases between adjacent ending exons;
  If an individual gene is predicted by NAP it has at least 40% sequence identity to its hit;
  If an individual gene is predicted by GAP2 it has at least 92% sequence identity to its hit;
  If an individual gene is predicted by Genscan the weighted average of the probabilities calculated for all of its exons is not less than 0.4. The gene boundaries of a Genscan-predicted gene are determined while taking into account only exons.

Since TBLASTX-predicted genes are standless the combigene which is made up of such genes can be assigned a strand only if there is a gene in the cluster that was predicted by a strand-defining gene-predicting program.

Example 4

Identifying Promoters in the Genomic BAC Library using Bioinformatic Techniques

Candidate promoter sequences are selected by identifying the regions of DNA located immediately upstream of "combigenes" as described and defined in Example 3. The length of the region to be extracted from the corresponding contig's sequence is set to be 1500 nucleotides plus the very first nucleotide of a combigene. Thus, if a combigene is sufficiently far from the edge of a contig a 1501 nucleotide sequence is obtained, otherwise the sequence will be shorter. Only coding region predictions are considered when building combigenes. Therefore, the 5' UTR of the putative cDNA is included as part of the combigene upstream region.

If there is an AAT/NAP-predicted component in a combigene, then the putative promoter sequence is extracted upstream of the beginning of that component, otherwise—the sequence is extracted upstream of the beginning of the combigene (which may correspond to Genscan, AAT/GAP or a TBLASTX prediction).

Promoter candidates are further selected using bioinformatic analysis of the candidate promoter sequence.

The candidate promoter regions listed in SEQ ID NO:1 through SEQ ID NO:57467 are analyzed for known promoter motifs listed in Table 2.

The identification of such motifs provides important information about the candidate promoter. For example, some motifs are associated with informative annotations such as "light inducible binding site" or "stress inducible binding motif" and can be used to select with confidence a promoter that is able to confer light inducibility or stress inducibility to an operably-linked transgene, respectively.

Putative promoter sequences are also searched with matrices for the TATA box, GC box (factor name: V_GC_01) and CCAAT box (factor name: F_HAP234_01). The matrix for the TATA box is from the Eukaryotic Promoter Database (http://www.epd.isb-sib.ch/) and the matrices for the GC box and the CCAAT box are from Transfac.

The algorithm that is used to annotate promoters searches for matches to both sequence motifs and matrix motifs. First, individual matches are found. For sequence motifs, a maximum number of mismatches is allowed (see Table 2). If the code M,R,W,S,Y, or K are listed in the sequence motif (each of which is a degenerate code for 2 nucleotides) ½ mismatch is allowed. If the code B, D, H, or V are listed in the sequence motif (each of which is a degenerate code for 3 nucleotides) ⅓ mismatch is allowed. p values are determined by simulation with a 5 Mb of random DNA with the same dinucleotide frequency as the test set is generated and the probability of a given matrix score is determined (number of hits/5e7). Once the individual hits have been found, the putative promoter sequence is searched for clusters of hits in a 250 bp window. The score for a cluster is found by summing the negative natural log of the p value for each individual hit. Using 100 Mb simulations as described above, the probability of a window having a cluster score greater than or equal to the given value is determined. Clusters with a p value more significant than p<1e-6 are reported. Only the top 287 hits are taken and are ranked by p value. Effects of repetitive elements are screened. If the 287th ranked hit has the same p value as the first ranked hit, no results are reported for that factor.

For matrix motifs, a p value cutoff is used on a matrix score. The matrix score is determined by adding the path of a given DNA sequence through a matrix. P values are determined by simulation; 5 Mb of random DNA with the same dinucleotide frequency as a test set is generated to test individual matrix hits and 100 Mb is used to test clusters; the probability of a given matrix score and the probability scores for clusters are determined as are the sequence motifs. The usual cutoff for matrices is 2.5e-4. No clustering is done for the TATA box, GC box or CCAAT box.

Candidate promoters are also selected based on the expression characteristics of the gene that is cis-associated with the candidate promoter, (i.e. the native gene). For example, a promoter region located 5' to a gene, which is expressed during a specific stage of development, likely plays a key role in the temporal regulation of that gene. Thus the promoter, when operably linked to a heterologous coding sequence, may similarly regulate the heterologous coding sequence.

Combining the motif analysis with the expression analysis, the list of candidate promoters having desired properties can be narrowed. This decreases the overall number of candidate promoters that must be screened to confirm the promoter's function. For example, one can start with seed-expressed transcription factors, identify candidate promoters that match the consensus regulation sites for seed-expressed transcription factors, and then test the identified candidate promoters to confirm the promoter sub-set which are capable of conferring seed-specific expression to a gene.

Example 5

Identifying Promoters in the Genomic BAC Library using an Expression Assay

Promoters may also be identified based on quantitative analysis of genes that are cis-associated with candidate promoters, (i.e. the native genes). In this method, the native genes associated with SEQ ID NO: 1 through SEQ ID NO: 18 are analyzed on a digital northern blot. Digital northern data can be generated from EST sequencing, SAGE and other methods, which in effect count RNA molecules expressed in cell. This data can be generated as needed, or is generally available to the public on a number of web sites (e.g., www.tigr.org). Data can be obtained from any plant species, although data on rice gene expression is particularly preferred. Promoters are selected based on the expression information of the digital northern. For example, identifying genes expressing genes under stress-related conditions would provide a group of promoters able to confer such stress-inducible expression to other genes.

Example 6

Identifying Promoters in the Genomic BAC Library using Microarray Analysis

Promoters may also be selected based by transcriptional profiling or microarray analysis. Transcriptional profiling can be completed on large scale for each cis-linked gene associated with SEQ ID NO: 1 through SEQ ID NO: 18. Transcription profiling data can be obtained on RNA prepared from any plant species using a chip comprised of sequences from any plant species, although data generated from rice using a rice chip is preferred.

A comprehensive database of transcription profiling data narrows down the list of promoter candidates that confer a desired expression pattern. For example, a promoter that confers drought-specific expression can be selected by identifying a cis-linked gene that is induced under drought conditions (on the microarray), but is not expressed at other stages of plant growth and development. Such a promoter is likely to confer drought inducibility to an operably linked transgene. Public databases of transcript profiling data are becoming more comprehensive and thereby enabling this type of analysis.

Example 7

Functional Screening of Promoters in an Expression Assay

Promoters are screened in an expression assay. The promoters in SEQ ID NO: 1 through SEQ ID NO: 18 are amplified by PCR from rice genomic DNA and cloned into an expression vector containing a reporter transgene (e.g., GUS or GFP). The individual promoter or a collection of promoters ("promoter library") are then screened in an expression assay for the ability to express the reporter transgene. In a common expression assay for leaf promoters, the promoters are transfected into rice or maize leaf protoplasts. Reporter gene expression in the protoplasts indicates a promoter capable of conferring gene-expression in the leaf. The promoters are also transfected into protoplasts from other tissues or plant species to identify other regulatory features of the promoter.

Alternatively, promoters may be screened using a particle gun technique to bombard the cells, tissues or plants. The bombarded samples are visually inspected for reporter gene expression. Reporter gene expression observed in any bombarded samples indicates the presence of a promoter able to confer expression of a transgene in that cell, tissue or plant.

The promoters may also be screened in plants where transformation protocols have been greatly enhanced to facilitate the screening of large numbers of promoters. In this approach, the individual rice promoters or "promoter library" is transformed into *Arabidopsis* plants. The resulting transformed tissues or progeny are scored for reporter expression. Again, reporter gene expression in a given tissue indicates that a promoter is able to confer transgene expression in that tissue.

For some promoters, such as those providing constitutive expression, a reporter transgene can be replaced with a selectable marker transgene, such as a gene conferring glyphosate tolerance. Transformed cells, tissues or plants expressing the selectable marker are selected, rather than visually scored. For example, the promoter is linked to a selectable marker, such as glyphosate resistance, and then screening for male sterile plants. The selected plants, in this case male sterile plants, may contain a promoter for male reproductive tissues.

The promoters described herein can also be used to ablate or kill cells expressing a gene from the promoter. In such cases, the promoter is operably linked to a negative selectable marker gene, including but not limited to the diptheria toxin gene, or to a conditional lethal gene, including but not limited to the phosphonate ester hydrolase gene (pehA). The negative selectable marker gene is transformed into cells, tissues or plants. The cells, tissues or plants which express the negative selectable gene from the promoter are selectively killed. In the case of the conditional lethal gene, the transformed cells, tissues or plants which express the conditional lethal gene are only killed in the presence of the negative selective agent or negative selective condition. In the example of the phosphonate ester hydrolase gene, the transformed cells, tissues or plants which express the conditional lethal gene are only killed in the presence of glyceryl glyphoste.

Example 8

Identification and Cloning of Regulatory Elements

Regulatory elements are isolated from *Oryza sativa* genomic DNA. All regulatory elements are sub-cloned into a plant transformation vector operably linking the regulatory elements to the *Zea mays* HSP70 intron (1-Zm.DnaK-1:1:1, described in U.S. Pat. No. 5,424,412, which is incorporated herein by reference), the coding region for β-glucuronidase (GUS described in U.S. Pat. No. 5,599,670, which is incorporated herein by reference), and the *Agrobacterium tumefaciens* NOS gene terminator.

Variants of the rice Metallothionein (MTH) gene's regulatory elements may be isolated from *Oryza sativa* genomic DNA using sequence specific primers and PCR amplification methods.

The present invention thus provides isolated polynucleotide molecules having gene regulatory activity (regulatory elements) and DNA constructs comprising the isolated regulatory elements operably linked to a transcribable polynucleotide molecule.

Example 9

Corn Plant Transformation and GUS analysis

Corn plants are transformed with plant expression constructs for histochemical GUS analysis in plants. Plants are transformed using methods known to those skilled in the art. Particle bombardment of corn H99 immature zygotic embryos may be used to produce transgenic maize plants. Ears of maize H99 plants are collected 10-13 days after pollination from greenhouse grown plants and sterilized. Immature zygotic embryos of 1.2-1.5 mm are excised from the ear and incubated at 28° C. in the dark for 3-5 days before use as target tissue for bombardment. DNA comprising an isolated expression cassette containing the selectable marker for kanamycin resistance (NPTII gene) and the screenable marker for β-D-Glucuronidase (GUS gene) is gel purified and used to coat 0.6 micron gold particles (Catalog #165-2262 Bio-Rad, Hercules, Calif.) for bombardment. Macro-carriers are loaded with the DNA-coated gold particles (Catalog #165-2335 Bio-Rad, Hercules Calif.). The embryos are transferred onto osmotic medium scutellum side up. A PDS1000/He biolistic gun is used for transformation (Catalog #165-2257 Bio-Rad, Hercules Calif.). Bombarded immature embryos are cultured and transgenic calli are selected and transferred to tissue formation medium. Transgenic corn plants are regenerated from the transgenic calli and transferred to the greenhouse.

GUS activity is qualitatively and quantitatively measured using methods known to those skilled in the art. Plant tissue samples are collected from the same tissue for both the qualitative and quantitative assays. For qualitative analysis, whole tissue sections are incubated with the GUS staining solution X-Gluc (5-bromo-4-chloro-3-indolyl-β-glucuronide) (1 milligram/milliliter) for an appropriate length of time, rinsed, and visually inspected for blue coloration. For quantitative analysis, total protein is first extracted from each tissue sample. One microgram of total protein is used with the fluorogenic substrate 4-methyleumbelliferyl -β-D-glucuronide (MUG) in a total reaction volume of 50 μl (microliters). The reaction product 4-methylumbelliferone (4-MU) is maximally fluorescent at high pH. Addition of a basic solution of sodium carbonate simultaneously stops the assay and adjusts the pH for quantifying the fluorescent product. Fluorescence is measured with excitation at 365 nm, emission at 445 nm using a Fluoromax-3 with Micromax Reader, with slit width set at excitation 2 nm and emission 3 nm. The GUS activity is expressed as pmole of 4-MU/micrograms of protein/hour (pMole of 4-MU/μg protein/hour).

Example 10

MTH Regulatory Element Analysis in Stable Transgenic Corn Plants

Corn plants representing nine F1 events (plants representing an independent event produced from R0 transgenic plants crossed with non-transgenic H99 plants) transformed with pMON94302 (comprising SEQ ID NO: 16) were analyzed for GUS activity as described above. Corn plants representing ten F1 events (plants representing an independent event produced from R0 transgenic plants crossed with non-transgenic H99 plants) transformed with pMON84008 (comprising SEQ ID NO:11) were analyzed for GUS activity as described above. Mean levels of GUS activity (pMole of 4-MU/μg protein/hour) for each stage of plant development and organ tested are provided as mean GUS activity +/−standard error (SE) measurements. Abbreviations include: none detected by visible detection methods (ND), three leaf stage (V3), seven leaf stage (V7), tasseling stage (VT), days after germination (DAG), and days after pollination (DAP) are used. Mean levels of GUS activity (pMole of MU/μg protein/hour) for each stage of plant development and organ tested are provided in Table 2 and Table 3 below. Specific cell types for which GUS expression was noted are provided in Table 3.

TABLE 2

Os.MTH Regulatory Element Expression in Transgenic Corn Plant Tissues pMON94302 P-Os.Metallothionein-a-1:1:7

| Stages | Organ | Inducer | Range | Mean ± SE |
|---|---|---|---|---|
| Imbibed seed | Embryo | — | 4.18-4.18 | 4.18 ± 0.00 |
| Imbibed seed | Endosperm | — | 2.72-2.72 | 2.72 ± 0.00 |
| 3 DAG | Root | — | 126.00-286.79 | 220.91 ± 48.63 |
| V3 | Root main | Unstress | 104.68-237.08 | 148.73 ± 29.91 |
| V3 | Root crown | — | 42.25 257.78 | 171.88 ± 48.47 |
| V7 | Root seminal | — | 11.46-819.32 | 265.37 ± 120.91 |
| V7 | Root crown | — | 16.93 993.98 | 294.39 ± 136.87 |
| VT | Root seminal | — | 8.15-15.04 | 11.59 ± 3.45 |
| VT | Root crown | — | 149.41 180.08 | 164.75 ± 15.33 |
| 3 DAG | Coleoptile | — | 138.83-375.19 | 264.31 ± 37.23 |
| V3 | Leaf | Unstress | 381.95-1116.41 | 730.12 ± 185.74 |
| V7 | Leaf - Mature | — | 48.67-71.77 | 61.46 ± 4.88 |
| VT | Internode | — | 89.68 473.01 | 205.88 ± 69.93 |
| VT | Cob | — | 23.92-223.94 | 99.01 ± 44.80 |
| VT | Anther | — | 20.48-40.97 | 32.78 ± 4.37 |
| VT | Pollen | — | <0.1 <0.1 | <0.1 ± 0.00 |
| VT | Silk | — | 15.77 35.03 | 23.33 ± 5.93 |
| 21 DAP | Embryo | — | <0.1-<0.1 | <0.1 ± 0.00 |
| 35 DAP | Embryo | — | 5.57-13.22 | 9.39 ± 3.83 |
| 10 DAP | Kernal | — | 18.73-259.87 | 105.57 ± 12.71 |
| 21 DAP | Endosperm | — | 11.28-140.04 | 72.86 ± 12.97 |
| 35 DAP | Endosperm | — | 25.90-53.71 | 37.62 ± 3.44 |

Range—lowest and highest activity of individual seedlings across events;
Mean/SE—overall mean across all the events
DAG—Days After Germination;
DAP—Days After Pollination;
Em—Embryo;
En—Endosperm;
VT—Tasseling stage;
IS—Imbibed seed;
C—coleoptile;
R—Root;
L—Leaf;
V3—three leaf stage;
V7—Seven leaf stage;
nd—not determined

TABLE 3

Os.MTH Regulatory Element Expression in Transgenic Corn Plant Tissues pMON84008 P-Os.Metallothionein-b-1:1:2

| Stages | Organ | Inducer | Range | Mean ± SE |
|---|---|---|---|---|
| Imbibed seed | Embryo | — | 17.05-17.05 | 17.05 ± 0.00 |
| Imbibed seed | Endosperm | — | <0.1-<0.1 | <0.1 ± 0.00 |
| 3 DAG | Root | — | 10.32-836.89 | 330.82 ± 256.01 |
| V3 | Root main | Unstress | <0.1-<0.1 | <0.1 ± 0.00 |
| V3 | Root crown | Unstress | <0.1 <0.1 | <0.1 ± 0.00 |
| V3 | Root main | Cold | 2.27-2.27 | 2.27 ± 0.00 |
| V3 | Root crown | Cold | <0.1 <0.1 | <0.1 ± 0.00 |
| V3 | Root main | Desiccation | <0.1-<0.1 | <0.1 ± 0.00 |
| V3 | Root crown | Desiccation | nd nd | nd ± 0.00 |
| V7 | Root seminal | — | <0.1-<0.1 | <0.1 ± 0.00 |
| V7 | Root crown | — | <0.1 <0.1 | <0.1 ± 0.00 |
| VT | Root seminal | — | 46.78-46.78 | 46.78 ± 0.00 |
| VT | Root crown | — | 20.97 20.97 | 20.97 ± 0.00 |
| 3 DAG | Coleoptile | — | 11.78-757.74 | 199.07 ± 114.28 |
| V3 | Leaf | Unstress | <0.1-<0.1 | <0.1 ± 0.00 |
| V3 | Leaf | Cold | 15.60-15.60 | 15.60 ± 0.00 |
| V3 | Leaf | Desiccation | 25.57-25.57 | 25.57 ± 0.00 |
| V7 | Leaf - Mature | — | <0.1-0.00 | <0.1 ± 0.00 |
| V7 | Leaf - Young | — | 1.09-1.09 | 1.09 ± 0.00 |
| VT | Leaf - Mature | — | <0.1-<0.1 | <0.1 ± 0.00 |
| VT | Leaf - Senescence | — | <0.1-<0.1 | <0.1 ± 0.00 |
| VT | Internode | — | 25.86 48.10 | 36.98 ± 11.12 |
| VT | Cob | — | 11.29-32.29 | 21.79 ± 10.50 |
| VT | Anther | — | 53.57-53.57 | 53.57 ± 0.00 |
| VT | Pollen | — | 18.51 584.48 | 207.97 ± 80.44 |
| VT | Silk | — | 4.91 18.28 | 10.18 ± 1.28 |
| 14 DAP | Embryo | — | 62.40-165.15 | 113.77 ± 51.37 |
| 21 DAP | Embryo | — | <0.1-<0.1 | <0.1 ± 0.00 |
| 35 DAP | Embryo | — | 0.43-2.05 | 1.10 ± 0.49 |
| 7 DAP | Kernal | — | <0.1-<0.1 | <0.1 ± 0.00 |
| 14 DAP | Endosperm | — | <0.1-<0.1 | <0.1 ± 0.00 |
| 21 DAP | Endosperm | — | <0.1-<0.1 | <0.1 ± 0.00 |
| 35 DAP | Endosperm | — | 0.43-0.43 | 0.43 ± 0.00 |

Range—lowest and highest activity of individual seedlings across events;
Mean/SE—overall mean across all the events
DAG—Days After Germination;
DAP—Days After Pollination;
Em—Embryo;
En—Endosperm;
VT—Tasseling stage;
IS—Imbibed seed;
C—coleoptile;
R—Root;
L—Leaf;
V3—three leaf stage;
V7—Seven leaf stage;
nd—not determined The Os.MTH expression elements have thus been shown to be useful in expressing transgenes in the cell types and developmental stages as shown above. Having taught the isolation, identification, transformation and expression analysis of two rice Metallothionein gene expression regulatory elements, it is within the ordinary skill of the art to apply the same principles for testing of other such elements.

The present invention thus provides DNA constructs comprising regulatory elements that can modulate expression of an operably linked transcribable polynucleotide molecule and a transgenic plant stably transformed with the DNA construct. From the examples given, the present invention thus provides isolated regulatory elements and isolated promoter fragments from *Oryza sativa*, particularly Metallothionein gene regulatory elements, that are useful for modulating the expression of an operably linked transcribable polynucleotide molecule. The present invention also provides a method for assembling DNA constructs comprising the isolated regulatory elements and isolated promoter fragments, and for creating a transgenic plant stably transformed with the DNA construct.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

We claim:

1. A polynucleotide construct comprising a regulatory polynucleotide molecule selected from the group consisting of:
   (a) the nucleic acid sequence of SEQ ID NO:16;
   (b) a fragment of SEQ ID NO:16 with promoter activity; and
   (c) a nucleic acid sequence that exhibits a 99% or greater sequence identity to SEQ ID NO:16 and has promoter activity,
   wherein said regulatory polynucleotide molecule is operably linked to a heterologous transcribable polynucleotide molecule.

2. The polynucleotide construct of claim 1, wherein said transcribable polynucleotide molecule is a gene of agronomic interest.

3. The polynucleotide construct of claim 1, wherein said transcribable polynucleotide molecule is a gene controlling the phenotype of a trait selected from the group consisting of: herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production.

4. The polynucleotide construct of claim 3, wherein said herbicide tolerance gene is selected from the group consisting of genes that encode for: phosphinothricin acetyltransferase, glyphosate resistant EPSPS, hydroxyphenyl pyruvate dehydrogenase, dalapon dehalogenase, bromoxynil resistant nitrilase, anthranilate synthase, glyphosate oxidoreductase and glyphosate-N-acetyl transferase.

5. A transgenic plant cell stably transformed with the polynucleotide construct of claim 1.

6. A transgenic plant stably transformed with the polynucleotide construct of claim 1.

7. A seed of said transgenic plant of claim 6, wherein the seed comprises the construct.

8. A progeny of the plant of claim 6, wherein the progeny comprises said construct.

9. The transgenic plant cell of claim 5, wherein said plant cell is from a monocotyledonous plant selected from the group consisting of wheat, maize, rye, rice, corn, oat, barley, turfgrass, sorghum, millet and sugarcane.

10. The transgenic plant of claim 6, wherein said plant is a monocotyledonous plant selected from the group consisting of wheat, maize, rye, rice, corn, oat, barley, turfgrass, sorghum, millet and sugarcane.

11. A seed of the transgenic plant of claim 10, wherein the seed comprises the construct.

12. The transgenic plant cell of claim 5, wherein said plant cell is from a dicotyledonous plant selected from the group consisting of tobacco, tomato, potato, soybean, cotton, canola, sunflower and alfalfa.

13. The transgenic plant of claim 6, wherein said plant is a dicotyledonous plant selected from the group consisting of tobacco, tomato, potato, soybean, cotton, canola, sunflower and alfalfa.

14. A seed of the transgenic plant of claim 13, wherein the seed comprises the construct.

15. A method of inhibiting weed growth in a field of transgenic glyphosate-tolerant crop plants comprising
   a) planting the transgenic glyphosate-tolerant crop plants in the field, wherein the plants are transformed with an expression cassette comprising the polynucleotide construct of claim 1 operably linked to a polynucleotide molecule encoding a glyphosate tolerance gene; and
   b) applying glyphosate to the field at an application rate that inhibits the growth of weeds, wherein the growth and yield of the transgenic crop plant is not substantially affected by the glyphosate application.

* * * * *